United States Patent
Nilsson et al.

(10) Patent No.: US 7,071,180 B2
(45) Date of Patent: *Jul. 4, 2006

(54) CERTAIN ARYLALIPHATIC AND HETEROARYL-ALIPHATIC PIPERAZINYL PYRAZINES AND THEIR USE IN THE TREATMENT OF SEROTONIN-RELATED DISEASES

(75) Inventors: Björn Nilsson, Uppsala (SE); Jan Tejbrant, Enskede (SE); Benjamin Pelcman, Stockholm (SE); Erik Ringberg, Uppsala (SE); Markus Thor, Knivsta (SE); Jonas Nilsson, Uppsala (SE); Mattias Jönsson, Uppsala (SE)

(73) Assignee: Biovitrum AB (SE)

( * ) Notice: Subject to any disclaimer, the term of this patent is extended or adjusted under 35 U.S.C. 154(b) by 127 days.

This patent is subject to a terminal disclaimer.

(21) Appl. No.: 10/873,852

(22) Filed: Jun. 22, 2004

(65) Prior Publication Data

US 2004/0242554 A1 Dec. 2, 2004

Related U.S. Application Data

(63) Continuation of application No. 10/269,670, filed on Oct. 11, 2002, which is a division of application No. 09/589,282, filed on Jun. 8, 2000, now Pat. No. 6,465,467, which is a continuation-in-part of application No. 09/573,348, filed on May 19, 2000, now abandoned.

(60) Provisional application No. 60/137,527, filed on Jun. 3, 1999.

(30) Foreign Application Priority Data

May 21, 1999 (SE) .............................. 9901884

(51) Int. Cl.
| A61K 31/33 | (2006.01) |
| A61K 31/502 | (2006.01) |
| A61K 31/497 | (2006.01) |
| C07D 401/04 | (2006.01) |
| C07D 241/36 | (2006.01) |

(52) U.S. Cl. ............ 514/183; 514/252.11; 514/252.12; 514/235.8; 514/306.2; 514/362; 514/363; 514/249; 544/129; 544/349; 544/353; 544/354; 544/357; 546/84; 546/277.4; 548/134; 548/452; 548/469; 548/511; 548/503; 549/398; 549/399

(58) Field of Classification Search .................. 514/183, 514/249, 252.11, 36, 252.12, 30, 235.8, 363; 544/129, 349, 353, 354, 357; 549/398, 399; 548/134

See application file for complete search history.

(56) References Cited

U.S. PATENT DOCUMENTS 3,253,989 A    5/1966  Moser et al. ............... 167/55

6,465,467 B1 * 10/2002 Nilsson et al. ......... 514/252.11

FOREIGN PATENT DOCUMENTS

| CH | 583715 | 1/1997 |
| DE | 2433397 | 1/1997 |

(Continued)

OTHER PUBLICATIONS

Lumma, W.C. Jr et al., J. of Med. Chem., vol. 21, No. 6 (1978) pp. 536–542.

(Continued)

Primary Examiner—Richard L. Raymond
Assistant Examiner—Sudhaker B. Patel
(74) Attorney, Agent, or Firm—Fish & Richardson P.C.

(57) ABSTRACT

The invention relates to compounds of the general formula (I):

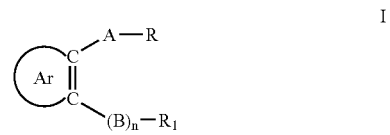

wherein
Ar is optionally substituted aryl or heteroaryl;
A is (i) —O—, —S—, —SO$_2$—, —NH—, (ii) a C$_{1-4}$-alkyl- or C$_{1-6}$-acyl-substituted nitrogen atom or (iii) a C$_{1-8}$-alkylene chain or a heteroalkylene chain having 2 to 8 chain atoms, which optionally contains at least one unsaturation, and which may be substituted and/or contain a bridge to form a saturated or partially or fully unsaturated ring having 3–8 ring members;
B is —C(R$_4$)(R$_5$)—, —OC(R$_4$)(R$_5$)—, —N(R$_6$)C(R$_4$)(R$_5$)—, —N(R$_6$)—, —O—, —S— or —SO$_2$—;
R is optionally substituted C$_{3-8}$-cycloalkyl, aryl or heteroaryl;
R$_1$ is (i) a saturated or unsaturated azacyclic or aminoazacyclic ring, or a saturated diazacyclic or aminodiazacyclic ring, which has 4 to 7 ring members, or a saturated aminoazabicyclic, azabicyclic or diazabicyclic ring which has 7 to 10 ring members, which rings optionally are substituted in one or more positions, or a group —[C(R$_4$)(R$_5$)]$_x$N(R$_{2a}$)(R$_{3a}$)];
R$_{2a}$, R$_{3a}$, R$_4$, R$_5$, R$_6$ and x are as defined in the claims, and n is 0 or 1; and pharmaceutically acceptable salts, hydrates and prodrug forms thereof.

The compounds may be prepared by per se conventional methods and can be used for treating a human or animal subject suffering from a serotonin-related disorder, such as eating disorders, especially obesity, memory disorders, schizophrenia, mood disorders, anxiety disorders, pain, sexual dysfunctions, and urinary disorders. The invention also relates to such use as well as to pharmaceutical compositions comprising a compound of formula (I).

46 Claims, No Drawings

FOREIGN PATENT DOCUMENTS

| | | | |
|---|---|---|---|
| EP | 0572863 | A1 | 12/1993 |
| EP | 0655440 | A2 | 5/1995 |
| EP | 0657426 | A2 | 6/1995 |
| EP | 0711757 | A1 | 5/1996 |
| EP | 0863136 | A1 | 9/1998 |
| GB | 1440722 | | 6/1976 |
| GB | 1457005 | | 12/1976 |
| GB | 1465946 | | 3/1977 |
| WO | WO9501976 | | 1/1995 |
| WO | WO9602525 | A1 | 2/1996 |
| WO | WO9611930 | | 4/1996 |
| WO | WO97/14689 | | 4/1997 |
| WO | WO9842692 | | 10/1998 |
| WO | WO9903833 | | 1/1999 |
| WO | WO9958490 | | 11/1999 |
| WO | WO0012475 | | 3/2000 |
| WO | WO0012482 | | 3/2000 |
| WO | WO0012502 | | 3/2000 |
| WO | WO0012510 | | 3/2000 |

OTHER PUBLICATIONS

Rano et al., *Tetrahedron Letters*, vol. 36, No. 22 (1995) pp. 3789–3792.

Hori et al., Chem. Pharm. Bull., vol. 41, No. 10, (1993) pp. 1832=1841.

Lumma et al., J. of Med. Chem., vol. 24, (1981) pp. 93–101.

Jenck et al., Opin. Invest. Drugs, vol. 7, No. 10 (1998) pp. 1587.

G.A., Kennett, IDrugs, vol. 1, No. 4, (1998) pp. 456–470.

Sargent, P.A. et al., *Psychopharmacology*, vol. 133 (1997) pp. 309–312.

Tecott, L.H. et al., *Nature*, vol. 374 (1995) pp: 542–546.

Dourish, Colin, Obesity Research, vol. 3, No. 4 (1995) pp. 449–462.

Leysen, Dirk C.M., *IDrugs*, vol. 2, No. 2 (1999) pp. 109–120.

Dictionary of Drugs, Chemical Data, Structures and Bibliographies, Chapman and Hall, pp. 504, 972,1158 (1990).

Obata et al., PubMed Abstract 12591127, also cited as Brain Res., 965/1–2, 114–20 (2003).

Volgin et al., PubMed Abstract 12670306, also cited as Eur. J. Neurosci. 17/6, 1179–88 (2003).

Hietala et al., PubMed 11594443, also cited as Psychopharmacology (Berl). 157/2, 180–7 (2001).

Lane RM, PubMed Abstract 9097897, also cited as Psychopharmacol. 11/1, 72–82 (1997).

* cited by examiner

US 7,071,180 B2

CERTAIN ARYLALIPHATIC AND HETEROARYL-ALIPHATIC PIPERAZINYL PYRAZINES AND THEIR USE IN THE TREATMENT OF SEROTONIN-RELATED DISEASES

This application is a continuation of U.S. application Ser. No. 10/269,670, filed on Oct. 11, 2002, which is a divisional of U.S. application Ser. No. 09/589,282, filed Jun. 8, 2000 (now U.S. Pat. No. 6,465,467, issued Oct. 15, 2002), which is a continuation-in-part of U.S. application Ser. No. 09/573,348, filed on May 19, 2000, abandoned, which claims the benefit of U.S. Provisional application Ser. No. 60/137,527, filed on Jun. 3, 1999, and of Swedish Application No. 9901884-8, filed on May 21, 1999, the entire contents each of which are incorporated by reference in their entirety.

FIELD OF THE INVENTION

The present invention relates to novel compounds, to pharmaceutical compositions comprising the compounds, to processes for their preparation, as well as to the use of the compounds for the preparation of a medicament which particularly acts on the central nervous system.

BACKGROUND OF THE INVENTION

Many diseases of the central nervous system are influenced by the adrenergic, the dopaminergic, and the serotonergic neurotransmitter systems. For example, serotonin has been implicated in a number of diseases and conditions which originate in the central nervous system. A number of pharmacological and genetic experiments involving receptors for serotonin strongly implicate the $5\text{-}HT_{2c}$ receptor subtype in the regulation of food intake (Obes. Res. 1995, 3, Suppl. 4, 449S–462S). The $5\text{-}HT_{2c}$ receptor subtype is transcribed and expressed in hypothalamic structures associated with appetite regulation. It has been demonstrated that the non-specific $5\text{-}HT_{2c}$ receptor agonist m-chlorophenylpiperazine (mCPP), which has some preference for the $5\text{-}HT_{2c}$ receptor, causes weight loss in mice that express the normal $5\text{-}HT_{2c}$ receptor while the compound lacks activity in mice expressing the mutated inactive form of the $5\text{-}HT_{2c}$ receptor (Nature 1995, 374, 542–546). In a recent clinical study, a slight but sustained reduction in body weight was obtained after 2 weeks of treatment with mCPP in obese subjects (Psychopharmacology 1997, 133, 309–312). Weight reduction has also been reported from clinical studies with other "serotonergic" agents (see e.g. IDrugs 1998, 1, 456–470). For example, the 5-HT reuptake inhibitor fluoxetine and the 5-HT releasing agent/reuptake inhibitor dexfenfluramine have exhibited weight reduction in controlled studies. However, currently available drugs that increase serotonergic transmission appear to have only a moderate and, in some cases, transient effects on the body weight.

The $5\text{-}HT_{2c}$ receptor subtype has also been suggested to be involved in CNS disorders such as depression and anxiety (Exp. Opin. Invest. Drugs 1998, 7, 1587–1599; IDrugs, 1999, 2, 109–120).

The $5\text{-}HT_{2c}$ receptor subtype has further been suggested to be involved in urinary disorders such as urinary incontinence (IDrugs. 1999, 2, 109–120).

Compounds which have a selective effect on the $5\text{-}HT_{2c}$ receptor may therefore have a therapeutic potential in the treatment of disorders like those mentioned above. Of course, selectivity also reduces the potential for adverse effects mediated by other serotonin receptors.

Information disclosure

U.S. Pat. No. 3,253,989 discloses the use of mCPP as an anorectic agent.

EP-A 1-863 136 discloses azetidine and pyrrolidine derivatives which are selective $5\text{-}HT_{2c}$ receptor agonists having antidepressant activity and which can be used for treating or preventing serotonin-related diseases, including eating disorders and anxiety.

EP-A-657 426 discloses tricyclic pyrrole derivatives having activity on the $5\text{-}HT_{2c}$ receptor and which inter alia may be used for treating eating disorders.

EP-A-655 440 discloses 1-aminoethylindoles having activity on the $5\text{-}HT_{2c}$ receptor and which may be used for treating eating disorders.

EP-A-572 863 discloses pyrazinoindoles having activity on the $5\text{-}HT_{2c}$ receptor and which may be used for treating eating disorders.

J. Med. Chem. 1978, 21, 536–542 and U.S. Pat. No. 4,081,542 disclose a series of piperazinylpyrazines having central serotonin-mimetic activity.

J. Med. Chem. 1981, 24, 93–101 discloses a series of piperazinylquinoxalines with central serotoninmimetic activity.

WO 00/12475 discloses indoline derivatives as $5\text{-}HT_{2b}$ and/or $5\text{-}HT_{2c}$ receptor ligands, especially for the treatment of obesity.

WO 00/12510 discloses pyrroloindoles, pyridoindoles and azepinoindoles as $5\text{-}HT_{2c}$ receptor agonists, particularly for the treatment of obesity.

WO 00/12482 discloses indazole derivatives as selective, directly active $5\text{-}HT_{2c}$ receptor ligands, preferably $5\text{-}HT_{2c}$ receptor agonists, particularly for use as anti-obesity agents.

WO 00/12502 discloses pyrroloquinolines as $5\text{-}HT_{2c}$ receptor agonists particularly for use as anti-obesity agents.

WO 00/12475 discloses indoline derivatives as $5\text{-}HT_{2b}$ and/or $5\text{-}HT_{2c}$ receptor ligands, especially for the treatment of obesity.

GB-B-1,457,005 discloses 1-piperazinyl-2-[2-(phenyl)ethenyl]-quinoxaline derivatives which exhibit anti-inflammatory activity.

Chem. Pharm. Bull. 1993, 41(10) 1832–1841 discloses $5\text{-}HT_3$ antagonists including 2-(4-methyl-1-piperazinyl)-4-phenoxyquinoxaline.

GB-B-1,440,722 discloses 2-(1'-piperazinyl)-quinoxaline compounds having pharmaceutical activity against depression.

WO 96/11920 discloses CNS-active pyridinylurea derivatives.

WO 95/01976 discloses indoline derivatives active as $5\text{-}HT_{2c}$ antagonists and of potential use in the treatment of CNS disorders.

WO 97/14689 discloses aryl-piperazine cyclic amine derivatives which are selective $5\text{-}HT_{1d}$ receptor antagonists.

WO 98/42692 discloses piperazines derived from cyclic amines which are selective antagonists of human $5\text{-}HT_{1a}$, $5\text{-}HT_{1d}$ and $5\text{-}HT_{1b}$ receptors.

GB-B-1,465,946 discloses substituted pyridazinyl, pyrimidinyl and pyridyl compounds which are active as β-receptor blocking agents.

EP-A-711757 discloses [3-(4-phenyl-piperazin-1-yl) propylamino]-pyridine, pyrimidine and benzene derivatives as α-adrenoceptor antagonists.

WO 99/03833 discloses aryl-piperazine derivatives which are $5\text{-}HT_2$ antagonists and $5\text{-}HT_{1a}$ receptor agonists and therefore are useful as remedies or preventives for psychoneurosis.

WO 96/02525 discloses aryl-piperazine-derived piperazide derivatives having 5-HT receptor antagonistic activity.

WO 99/58490 disloses aryl-hydronaphthalen-alkanamines which may effectuate partial or complete blockage of serotonergic 5-$HT_{2c}$ receptors in an organism.

SUMMARY OF THE INVENTION

According to the present invention, a class of novel compounds have been developed which bind to the 5-$HT_{2c}$ receptor (agonists and antagonists) and which therefore may be used for the treatment of serotonin-related disorders.

In one aspect, the invention provides novel compounds of the general formula (I):

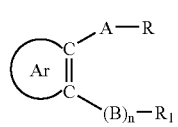

wherein
Ar is aryl or heteroaryl which may be independently substituted in one or more positions by $C_{1-6}$-alkyl, $C_{1-6}$-alkoxy, $C_{1-6}$-alkylthio, $C_{1-6}$-acyl, $C_{1-6}$-alkylsulphonyl, cyano, nitro, hydroxy, $C_{2-6}$-alkenyl, $C_{2-6}$-alkynyl, fluoromethyl, difluoromethyl, trifluoromethyl, difluoromethoxy, trifluoromethoxy, difluoromethylthio, trifluoromethylthio, halogen, —$N(R_2)(R_3)$, aryl, aryloxy, arylthio, aryl-$C_{1-4}$-alkyl, aryl-$C_{2-4}$-alkenyl, aryl-$C_{2-4}$-alkynyl, heterocyclyl, heterocyclyloxy, heterocyclylthio or heterocyclyl-$C_{1-4}$-alkyl, wherein any aryl and heterocyclyl residues as substituents or part of substituents on aryl or heteroaryl in turn may be substituted in one or more positions independently of each other by halogen, $C_{1-6}$-alkyl, $C_{1-6}$-alkoxy, $C_{1-6}$-alkylthio, $C_{1-6}$-acyl, $C_{1-6}$-alkylsulphonyl, nitro, trifluoromethyl, trifluoromethylthio, cyano, hydroxy, amino, $C_{1-6}$-alkylamino, di($C_{1-6}$-alkyl)amino or $C_{1-6}$-acylamino;

A is (i) —O—, —S—, —$SO_2$— or —NH—; (ii) a $C_{1-4}$-alkyl-substituted nitrogen atom, or (iii) a $C_{1-8}$-alkylene chain or a heteroalkylene chain having 2 to 8 chain atoms, which optionally contains one or more unsaturations, wherein $C_{1-8}$-alkylene and heteroalkylene may be independently substituted in one or more positions by $C_{1-4}$-alkyl or oxo, and wherein two juxtaposed or spaced chain atoms in $C_{1-8}$-alkylene or heteroalkylene optionally are joined through an alkylene bridge having 1 to 5 chain carbon atoms or a heteroalkylene bridge having 2 to 5 chain atoms, or two spaced chain atoms in $C_{1-8}$-alkylene or heteroalkylene optionally are joined through a bridging bond, to form a saturated or partially or fully unsaturated carbocyclic or heterocyclic ring having 3 to 8 ring members;

B is —$C(R_4)(R_5)$—, —$OC(R_4)(R_5)$—, —$N(R_6)C(R_4)(R_5)$—, —$N(R_6)$—, —O—, —S— or —$SO_2$—;

R is $C_{3-8}$-cycloalkyl, aryl or heteroaryl, each of which may be substituted in one or more positions independently of each other by $C_{1-6}$-alkyl, $C_{1-6}$-alkoxy, fluoro-$C_{1-6}$-alkoxy, 2,2,2-trifluoroethoxy, $C_{3-5}$-alkynyloxy, $C_{3-5}$-alkenyloxy, dimethylamino-$C_{1-6}$-alkoxy, methylamino-$C_{1-6}$-alkoxy, $C_{1-6}$-alkylthio, fluoromethyl, difluoromethyl, trifluoromethyl, fluoromethylthio, difluoromethoxy, difluoromethylthio, trifluoromethoxy, trifluoromethylthio, halogen, hydroxy, nitro, cyano, trifluoromethylsulphonyloxy, $C_{1-6}$-alkylsulphonamido, $C_{2-6}$-alkenyl, $C_{2-6}$-alkynyl, $C_{1-6}$-acyl, $C_{1-6}$-alkylcarbonyl-$C_{1-6}$-alkyl, $C_{1-6}$-alkylsulphonyl, $C_{1-6}$-alkylsulphonyloxy, $C_{1-6}$-alkoxy-$C_{1-6}$-alkyl, $C_{1-6}$-alkoxycarbonyl, $C_{1-6}$-alkoxycarbonyl-$C_{1-6}$-alkyl, $C_{1-6}$-acyloxy-$C_{1-6}$-alkyl, hydroxy-$C_{1-6}$-alkyl, hydroxy-$C_{1-6}$-alkoxy, $C_{1-6}$-alkoxy-$C_{1-6}$-alkoxy, $C_{1-6}$-alkoxy-$C_{1-6}$-alkylthio, hydroxy-$C_{1-6}$-alkylthio, heteroaryl-$C_{1-6}$-alkylthio, aryl-$C_{1-6}$-alkylthio, $C_{1-6}$-alkoxy-$C_{1-6}$-alkylamino, N—($C_{1-6}$-alkoxy-$C_{1-6}$-alkyl)-N-methylamino, $C_{3-6}$-cycloalkyl-$C_{1-6}$-alkoxy, aryl-$C_{1-6}$-alkoxy, heterocyclyl-$C_{1-6}$-alkoxy, $C_{3-8}$-cycloalkyl, $C_{3-8}$-cycloalkyloxy, aryl, aryloxy, arylthio, arylsulphonyl, aryl-$C_{1-6}$-acyl, aryl-$C_{1-6}$-alkyl, aryl-$C_{2-6}$-alkenyl, aryl-$C_{2-6}$-alkynyl, heterocyclyl-$C_{1-6}$-alkyl, heterocyclyl-$C_{2-6}$-alkenyl, heterocyclyl-$C_{2-6}$-alkynyl, heterocyclyl, heterocyclyloxy, heterocyclylthio, heterocyclylsulphonyl, heterocyclylamino, heterocyclyl-$C_{1-6}$-acyl, —$N(R_2)(R_3)$, —$CON(R_7)(R_8)$ or, when R is optionally substituted $C_{3-8}$-cycloalkyl, oxo, wherein any cycloalkyl, aryl and heterocyclyl residues as substituents on $C_{3-8}$-cycloalkyl, aryl or heteroaryl or as part of substituents on $C_{3-8}$-cycloalkyl, aryl or heteroaryl in turn may be substituted in one or more positions independently of each other by $C_{1-4}$-alkyl, $C_{1-4}$-alkoxy, methanesulphonamido, $C_{1-4}$-alkylthio, $C_{1-4}$-alkylsulphonyl, $C_{1-4}$-acyl, heterocyclyl, heterocyclyloxy, heterocyclylthio, aryloxy, arylthio, fluoromethyl, trifluoromethyl, trifluoromethoxy, trifluoromethylthio, halogen, hydroxy, nitro, cyano, $N(R_2)(R_3)$ or, for $C_{3-8}$-cycloalkyl and partially or fully saturated heterocyclyl, oxo or hydroxy;

$R_1$ is (i) a saturated or unsaturated azacyclic or aminoazacyclic ring, or a saturated diazacyclic or aminodiazacyclic ring, which has 4 to 7 ring members, or a saturated aminoazabicyclic, azabicyclic or diazabicyclic ring which has 7 to 10 ring members, which mono- or bicyclic rings may be mono- or disubstituted in one or more positions independently of each other by, preferably bound to a carbon atom. $C_{1-4}$-alkyl, $C_{1-4}$-alkoxy, fluoromethyl, trifluoromethyl, difluoromethyl, hydroxymethyl or methoxymethyl or —$N(R_6)_2$, or, preferably bound to a ring nitrogen atom, hydroxy, 2-hydroxyethyl or 2-cyanoethyl, or, bound to a ring nitrogen atom, $C_{1-6}$-acyl, $C_{1-4}$-alkoxycarbonyl or tetrahydropyran-2-yl, and wherein a saturated azacyclic ring may contain a further heteroatom selected from oxygen and sulphur; or (ii) a group —[$C(R_4)(R_5)]_xN(R_{2a})(R_{3a})$;

$R_2$ and $R_3$ independently of each other are hydrogen, $C_{1-6}$-alkyl, $C_{1-6}$-acyl, —$CON(R_7)(R_8)$, aryl, heterocyclyl, aryl-$C_{1-6}$-alkyl, heterocyclyl-$C_{1-6}$-alkyl, aryl-$C_{1-6}$-acyl or heterocyclyl-$C_{1-6}$-acyl, wherein any aryl and heterocyclyl residues in turn may be substituted in one or more positions independently of each other by halogen, $C_{1-4}$-alkyl, $C_{1-4}$-alkoxy, $C_{1-4}$-alkylthio, $C_{1-4}$-alkylsulphonyl, methanesulphonamido, nitro, cyano, hydroxy, trifluoromethyl, trifluoromethoxy, trifluoromethylthio or —$N(R_2)(R_3)$; or $R_2$ and $R_3$ together with the nitrogen atom to which they are bound form a saturated heterocyclic ring having 4–7 ring members and optionally containing a further heteroatom, which ring may be substituted by $C_{1-6}$-alkyl, $C_{1-6}$-alkoxy, oxo or hydroxy;

$R_{2a}$ and $R_{3a}$ independently of each other are hydrogen, methyl or ethyl, or $R_{2a}$ and $R_{3a}$ together with the nitrogen atom to which they are bound form a pyrrolidine, piperazine, morpholine, thiomorpholine or piperidine ring;

$R_4$ and $R_5$ independently of each other, and independently on each substituted carbon atom, are hydrogen or $C_{1-6}$-alkyl;

$R_6$ is hydrogen or $C_{1-6}$-alkyl;

$R_7$ and $R_8$ independently of each other are hydrogen, $C_{1-6}$-alkyl, aryl, heteroaryl, aryl-$C_{1-4}$-alkyl or heteroaryl-$C_{1-4}$-alkyl, wherein aryl and heteroaryl residues in turn may be substituted in one or more positions independently of each other by halogen, $C_{1-6}$-alkyl, $C_{1-6}$-alkoxy, $C_{1-6}$-alkylthio, $C_{1-6}$-alkylsulphonyl, methanesulphonamido, nitro, cyano, hydroxy, trifluoromethyl, trifluoromethoxy, trifluoromethylthio or —N($R_2$)($R_3$); or $R_7$ and $R_8$ together with the nitrogen atom to which they are bound form a saturated heterocyclic ring having 4–7 ring members and optionally containing a further heteroatom;

n is 0 or 1; and x is 2, 3 or 4;

with the proviso that (i) when —A—R is phenoxy or phenylthio, then Ar is other than quinoxalinyl or pyridyl, and (ii) when A is ethenylene, then Ar is other than quinoxalinyl;

and pharmaceutically acceptable salts, hydrates, geometrical isomers, tautomers, optical isomers, N-oxides and prodrug forms thereof.

A limited group of compounds of the invention comprise compounds of formula (I) as defined above but with the further proviso that when Ar is optionally substituted phenyl, pyridyl or quinoxalinyl, then A is a group -Het—CH($R_6$)—CH($R_6$)—Het-, where each Het independently is selected from O, S and N($R_6$), and $R_6$ is as defined above.

In case the compounds of formula (I) can be in the form of optical isomers, the invention comprises the racemic mixture as well as the individual enantiomers as such.

In case the compounds of formula (I) contain groups which may exist in tautomeric forms, the invention comprises the tautomeric forms of the compounds as well as mixtures thereof, e.g. a 2-hydroxypyridine and its tautomer 1H-2-pyridone.

In case the compounds of formula (I) can be in the form of geometrical isomers, the invention comprises the geometrical isomers as well as mixtures thereof.

In another aspect, the invention provides the compounds according to formula (I) above for use in therapy.

Still another aspect of the invention provides a pharmaceutical composition comprising a compound according to formula (I) above as the active ingredient, preferably together with a pharmaceutically acceptable carrier and, if desired, other pharmacologically active agents.

In yet another aspect, the invention provides a method for the treatment of a human or animal subject suffering from a serotonin-related disease, particularly 5-HT2 receptor-related, especially eating disorders, particularly obesity; memory disorders, schizophrenia, mood disorders, anxiety disorders, pain, sexual dysfunctions, and urinary disorders.

Another aspect of the invention provides the use of the compounds according to formula (I) above for the manufacture of a medicament for the treatment of a serotonin-related disease, particularly 5-HT$_2$ receptor-related, especially eating disorders, particularly obesity; memory disorders; schizophrenia, mood disorders, anxiety disorders, pain, sexual dysfunctions, and urinary disorders.

Still another aspect of the invention provides methods for the preparation of the compounds according to formula (I) above.

DETAILED DESCRIPTION OF THE INVENTION

First, the various terms used, separately and in combinations, in the above definition of the compounds having the general formula (I) will be explained.

By "heteroatom" is meant nitrogen, oxygen, sulphur, and in heterocyclic rings (including heteroaromatic as well as saturated and partially saturated heterocyclic rings), also selenium.

The term "aryl" is intended to include aromatic rings (monocyclic or bicyclic) having from 6 to 10 ring carbon atoms, such as phenyl, naphthyl and 1,2,3,4-tetrahydronaphthyl (substitutions may be in any ring).

The term "heteroaryl" means a monocyclic, bi- or tricyclic aromatic ring system (only one ring need to be aromatic, and substitutions may be in any ring) having from 5 to 14, preferably 5 to 10 ring atoms (mono- or bicyclic), in which one or more of the ring atoms are other than carbon, such as nitrogen, sulphur, oxygen and selenium. Examples of such heteroaryl rings are pyrrole, imidazole, thiophene, furan, thiazole, isothiazole, thiadiazole, oxazole, isoxazole, oxadiazole, pyridine, pyrazine, pyrimidine, pyridazine, pyrazole, triazole, tetrazole, chroman, isochroman, coumarin, quinoline, quinoxaline, isoquinoline, phthalazine, cinnoline, quinazoline, indole, isoindole, indoline, isoindoline, benzothiophene, benzofuran, 2,3-dihydrobenzofuran, isobenzofuran, benzoxazole, 2,1,3-benzoxadiazole, benzothiazole, 2,1,3-benzothiadiazole, 2,1,3-benzoselenadiazole, benzimidazole, indazole, 2,3-dihydro-1,4-benzodioxine, indane, 1,3-benzodioxole, 1,2,3,4-tetrahydroquinoline, 3,4-dihydro-2H-1,4-benzoxazine, 1,5-naphthyridine, 1,8-naphthyridine, acridine, fenazine, xanthene, 3,4-dihydro-2H-pyrido[3,2-b]-1,4-oxazine, and 2,3-dihydro-1,4-benzoxathiine. The heteroaryl ring may be linked to the divalent group A in formula (I) via a carbon or nitrogen atom thereof. If a bi- or tricyclic ring is substituted, it may be substituted in any ring.

The term "heteroalkylene" means an alkylene group which contains a terminal heteroatom at one or both ends and/or one or more carbon chain-interrupting heteroatom(s) selected from N, O and S. The number of heteroatoms is at least one, and usually from one to three, especially one or two. When heteroalkylene is substituted, it is usually substituted at a carbon atom by $C_{1-4}$-alkyl or oxo, but it may alternatively or additionally be substituted at a nitrogen by $C_{1-4}$-alkyl or at a sulphur atom by oxo (S=O or O=S=O), if present.

The term "heterocyclyl" is intended to include fully unsaturated (i.e. aromatic) as well as partially and fully saturated mono-, bi- and tricyclic rings having from 4 to 14, preferably 4 to 10 ring atoms, and containing one or more heteroatoms selected from oxygen, sulphur and nitrogen, such as, for example, the heteroaryl groups mentioned above as well as their corresponding partially saturated or fully saturated heterocyclic rings. Exemplary saturated heterocyclic rings are azetidine, pyrrolidine, piperidine, piperazine, morpholine and thiomorpholine.

$C_{1-6}$-alkyl, which may be straight or branched, is preferably $C_{1-4}$-alkyl. Exemplary alkyl groups include methyl, ethyl, propyl, isopropyl, butyl, sec-butyl, tert-butyl, pentyl, isopentyl, hexyl, and isohexyl.

$C_{1-6}$-alkoxy, which may be straight or branched, is preferably $C_{1-4}$-alkoxy. Exemplary alkoxy groups include methoxy, ethoxy, propoxy, isopropoxy, butoxy, sec-butoxy, tert-butoxy, pentyloxy, isopentyloxy, hexyloxy, and isohexyloxy.

$C_{2-6}$-alkenyl, which may be straight or branched, is preferably $C_{2-4}$-alkenyl, e.g. 1-propenyl, 2-propenyl, vinyl.

$C_{2-6}$-alkynyl, which may be straight or branched, is preferably $C_{2-4}$-alkynyl, e.g. propargyl, ethynyl.

$C_{3-8}$-cycloalkyl is preferably $C_{4-7}$-cycloalkyl. Exemplary cycloalkyl groups include cyclopropyl, cyclobutyl, cyclopentyl, cyclohexyl, cycloheptyl and cyclooctyl.

$C_{1-6}$-acyl may be saturated or unsaturated and is preferably $C_{1-4}$-acyl. Exemplary acyl groups include formyl, acetyl, propionyl, butyryl, isobutyryl, valeryl, isovaleryl, butenoyl (e.g. 3-butenoyl), hexenoyl (e.g. 5-hexenoyl).

$C_{1-8}$-alkylene (wherein 1–8 is the number of chain carbon atoms) and heteroalkylene having 2 to 8 chain atoms, which may contain one or more unsaturations (double and/or triple bonds), are preferably $C_{1-4}$-alkylene and heteroalkylene of 2 to 4 chain atoms, respectively. Exemplary alkylene groups include methylene, ethylene, propylene, butylene and their isomers (e.g. 1,3-butlene, 2-methyl-1,3-propylene). Exemplary heteroalkylene groups include oxymethylene (and methylenoxy), oxyethylene (and ethylenoxy), oxypropylene (and propylenoxy), oxybutylene (and butylenoxy), ethylenedioxy, propylenedioxy, butylenedioxy, oxyallyl (and allyloxy), etc. An exemplary alkyl-substituted heteroalkylene group is methylethylenedioxy.

Hydroxy-$C_{1-6}$-alkyl may be straight or branched. Exemplary hydroxyalkyl groups include hydroxymethyl, 1-hydroxyethyl, 2-hydroxyethyl, 2-hydroxypropyl, 3-hydroxypropyl, 2-hydroxybutyl, 3-hydroxybutyl, 4-hydroxybutyl.

Exemplary aryl-$C_{1-6}$-acyl groups include benzoyl, 1-naphthoyl, 2-naphthoyl, cinnamoyl and phenylacetyl.

Exemplary $C_{1-6}$-alkylcarbonyl-$C_{1-6}$-alkyl groups include 2-oxobutyl.

Exemplary $C_{1-6}$-alkoxy-$C_{1-6}$-alkyl groups include 2-ethoxyethyl.

Exemplary $C_{1-6}$-alkoxycarbonyl-$C_{1-6}$-alkyl groups include ethoxycarbonylbutyl.

Exemplary $C_{1-6}$-acyloxy-$C_{1-6}$-alkyl groups include propanoyloxypropyl.

Exemplary saturated and unsaturated (partially and fully) azacyclic and saturated azabicyclic rings include azetidine, pyrrolidine, piperidine, morpholine, hexahydroazepine, tetrahydropyridine, pyridine and 1-azabicyclo[2.2.2]octane. The azacyclic and azabicyclic rings are coupled via a ring carbon atom when n=0.

Exemplary saturated and unsaturated aminoazacyclic rings include aminopiperidine (e.g. 4-aminopiperidine), aminoazetidine (e.g. 3-aminoazetidine), aminopyrrolidine (e.g. 3-aminopyrrolidine), and aminopyridine (e.g. 4-aminopyridine). The aminoazacyclic rings are preferably coupled to B or Ar in formula (I) via either the aza nitrogen atom or the amino nitrogen atom. An example of a saturated aminoazabicyclic ring is 3-aminoazabicyclo[2.2.2]octane, and the coupling is preferably via the 3-amino nitrogen atom.

An example of a saturated aminodiazacyclic ring is 1-aminopiperazine, and the coupling is preferably via either the 4-aza nitrogen atom or the 1-amino nitrogen atom.

Exemplary saturated diazacyclic rings include piperazine and homopiperazine, and an example of a diazabicyclic ring is diazabicyclo[2.2.1]heptane. The diazacyclic and diazabicyclic rings are preferably coupled via one of the ring nitrogens.

The group $-[C(R_4)(R_5)]_xN(R_{2a})(R_{3a})$ is preferably linked to Ar in formula (I) via a heteroatom (i.e. when n=1 and B is oxygen, nitrogen or sulphur).

As indicated by the expression "independently for each substituted carbon atom" with regard to substituents $R_4$ and $R_5$, each individual carbon atom in the chain $-[C(R_4)(R_5)]_x-$ may be differently substituted than the adjacent carbon atom(s). An exemplary chain, werein x=3, illustrating this is $-CH(CH_3)-CH_2-C(CH_3)(CH_3)-$.

Halogen includes fluorine, chlorine, bromine and iodine.

Where it is stated above that aryl, heteroaryl and heterocyclyl residues may be substituted, this applies to aryl, heteroaryl and heterocyclyl per se as well as to any combined groups containing aryl, heteroaryl or heterocyclyl residues, such as aryl-$C_{1-6}$-acyl, heteroaryl-$C_{2-4}$-alkenyl, heterocyclylthio, etc.

The term "N-oxides" means that one or more nitrogen atoms, when present in a compound, are in N-oxide form (N→O).

The term "prodrug forms" means a pharmacologically acceptable derivative, such as an ester or an amide, which derivative is biotransformed in the body to form the active drug. Reference is made to Goodman and Gilman's, The Pharmacological basis of Therapeutics, $8^{th}$ ed., McGraw-Hill, Int. Ed. 1992, "Biotransformation of Drugs, p. 13–15.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Pharmaceutically acceptable salts" mean salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, toluenesulphonic acid, methanesulphonic acid, trifluoroacetic acid, fumaric acid, succinic acid, tartaric acid, citric acid, benzoic acid, ascorbic acid and the like.

"A" in formula I is preferably a $C_{2-8}$-alkylene chain or a heteroalkylene chain having at least two chain atoms.

More preferably, "A" in formula I is a divalent group of the general formula (II):

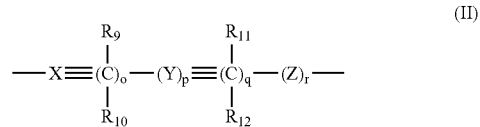

wherein $R_9$, $R_{10}$, $R_{11}$ and $R_{12}$ independently of each other, and independently for each substituted carbon atom, are hydrogen, $C_{1-4}$-alkyl, trifluoromethyl or oxo;

X is $-C(R_{13})(R_{14})-$, $-O-$, $-S-$, $-SO_2-$ or $-N(R_{15})-$;

Y is independently $-C(R_{16})(R_{17})-$, $-O-$, $-S-$, $-SO_2-$ or $-N(R_{15})-$;

Z is independently $-C(R_{18})(R_{19})-$, $-O-$, $-S-$, $-SO_2-$ or $-N(R_{15})-$;

$R_{13}$, $R_{14}$, $R_{16}$, $R_{17}$, $R_{18}$ and $R_{19}$, independently of each other, and independently for each substituted carbon atom, are hydrogen, $C_{1-4}$-alkyl or trifluoromethyl or oxo; or two of $R_{13}$, $R_{14}$, $R_{16}$, $R_{17}$, $R_{18}$ and $R_{19}$ together represent an interconnecting bond or an alkylene bridge of 1 to 5 chain carbon atoms or a heteroalkylene bridge of 2 to 5 chain atoms to form, together with the atom(s) to which they are bound, a cyclic structure having 3–8 ring members;

$R_{15}$ is hydrogen, $C_{1-4}$-alkyl or $C_{1-6}$-acyl;

o, p, q and r independently of each other are 0 to 3; and the four broken lines independently of each other represent an optional carbon—carbon bond;

with the provisos (i) that A does not contain two juxtaposed heteroatoms O or S in an open chain, and (ii) that o, p, q and r together are not more than 8.

The expression "independently for each substituted carbon atom" means that if in formula (II) the integers o and/or g are 2 or 3, each carbon atom in question may be differently substituted. Thus, in the case of $R_9$ and $R_{10}$, for example, if o is 2 or 3, for each of the two or three carbons atoms, the meanings of $R_9$ and $R_{10}$ may be chosen independently of the meanings for $R_9$ and $R_{10}$ on the other two or three carbon atoms. For example, when o=2, the coupling to X is via a single bond, and $R_9$ and $R_{10}$ are independently selected from hydrogen and methyl, then e.g. $R_9$ may be hydrogen and $R_{10}$ methyl on the first carbon atom and both $R_9$ and $R_{10}$ may be hydrogen on the second carbon atom. i.e. the group 1-methylethylene. If $R_9$ and $R_{10}$ on the first carbon atom are hydrogen and, on the second carbon atom $R_9$ is hydrogen and $R_{10}$ is methyl, the group 2-methylethylene is obtained. Exemplary groups for o=3, when $R_9$ and $R_{10}$ are independently selected from e.g. hydrogen, methyl and oxo, are 2-oxo-1,3-butanediyl, 1-oxo-2-methyl-1, 3-propanediyl, 1-oxo-1,3-butanediyl and 1-oxo-2-methyl-1,3-butanediyl. The corresponding applies, of course, also to Y and Z in formula (II) when Y and Z are other than —O— or —S— and the integers p and r, respectively, are 2 or 3.

When formula (II) contains a carbon—carbon double bond(s) and/or a triple bond(s), one or both substituents on each participating carbon atom is, of course, omitted (for double bonds: $R_9$ and $R_{13}$ and/or $R_{11}$ and $R_{16}$, respectively; and for triple bonds: $R_9$, $R_{10}$, $R_{13}$ and $R_{14}$ and $R_{11}$, $R_{12}$, $R_{16}$ and $R_{17}$, respectively).

In a preferred embodiment, A in formula (I) is a group -Het—CH($R_6$)—CH($R_6$)—Het-, where each Het independently is selected from O, S and N($R_6$), and $R_6$ is as defined above, preferably hydrogen or methyl, particularly hydrogen.

The presently most preferred group A is —O—CH$_2$—CH$_2$—O—. Other preferred groups A include —S—CH$_2$—CH$_2$—O—, —O—CH$_2$—CH$_2$—S—, and —O—CH$_2$—CH$_2$—.

In another preferred embodiment, A is —O—CH$_2$— and R is optionally substituted heteroaryl, e.g. 2,3-dihydro-1,4-benzodioxine, 3,4-dihydro-2H-1,4-benoxazine, 2,3-dihydro-1,4-benzoxathiine, quinoline, benzofuran, 3,4-dihydro-2H-pyrido(3,2-b)-1,4-oxazine.

R in formula (I) is preferably optionally substituted aryl or heteroaryl. When R is aryl, it is preferably phenyl which is substituted or unsubstituted, preferably substituted. When R is substituted phenyl, it is preferably substituted in the meta-position. When R is heteroaryl, it is preferably selected from pyridine, isoquinoline, quinoline, quinoxaline, 2,3-dihydro-1,4-benzodioxine, benzoxazole, 2,1,3-benzothiadiazole, coumarin, 3,4-dihydro-2H-1,4-benzoxazine and quinazoline. Especially R is a substituted (especially meta-substituted) phenyl ring, or an unsubstituted or substituted pyridine ring.

Ar in formula (I) is preferably unsubstituted or substituted pyrazine, quinoxaline, 1,2,5-thiadiazole, pyridyl or phenyl.

When Ar is substituted it is usually mono- or (independently) di-substituted. Preferred substituents on Ar are selected from $C_{1-4}$-alkyl. $C_{1-4}$-alkoxy, $C_{1-4}$-alkylthio. $C_{1-4}$-alkylsulphonyl, cyano, hydroxy, $C_{2-4}$-alkenyl, $C_{2-4}$-alkynyl, trifluoromethyl, trifluoromethylthio, halogen, amino, methylamino, dimethylamino, acetamido, aryl, aryloxy, arylthio, heterocyclyl, heterocyclyloxy, heterocyclylthio, wherein any aryl and heterocyclyl residues in turn may be substituted in one or more positions independently of each other by halogen, methyl, methoxy, methylthio, methylsulphonyl, nitro, trifluoromethyl, cyano, hydroxy, amino, methylamino and dimethylamino or acetamido.

$R_1$ in formula (I) is preferably a saturated diazacyclic ring, especially piperazine, unsubstituted or substituted by $C_{1-4}$-alkyl, e.g. mono-substituted, particularly by methyl (at any position).

The integer n in formula (I) is preferably 0. When n=1, B is preferably —N($R_6$)—, —O—, —S— or —SO$_2$—, where $R_6$ is as defined above.

The integer o in formula (II) is preferably 2.
The integer p in formula (II) is preferably 1.
The integer q in formula (II) is preferably 0.
The integer r in formula (II) is preferably 0.
X, Y and Z are preferably oxygen.
$R_9$ to $R_{12}$ are preferably hydrogen.

In a preferred subgroup of compounds of formula I, Ar is a pyrazine ring, i.e. compounds of formula (Ia):

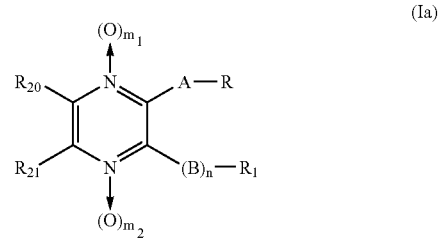

(Ia)

wherein $R_{20}$ and $R_{21}$ independently of each other are hydrogen, $C_{1-4}$-alkyl, $C_{1-4}$-alkoxy, $C_{1-4}$-alkylthio, $C_{1-4}$-acyl, $C_{1-4}$-alkylsulphonyl, cyano, nitro, hydroxy. $C_{2-4}$-alkenyl, $C_{2-4}$-alkynyl, trifluoromethyl, trifluoromethoxy, trifluoromethylthio, halogen, amino, dimethylamino, methylamino, acetamido, aryl, aryloxy, arylthio, heterocyclyl, heterocyclyloxy or heterocyclylthio, wherein any aryl and heterocyclyl residues in turn may be substituted in one or more positions independently of each other by halogen, methyl, methoxy, methylthio, methylsulphonyl, nitro, cyano, hydroxy, trifluoromethyl, amino, methylamino, dimethylamino or acetamido, or $R_{20}$ and $R_{21}$ together with the carbon atoms to which they are bound form a 5- or 6-membered aromatic or heteroaromatic ring, which optionally is independently substituted in one or more positions by halogen, methyl, methoxy, methylthio, methylsulphonyl, nitro, cyano, hydroxy, trifluoromethyl, trifluoromethylthio, amino, methylamino, dimethylamino or acetamido;

$m_1$ and $m_2$ are independently of each other 0 or 1; and
A, B, R, $R_1$ and n are as defined above.

When $R_{20}$ and $R_{21}$ in formula (Ia) form a 5- or 6-membered aromatic or heteroaromatic ring together with the pyrazine ring carbons, such a ring may, for example, be selected from the aryl and heteroaryl rings mentioned above.

$R_{20}$ and $R_{21}$ are preferably (independently) hydrogen, halogen or methyl. When $R_{20}$ and $R_{21}$ form a ring together with the ring carbons to which they are bound, such a ring is preferably benzene (to give quinoxaline) or thiophene (to give thieno[3,4-b]pyrazine). When substituted, the rings are preferably mono- or (independently) disubstituted, such as by halogen or methyl.

The integers $m_1$ and $m_2$ are preferably both zero (i.e. the pyrazine nitrogens are not in oxidized form).

A subgroup of the compounds of formula (Ia) consists of compounds of formula (Ib):

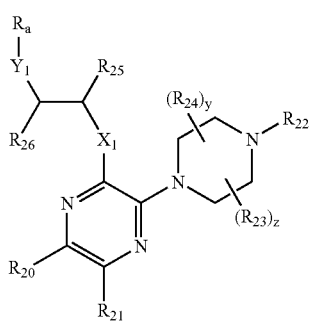

wherein:

$X_1$ and $Y_1$ independently are —O—, —S— or —N($R_{27}$)—;

$R_a$ is aryl or heteroaryl optionally substituted as defined for R in claim 1;

$R_{20}$ and $R_{21}$ are as defined in claim 11;

$R_{22}$ is hydrogen, hydroxy, $C_{1-4}$-alkyl, $C_{3-4}$-alkenyl, $C_{1-4}$-acyl, $C_{1-4}$-alkoxycarbonyl, 2-hydroxyethyl, 2-cyanoethyl or tetrahydropyran-2-yl;

$R_{23}$ and $R_{24}$ independently of each other are hydrogen, $C_{1-4}$-alkyl, hydroxymethyl, $C_{1-4}$-alkoxymethyl or fluoromethyl;

$R_{25}$ is hydrogen or $C_{1-4}$-alkyl;

$R_{26}$ is hydrogen, $C_{1-4}$-alkyl or is linked to a carbon atom in $R_a$ adjacent to the atom binding to $Y_1$ to form (together with the carbon atom to which it is bound, $Y_1$ and the two atoms in $R_a$) a 5- or 6-membered ring which may contain an additional heteroatom;

$R_{27}$ is hydrogen or $C_{1-4}$-alkyl, preferably methyl or ethyl; and y and z independently of each other are 1 or 2.

Exemplary ring systems formed when $R_{26}$ is linked to $R_a$ are 2,3-dihydro-1,4-benzodioxine 3,4-dihydro-2H-1,4-benzoxazine, 2,3-dihydro-1,4-benzoxathiine and benzofuran.

In formula (Ib), $R_{22}$ is preferably hydrogen, and $R_{23}$ and $R_{24}$ are preferably $C_{1-4}$-alkyl, especially methyl, or hydrogen. Particularly, $R_{23}$ is methyl (especially in the 2-position of the piperazine ring; and preferably with (R)-configuration at the chiral carbon atom), z is 1 and $R_{24}$ is hydrogen. When $R_{23}$ or $R_{24}$ are other than hydrogen and at least one of y and z is 2, or y and z both are I, then $R_{23}$ or $R_{24}$, respectively, may be on the same or different carbon atoms.

$R_{25}$ is preferably hydrogen.

Presently preferred compounds of the general formula (I) above are:

2-(2-Phenoxy)ethyl 3-(1-piperazinyl)-2-pyrazinyl ether
2-(2-Fluorophenoxy)ethyl 3-(1-piperazinyl)-2-pyrazinyl ether
2-(3-Cyanophenoxy)ethyl 3-(1-piperazinyl)-2-pyrazinyl ether
2-(3-Methoxyhenoxy)ethyl 3-(1-piperazinyl)-2-pyrazinyl ether
2-[3-(2-hydroxyethoxy)phenoxy]ethyl 3-(1-piperazinyl)-2-pyrazinyl ether
2,3-Dihydro-1,4-benzodioxin-2-ylmethyl 3-(1-piperazinyl)-2-pyrazinyl ether
2-(2-Methoxyphenoxy)ethyl 3-(1-piperazinyl)-2-pyrazinyl ether
2-(2,5-Difluorophenoxy)ethyl 3-(1-piperazinyl)-2-pyrazinyl ether
2-(3,5-Dimethoxyphenoxy)ethyl 3-(1-piperazinyl)-2-pyrazinyl ether
2-(3,4-Dihydro-2H-pyrido[3,2-b]-1,4-oxazin-2-ylmethoxy)-3-(1-piperazinyl)pyrazine
2-Methyl-1-[3-(2-phenoxyethoxy)-2-pyrazinyl]piperazine, particularly the (R)-enantiomer thereof
2-Methyl-1-{3-(2-(3-pyridinyloxy)ethoxy]-2-pyrazinyl}piperazine, particularly the (R)-enantiomer thereof
2-(Quinazolinyl-8-yloxy)ethyl 3-(1-piperazinyl)-2-pyrazinyl ether
2-(Isoquinolinyl-5-yloxy)ethyl 3-(1-piperazinyl)-2-pyrazinyl ether
2-[2-(3-Pyridinyloxy)ethoxy]-3-(1-piperazinyl)-6,7-difluoroquinoxaline
2-[2-(3-Pyridinyloxy)ethoxy]-3-(1-piperazinyl)thieno[3,4-b]pyrazine
2-(3,4-Dihydro-2H-1,4-benzoxazin-2-ylmethoxy)-3-(1-piperazinyl)pyrazine
2-Methyl-1-{3-[2-(2-amino-8-quinolinyloxy)ethoxy]-2-pyrazinyl}piperazine, particularly the (R)-enantiomer thereof
1-{3-[2-(2-Methoxy-3-pyridinyloxy)ethoxy]-2-pyrazinyl}piperazine
2-Methyl-1-{3-[2-(2-methoxy-3-pyridinyloxy)ethoxy]-2-pyrazinyl}piperazine, particularly the (R)-enantiomer thereof.
2-{2-[(2-Chloro-3-pyridinyl)oxy]ethoxy}-3-(1-piperazinyl)pyrazine,
2-{2-[(2-Ethoxy-3-pyridinyl)oxy]ethoxy}-3-(1-piperazinyl)pyrazine,
1-(3-{2-[(2-Ethoxy-3-pyridinyl)oxy]ethoxy}-2-pyrazinyl)-2-methylpiperazine, particularly the (R)-enantiomer thereof
2-(2-[{2-(Methylsulfanyl)-3-pyridinyl]oxy}ethoxy)-3-(1-piperazinyl)pyrazine.
2-Methyl-1-[3-(2-{[2-(methylsulfanyl)-3-pyridinyl]oxy}ethoxy)-2-pyrazinyl]piperazine particularly the (R)-enantiomer thereof,
2-{2-[(2-Bromo-3-pyridinyl)oxy]ethoxy}-3-(1-piperazinyl)pyrazine,
1-(3-{2-[(2-Bromo-3-pyridinyl)oxy]ethoxy}-2-pyrazinyl)-2-methylpiperazine, particularly the (R)-enantiomer thereof,
2-(1-Piperazinyl)-3-(2-{3-[2-(2-pyridinyl)ethoxy]phenoxy}ethoxy)pyrazine,
2-(2-{3-[2-(4-Methyl-1,3-thiazol-5-yl)ethoxy]phenoxy}ethoxy)-3-(1-piperazinyl)pyrazine,
2-(1-Piperazinyl)-3-{2-[3-(tetrahydro-3-furanylmethoxy)phenoxy]ethoxy}pyrazine,
2-(1-Piperazinyl)-3-{2-[3-(tetrahydro-3-furanyloxy)phenoxy]ethoxy}pyrazine,
1-{2-[3-(2-{[3-(1-Piperazinyl)-2-pyrazinyl]oxy}ethoxy)phenoxy]ethyl}-2-pyrrolidinone,
2-{2-[3-(2-Methoxyethoxy)phenoxy]ethoxy}-3-(1-piperazinyl)pyrazine,
2-{[3-(2-{[3-(1-Piperazinyl)-2-pyrazinyl]oxy}ethoxy)phenoxy]methyl}-benzonitrile,
2-(1-Piperazinyl)-3-{2-[3-(tetrahydro-2H-pyran-4-yloxy)phenoxy]ethoxy}-pyrazine,
N,N-Dimethyl-N-{2-[3-(2-{[3-(1-piperazinyl)-2-pyrazinyl]oxy}ethoxy)-phenoxy]-ethyl}amine,
7-(2-{[3-(1-Piperazinyl)-2-pyrazinyl]oxy}ethoxy)-2H-chromen-2-one,
1-(3-{2-[(2-Chloro-3-pyridinyl)oxy]ethoxy}-2-pyrazinyl)-2-methylpiperazine, particularly the (R)-enantiomer thereof, 7-Isoquinolinyl 2-{[3-(1-piperazinyl)]-2-pyrazinyl}oxy) ethyl ether,
2-(2-Chloro-4-methoxyphenoxy)ethyl 3-(1-piperazinyl)-2-pyrazinyl ether,
4-(2-{[3-(1-Piperazinyl)-2-pyrazinyl]oxy}ethoxy)-2-quinolinamine, and their pharmacologically acceptable salts and solvates.

As mentioned above, the compounds of the present invention are useful for the treatment (including prophylactic treatment) of serotonin-related disorders, especially 5-HT2 receptor-related, in a human being or in an animal (including e.g. pets), such as eating disorders, especially obesity; memory disorders, such as Alzheimer's disease; schizophrenia; mood disorders, including, but not restricted to, major depression and bipolar depression, including both mild and manic bipolar disorder, seasonal affective disorder (SAD): anxiety disorders, including situational anxiety, generalised anxiety disorder, primary anxiety disorders (panic disorders, phobias, obsessive-compulsive disorders, and post-traumatic stress disorders), and secondary anxiety disorders (for example anxiety associated with substance abuse); pain; sexual dysfunctions; and urinary disorders, such as urinary incontinence.

The compounds of the present invention in labelled form, e.g. isotopically labelled, may be used as a diagnostic agent.

The compounds of the general formula (I) above may be prepared by, or in analogy with, conventional methods, and especially according to or in analogy with the following methods.

Method A:

Compounds of formula (I) above in which A is bound to Ar via an O, S or N atom in A, and (i) n=0 and $R_1$ is a saturated aminoazacyclic, aminodiazacyclic, diazacyclic or diazabicyclic residue, or (ii) n=1, B is —N($R_6$)— or —N($R_6$)C($R_4$)($R_5$)—, wherein $R_4$, $R_5$ and $R_6$ are as defined above, and $R_1$ is a saturated or unsaturated azacyclic, or a saturated azabicyclic, residue, are prepared by reacting a compound of the structural formula (III):

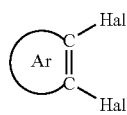

(III)

wherein Ar is as defined above and Hal is halogen, with a compound R—A'—X'—H or its corresponding anion where X' is —O—, —S— or —N($R_{15}$)—, A' is $C_{1-8}$-alkylene wherein the carbon chain may be interrupted by one or more heteroatoms and which may have a terminal heteroatom binding to R, said heteroatoms being selected from N, O and S, and R and $R_{15}$ are as defined above, to produce a compound of the formula (IV):

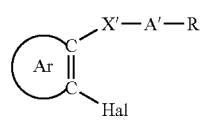

(IV)

wherein Ar, X', A', R and Hal are as defined above. The compound R—A'—X'—H may be converted completely or partially to its corresponding anion by treatment with bases, such as triethylamine, 1,8-diazabicyclo[5.4.0]undec-7-ene, $K_2CO_3$, NaOH, NaH, KO-t-Bu, lithium diisopropylamide or the like. The reaction is carried out in a solvent, such as dioxane, tetrahydrofuran or N,N-dimethylformamide (DMF), at 0–200° C. for 1–24 hours. The compound of formula (IV) is reacted with 1 to 10 molar equivalents of the appropriate amine in a solvent, such as acetonitrile, dioxane, tetrahydrofuran, n-butanol, DMF, or in a mixture of solvents such as DMF/dioxane, optionally in the presence of a base, such as $K_2CO_3$, $Na_2CO_3$, $Cs_2CO_3$, NaOH, triethylamine, pyridine or the like, at 0–200° C. for 1–24 hours to produce the compound of formula (I).

Exemplary amines have the following structures:

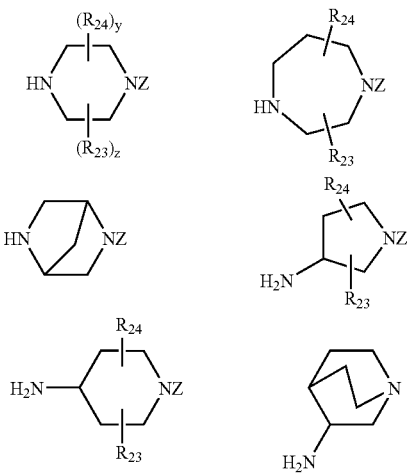

wherein $R_{23}$, $R_{24}$, y and z are as defined above, and Z has the meanings defined for $R_{22}$ in formula (Ib) above or is a suitable protecting group such as tert-butoxycarbonyl, trityl or benzyl.

Method B:

Compounds of formula (I) in which n=1, B is oxygen, sulphur and $R_1$ is a saturated azacyclic or azabicyclic residue, or a group —[C($R_4$)($R_5$)]$_x$ ($R_{2a}$)($R_{3a}$), wherein $R_2$, $R_3$, $R_4$, $R_5$ and x are as defined above, are prepared by reacting a compound of formula (IV) above with a corresponding hydroxy- or mercapto-substituted azacyclic or azabicyclic compound, or with a compound HO—$R_1$ or HS—$R_1$, where $R_1$ is —[C($R_4$)($R_5$)]$_x$N($R_{2a}$)($R_{3a}$). Exemplary hydroxy- and mercapto-substituted compounds have the following structures:

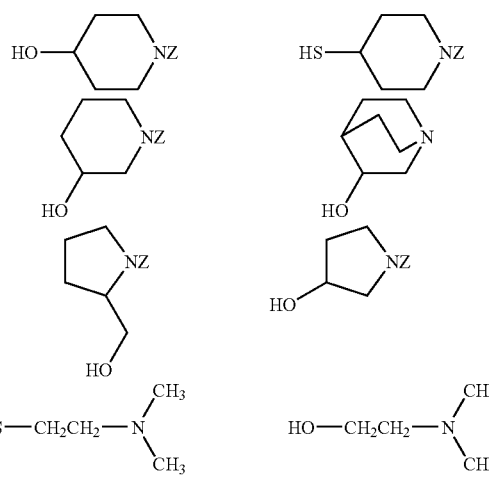

wherein Z is as defined above.

The reaction is carried out in a solvent, such as toluene, DMF or dioxane, in the presence of a base, such as 1,8- diazabicyclo[5.4.0]undec-7-ene, KOH, KO-t-Bu, NaH or the like, at 0–200° C. for 1–24 hours.

Method C:

Compounds of formula (I), wherein A is bound to R via an oxygen or sulphur atom in A, are prepared by reacting a compound of formula (V):

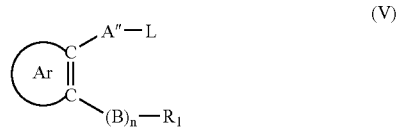

(V)

wherein Ar, $R_1$, B and n are as defined above, A″ is $C_{1-8}$-alkylene wherein the carbon chain may be interrupted by one or more heteroatoms and which may have a terminal heteroatom bound to Ar, said heteroatoms being selected from N, O and S, and L is a hydroxy, thiol or a leaving group such as, for example, halogen, tosyloxy, mesyloxy and the like, with a compound R—OH or R—SH, where R is as defined above, to produce the compound of formula (I).

When L is a free hydroxy or thiol group, the reaction may be carried out in the presence of diethyl azodicarboxylate (DEAD) or 1,1′-azobis(N,N-dimethylformamide) (cf. Tetrahedron Lett. 1995, 36, 3789–3792), preferably DEAD, and triphenylphosphine (PPh$_3$) in a solvent such as tetrahydrofuran or dichloromethane (Mitsunobu reaction, see Org. React. 1992, 42, 335–656).

When L is a leaving group, the reaction may be carried out in the presence of a suitable base, such as $Na_2CO_3$, $K_2CO_3$, $Cs_2CO_3$, KOH, triethylamine, 1,8-diazabicyclo[5.4.0] undec-7-ene or the like, in a solvent, such as acetonitrile or DMF, at 0–200° C. for 1–24 hours.

In case the group —(B)$_n$R$_1$ in formula (V) contains a primary or secondary amino group, the nitrogen may be protected with a suitable protecting group, preferably tert-butoxycarbonyl, trityl or benzyl. N-Deprotection is then carried out by conventional methods such as those described in Protective Groups in Organic Synthesis, John Wiley & Sons. 1991.

Method D:

Compounds of formula (I), in which A is bound to Ar via an O, S or N atom in A, and wherein n=0, or n=1 and B is oxygen, nitrogen, sulphur, —N(R$_6$)C(R$_4$)(R$_5$)—, wherein R$_4$, R$_5$ and R$_6$ are as defined above, are prepared by reacting a compound of formula (III) above with an appropriate amine, or an appropriate hydroxy- or mercapto-substituted compound to produce a compound of formula (VI):

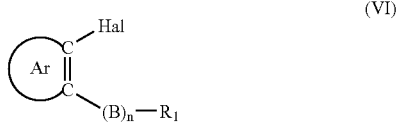

(VI)

wherein Ar, B, R$_1$, Hal and n are as defined above. The reaction conditions may be those described for methods A and B above. The compound of formula (VI) is reacted with a compound R—A′—X′—H or its corresponding anion, where X′ is —O—, —S— or —N(R$_{15}$)— A′ is $C_{1-8}$-alkylene wherein the carbon chain may be interrupted by one or more heteroatoms and which may have a terminal heteroatom binding to R, said heteroatoms being selected from N, O and S, and R and R$_{15}$ are as defined above, to produce a compound of the formula (I).

The reaction conditions may be those described for method A above.

Exemplary amines, hydroxy- and mercapto-substituted compounds include those shown in connection with methods A and B above as well as a compound HO—R$_1$ or HS—R$_1$, where R$_1$ is —[C(R$_4$)(R$_5$)]$_x$N(R$_{2a}$)(R$_{3q}$), and wherein R$_2$, R$_3$, R$_4$, R$_5$ and x re as defined above.

Compounds of formula (I), in which Ar represents an optionally substituted phenyl, naphthyl, pyridyl, or quinolinyl nucleus and (i) A is oxygen or (ii) A is bound to Ar via an oxygen atom in A, may be prepared by methods well known in the art, as illustrated in Examples 184 and 185 below.

An obtained compound of formula (I) may be converted to another compound of formula (I) by methods well known in the art (illustrated in e.g. Example 216).

The processes described above may be carried out to give a compound of the invention in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are maleic acid, fumaric acid, succinic acid, methanesulfonic acid, trifluoroacetic acid, acetic acid, oxalic acid, benzoic acid, hydrochloric acid, sulphuric acid, phosphoric acid, and the like.

The compounds of formula (I) may possess one or more chiral carbon atoms, and they may therefore be obtained in the form of optical isomers, e.g. as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The necessary starting materials for preparing the compounds of formula (I) are either known or may be prepared in analogy with the preparation of known compounds. For example, the aryloxy- and heteroaryloxyethanols used in the preparation of the novel compounds of formula (I) may be prepared using the methods depicted in Scheme 1 below.

Scheme 1

Preparation of some starting materials

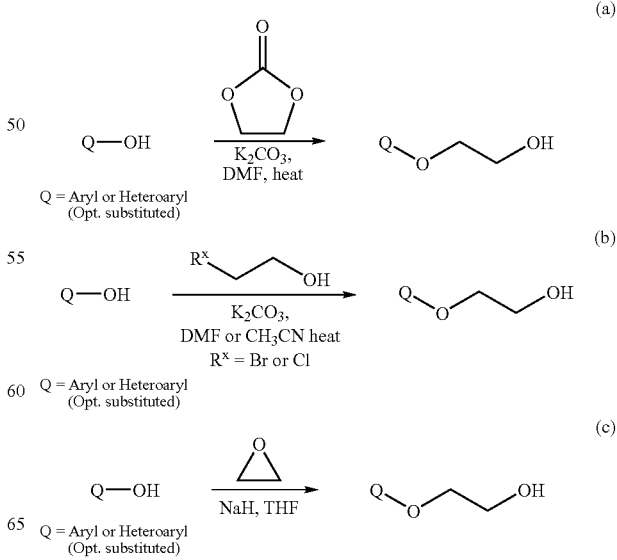

(d)

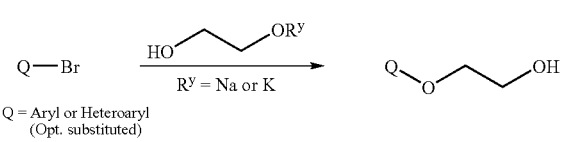

Q = Aryl or Heteroaryl
(Opt. substituted)

In accordance with the present invention, the compounds of formula (I), in the form of free bases or salts with physiologically acceptable acids, can be brought into suitable galenic forms, such as compositions for oral use, for injection, for nasal spray administration or the like, in accordance with accepted pharmaceutical procedures. Such pharmaceutical compositions according to the invention comprise an effective amount of the compounds of formula (I) in association with compatible pharmaceutically acceptable carrier materials, or diluents, as are well known in the art. The carriers may be any inert material, organic or inorganic, suitable for enteral, percutaneous, subcutaneous or parenteral administration, such as: water, gelatin, gum arabicum lactose, microcrystalline cellulose, starch, sodium starch glycolate, calcium hydrogen phosphate, magnesium stearate, talcum, colloidal silicon dioxide, and the like. Such compositions may also contain other pharmacologically active agents, and conventional additives, such as stabilizers, wetting agents, emulsifiers, flavouring agents, buffers, and the like.

The compositions according to the invention can e.g. be made up in solid or liquid form for oral administration, such as tablets, pills, capsules, powders, syrups, elixirs, dispersable granules, cachets, suppositories and the like, in the form of sterile solutions, suspensions or emulsions for parenteral administration, sprays, e.g. a nasal spray, transdermal preparations, e.g. patches, and the like.

As mentioned above, the compounds of the invention may be used for the treatment of serotonin-related disorders in a human being or an animal, such as eating disorders, particularly obesity, memory disorders, schizophrenia, mood disorders, anxiety disorders, pain, sexual dysfunctions, and urinary disorders. The compounds may also be useful for treating gastrointestinal disorders, such as gastrointestinal mobility disorders, e.g. irritable bowel syndrome (IBS), or glaucoma. The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

The invention will now be further illustrated by the following non-limiting Examples.

EXAMPLES

General:

The structures of the prepared compounds were confirmed by standard spectroscopical methods, and elemental analysis and/or high resolution MS. The NMR data were obtained on a JEOL JNM-EX 270, a Bruker 400 DPX or a Bruker DRX 500 spectrometer. IR spectra were obtained on a Perkin Elmer SPECTRUM 1000 FT-IR spectrometer. High resolution MS were obtained on a Micromass LCT spectrometer. Elemental analysis was performed by Mikro Kemi AB. Uppsala, Sweden. Melting points, when given, were obtained on a Büchi or a Gallenkamp melting point apparatus and are uncorrected.

Example 1

2-(2-Phenoxy)ethyl 3-(1-piperazinyl)-2-pyrazinyl ether, Maleate

Step 1: 2-Chloro-3-(2-phenoxyethoxy)pyrazine.

NaO-t-Bu (2.91 g, 30.29 mmol) was added to a mixture of 2,3-dichloropyrazine (4.75 g, 31.9 mmol) and 2-phenoxyethanol (4.18 g, 30.3 mmol) in dioxane (25 mL). The reaction mixture was stirred at ambient temperature for 1.5 h and then filtered. The filtrate was concentrated under reduced pressure and the crystalline residue obtained was dried in a vacuum oven affording 4.4 g (62%) of the title compound as white waxy crystals: mp 55–54° C. Anal. ($C_{12}H_{11}ClN_2O_2$) C, H, N.

Step 2: 2-(2-Phenoxy)ethyl 3-(1-piperazinyl)-2-pyrazinyl ether, Maleate.

A mixture of the product from Step 1 (1.705 g, 6.80 mmol), piperazine (1.75 g, 20.3 mmol), and $K_2CO_3$ (1.16 g, 8.39 mmol) in acetonitrile (10 mL) was stirred at 50° C. for 1.5 h and for a further 3 h at 80° C. The reaction mixture was diluted with $CH_2Cl_2$, filtered, and concentrated. Purification of the semi-solid residue by chromatography on silica gel using $CHCl_3$/MeOH (9:1) as eluent gave a beige oil. This material was redissolved in ether/$CHCl_3$ (9:1), dried over $K_2CO_3$, and filtered through a short (3 cm) plug of alumina. The filtrate was concentrated in vacuo to afford 1.33 g (65%) of the title compound as the free base. The free base was converted to the maleate and recrystallized from MeOH/ether: mp 155–157° C.; HRMS m/z calcd for $C_{16}H_{20}N_4O_2$ $(M)^+$ 300.1586, found 300.1573. Anal. ($C_{16}H_{20}N_4O_2 \cdot C_4H_4O_4$) C, H, N.

Example 2

2-(2-Furylmethoxy)-3-(1-piperazinyl)pyrazine, Maleate

Step 1: 2-Chloro-3-(2-furylmethoxy))pyrazine.

The title compound was prepared according to the procedure described in Example 1. Step 1, starting from 2-furanmethanol (4.18 g, 42.7 mmol), 2,3-dichloropyrazine (2.05 g, 13.8 mmol) and KO-t-BuO (1.82 g, 16.2 mmol). The product, which was obtained as a yellowish oil in 68% yield, was used directly in the next step.

Step 2: 2-(2-Furylmethoxy)-3-(1-piperazinyl)pyrazine, Maleate.

The title compound was prepared according to the procedure described in Example 1, Step 2, starting from 2-chloro-3-(2-furylmethoxy)pyrazine (1.47 g, 7.0 mmol): yield 0.62 g (34%) as the free base. A portion of the free base was converted to the maleate salt: mp 118–120° C.; HRMS m/z calcd for $C_{13}H_{16}N_4O_2(M)^+$ 260.1273, found 260.1270. Anal. ($C_{13}H_{16}N_4O_2 \cdot C_4H_4O_4$) C, H, N.

Example 3

2-(2-Phenoxyethoxy)-3-(1-piperazinyl)quinoxaline, Hydrochloride

Step 1: 2-Chloro-3-(2-phenoxyethoxy)quinoxaline.

The title compound was prepared according to the procedure described in Example 1, Step 1, starting from 2-phenoxyethanol (3.7 g, 26.8 mmol), 2,3-dichloroquinoxaline (1.33 g, 6.7 mmol) and KO-t-Bu (0.75 g, 6.7 mmol): yield 0.74 g (37%); mp 99.5–101.5° C., HRMS m/z calcd for $C_{16}H_{13}ClN_2O_2(M)^+300.0666$, found 300.0672. Anal. ($C_{16}H_{13}ClN_2O_2$) C, H, N.

Step 2: 2-(2-Phenoxyethoxy)-3-(1-piperazinyl) quinoxaline, Hydrochloride.

The title compound vas prepared according to the procedure described in Example 1, Step 2, starting from 2-chloro-3-(2-phenoxyethoxy)quinoxaline (0.65 g, 2.15 mmol): yield 0.44 g (58%) as the free base. A portion of the free base was converted to its hydrochloride salt: mp 123–126° C.; HRMS m/z calcd for $C_{20}H_{22}N_4O_2(M)^+350.1743$, found 350.1748. Anal. ($C_{20}H_{22}N_4O_2 \cdot 1.75$ HCl·$0.5H_2O$)C, H, N.

Example 4

2-[2-(2-Naphthloxy)ethoxy]-3-(1-piperazinyl) pyrazine, Trifluoroacetate

Step 1: 2-Chloro-3-[2-(2-naphthyloxy)ethoxypyrazine.

Sodium hydride (55% dispersion in mineral oil; 44 mg, 1.0 mmol) was added to a mixture of 2-(2-naphthoxy) ethanol (188 mg, 1.00 mmol) and 2,3-dichloropyrazine (149 mg, 1.00 mmol) in dioxane (0.5 mL), and the reaction mixture was stirred at 40° C. for 15 h. The crude material was used directly in Step 2.

Step 2: 2-[2-(2-Naphthyloxy)ethoxy]-3-(1-piperazinyl) pyrazine, Trifluoroacetate.

A solution of piperazine (430 mg, 5.00 mmol) in a mixture of dioxane (0.5 mL) and DMF (1 mL) was added to the crude material from Step 1. The reaction mixture was stirred at 60° C. for 15 h, then diluted with EtOAc, washed with water, dried ($MgSO_4$), and concentrated under reduced pressure. The residue was purified by chromatography on silica gel using EtOAc/MeOH/HOAc/$H_2O$ (20:3:3:2) as eluent. The product-containing fractions were combined and concentrated. The residue was further purified by C-18 HPLC using $CH_3CN/H_2O$/TFA (gradient: $CH_3CN$ 0% to 100%, TFA 0.1%) to give 34.5 mg (10%) of the title product. HRMS m/z calcd for $C_{20}H_{22}N_4O_2(M)^+350.1743$, found 350.1742.

Examples 5–20 were prepared in an analogous manner starting from 2,3-dichloropyrazine (1 mmol) and the appropriate alcohol (1 mmol).

Example 5

2-(4-Bromophenoxy)ethyl 3-(1-piperazinyl)-2-pyrazinyl ether, Trifluoroacetate

The title compound was prepared starting from 2-(4-bromophenoxy)ethanol to give 47 mg (12%). HRMS m/z calcd for $C_{16}H_{19}BrN_4O_2(M)^+378.0691$, found 378.0698.

Example 6

2-(2-Chlorophenoxy)ethyl 3-(1-piperazinyl)-2-pyrazinyl ether, Trifluoroacetate

The title compound was prepared starting from 2-(2-chlorophenoxy)ethanol to give 32 mg (10%). HRMS m/z calcd for $C_{16}H_{10}ClN_4O_2$ $(M)^+334.1197$, found 334.1195.

Example 7

2-(4-Chlorophenoxy)ethyl 3-(1-piperazinyl)-2-pyrazinyl ether, Trifluoroacetate

The title compound was prepared starting from 2-(4-chlorophenoxy)ethanol to give 56 mg(17%). HRMS m/z called for $C_{16}H_{19}ClN_4O_2(M)^+33.1197$, found 334.1182.

Example 8

2-Phenoxypropyl 3-(1-piperazinyl)-2-pyrazinyl ether, Trifluoroacetate

The title compound was prepared starting from 2-phenoxypropanol to give 24 mg (6%). HRMS m/z calcd for $C_{17}H_{22}N_4O_2(M)^+314.1743$, found 314.1742.

Example 9

2-Phenoxy-1-methylethyl 3-(1-piperazinyl)-2-pyrazinyl ether, Trifluoroacetate

The title compound was prepared starting from 1-phenoxy-2-propanol to give 29 mg (9%). HRMS m/z calcd for $C_{17}H_{22}N_4O_2(M)^+314.1743$, found 314.1732.

Example 10

2-(2-Methoxyphenoxy)-1-methylethyl 3-(1-piperazinyl)-2-pyrazinyl ether, Trifluoroacetate The title compound was prepared starting from 1-(2-methoxyphenoxy)-2-propanol to give 25 mg (5%). HRMS m/z calcd for $C_{18}H_{24}N_4O_3(M)^+344.1848$, found 344.1852.

Example 11

2-(3-Methoxyphenoxy)-1-methylethyl 3-(1-piperazinyl)-2-pyrazinyl ether, Trifluoroacetate The title compound was prepared starting from 1-(3-methoxyphenoxy)-2-propanol to give 38 mg (11%). HRMS m/z calcd for $C_{18}H_{24}N_4O_3(M)^+344.1848$, found 344.1842.

Example 12

2-(2-Methylphenoxy)-1-methylethyl 3-(1-piperazinyl)-2-pyrazinyl ether, Trifluoroacetate The title compound was prepared starting from 1-(2-methylphenoxy)-2-propanol to give 60 mg (18%). HRMS m/z calcd for $C_{18}H_{24}N_4O_2(M)^+328.1899$, found 328.1898.

Example 13

2-(4-Methylphenoxy)-1-methylethyl 3-(1-piperazinyl)-2-pyrazinyl ether, Trifluoroacetate The title compound was prepared starting from 1-(4-methylphenoxy)-2-propanol to give 12 mg (3%). HRMS m/z calcd for $C_{18}H_{24}N_4O_2(M)^+328.1899$, found 328.1896.

Example 14

2-(Phenylthio)ethyl 3-(1-piperazinyl)-2-pyrazinyl ether, Trifluoroacetate

The title compound was prepared starting from 2-(phenylthio)ethanol to give 30 mg (10%). HRMS m/z calcd for $C_{16}H_{20}N_4OS$ $(M)^+316.1358$, found 316.1359.

Example 15

2-(Anilino)ethyl 3-(1-piperazinyl)-2-pyrazinyl ether, Trifluoroacetate

The title compound was prepared starting from 2-anilinoethanol to give 48 mg (16%). HRMS m/z calcd for $C_{16}H_{2/}N_5O$ $(M)^+299.1746$, found 299.1754.

Example 16

2-(N-Ethylanilino)ethyl 3-(1-piperazinyl)-2-pyrazinyl ether, Trifluoroacetate

The title compound was prepared starting from 2-(N-ethylanilino)ethanol to give 7 mg (2%). HRMS m/z calcd for $C_{18}H_{25}N_5O$ $(M)^+327.2059$, found 327.2057.

Example 17

2,3-Dihydro-1,4-benzodioxin-2-ylmethyl 3-(1-piperazinyl)-2-pyrazinyl ether, Trifluoroacetate The title compound was prepared starting from 2-hydroxymethyl-1,4-benzodioxane to give 22 mg (5%). HRMS m/z calcd for $C_{17}H_{20}N_4O_3(M)^+$ 328.1535, found 328.1519.

Example 18

3-Phenylpropyl 3-(1-piperazinyl)-2-pyrazinyl ether, Trifluoroacetate

The title compound was prepared starting from 3-phenyl-1-propanol to give 9 mg (2%). HRMS m/z calcd for $C_{17}H_{22}N_4O$ $(M)^+$ 298.1794, found 298.1795.

Example 19

4-Phenylbutyl 3-(1-piperazinyl)-2-pyrazinyl ether, Trifluoroacetate

The title compound was prepared starting from 4-phenyl-1-butanol to give 10 mg (2%). HRMS m/z calcd for $C_{18}H_{24}N_4O$ $(M)^+$ 312.1950, found 312.1963.

Example 20

2-(Benzyloxy)ethyl 3-(1-piperazinyl)-2-pyrazinyl ether, Trifluoroacetate

The title compound was prepared starting from 2-benzyloxyethanol to give 31 mg (7%). HRMS m/z calcd for $C_{17}H_{22}N_4O_2(M)^+$ 314.1743, found 314.1739.

Example 21

4-(2-{[3-(1-piperazinyl)-2-pyrazinyl]oxy}ethoxy)-1,3-benzoxazol-2-amine, Fumarate Step 1: 4-(2-Hydroxyethoxy)-2-amino-1,3-benzoxazol.

The title compound was prepared according to the procedure of Example 91, Step 1, starting from 4-hydroxy-2-amino-1,3-benzoxazol*(0.97 g, 6.5 mmol) and ethylene carbonate (0.63 g, 7.1 mmol). Solid; yield 46%; mp 124–126° C. Anal. ($C_9H_{10}N_2O_3$) C, H, N.

*Previously described in J. Chem. Soc. 1960, 2369–2370.

Step 2: 4-{2-[(3-Chloro-2-pyrazinyl)oxy]ethoxy}-1,3-benzoxazol-2-amine.

The title compound was prepared according to the procedure of Example 4, Step 1, except that 4 equiv of both NaH and 2,3-dichloropyrazine were used, starting from the product of Step 1. The reaction temperature was 90° C. The crude product was used directly in the next step.

Step 3: 4-(2-{[3-(1-Piperazinyl)-2-pyrazinyl]oxy}ethoxy)-1,3-benzoxazol-2-amine Fumarate.

The title compound was prepared according to the procedure of Example 1. Step 2, starting from the product of Step 2 above. Yield of free base 24%. The free base was converted to the fumarate salt: mp 138–140° C. Anal. ($C_{17}H_{20}N_6O_3 \cdot C_4H_4O_4 \cdot 0.25H_2O$) C, H, N.

Example 22

2-(Phenoxy)ethyl 3-(3-amino-1-pyrrolidinyl)-2-pyrazinyl ether

The title compound was prepared according to the procedure described in Example 4, Step 2, starting from 2-chloro-3-(2-phenoxyethoxy)pyrazine (150 mg, 0.60 mmol; from Example 1, Step 1) and 3-aminopyrrolidine (270 mg, 3.13 mmol) with the exception that a final extraction step between EtOAc and 5% aqueous NaOH was carried out. This gave 121 mg (67%) of the title product. Anal. ($C_{16}H_{19}N_4O_2$) C, H; N: calcd, 18.65; found, 18.0.

Example 23

2-(2-Chlorophenoxy)ethyl 3-(3-amino-1-pyrrolidinyl)-2-pyrazinyl ether

The title compound was prepared according to the procedure described in Example 4, Step 2, starting from 2-chloro-3-[2-(2-chlorophenoxy)ethoxy]pyrazine*(150 mg, 0.53 mmol) and 3-aminopyrrolidine (252 mg, 2.92 mmol) with the exception that a final extraction step between EtOAc and 5% aqueous NaOH was carried out. This gave 100 mg(56%) of the title product. Anal. ($C_{16}H_{19}ClN_4O_2$) C, H; N: calcd, 16.73; found, 16.0.

*Prepared according to the procedure described in Example 4, Step 1.

Example 24

2-(4-Chlorophenoxy)ethyl 3-(3-amino-1-pyrrolidinyl)-2-pyrazinyl ether

The title compound was prepared according to the procedure described in Example 4, Step 2, starting from 2-chloro-3-[2-(4-chlorophenoxy)ethoxy]pyrazine*(150 mg, 0.53 mmol) and 3-aminopyrrolidine (247 mg, 2.87 mmol) with the exception that a final extraction step between EtOAc and 5% aqueous NaOH was carried out. This gave 123 mg (69%) of the title product. Anal. ($C_{16}H_{19}ClN_4O_2$) H, N; C: calcd. 57.40; found, 56.9.

*Prepared according to the procedure described in Example 4, Step 1.

Example 25

2-(Phenoxy)ethyl 3-(1,4-diazepan-1-yl)-2-pyrazinyl ether

The title compound was prepared according to the procedure described in Example 4, Step 2, starting from 2-chloro-3-(2-phenoxyethoxy)pyrazine (150 mg, 0.60 mmol; from Example 1, Step 1) and homopiperazine (250 mg, 2.5 mmol) with the exception that a final extraction step between EtOAc and 5% aqueous NaOH was carried out. This gave 141 mg (75%) of the title product. Anal. ($C_{17}H_{22}N_4O_2 \cdot 0.35EtOAc$) C, H, N.

Example 26

2,3-Dihydro-1,4-benzodioxin-2-ylmethyl 3-(1,4-diazepan-1-yl)-2-pyrazinyl ether

The title compound was prepared according to the procedure described in Example 4, Step 2, starting from 2-chloro-3-(2,3-dihydro-1,4-benzodioxin-2-ylmethoxy)pyrazine* (150 mg, 0.54 mmol) and homopiperazine (266 mg, 2.66 mmol) with the exception that a final extraction step between EtOAc and 5% aqueous NaOH was carried out. This gave 105 mg (57%) of the title product. Anal. ($C_{18}H_{24}N_4O_3$) H, N; C: calcd, 63.14; found, 62.70.

*Prepared according to the procedure described in Example 4, Step 1.

Example 27

2-(4-Chlorophenoxy)ethyl 3-(1,4-diazepan-1-yl)-2-pyrazinyl ether

The title compound was prepared according to the procedure described in Example 4, Step 2, starting from 2-chloro-3-[2-(4-chlorophenoxy)ethoxy]pyrazine*(150 mg, 0.53 mmol) and homopiperazine (287 mg, 2.87 mmol) with the exception that a final extraction step between EtOAc and 5% aqueous NaOH was carried out. This gave 128 mg (69%) of the title product. HRMS m/z calcd for $C_{17}H_{21}ClN_4O_2$ $(M)^+$348.1353, found 348.1353. Anal. $(C_{17}H_{21}ClN_4O_2)$ C, H, N.

*Prepared according to the procedure described in Example 4, Step 1.

Example 28

2-(Phenoxy)ethyl 3-(3-methyl-1-piperazinyl)-2-pyrazinyl ether

The title compound was prepared according to the procedure described in Example 4. Step 2, starting from 2-chloro-3-(2-phenoxyethoxy)pyrazine (150 mg, 0.54 mmol, from Example 1, Step 1) and 2-methylpiperazine (250 mg, 2.5 mmol) with the exception that a final extraction step between EtOAc and 5% aqueous NaOH was carried out. This gave 138 mg (73%) of the title product. Anal. $(C_{17}H_{22}N_4O_2)$ C, H, N.

*Prepared according to the procedure described in Example 4, Step 1.

Example 29

2-(4-Chlorophenoxy)ethyl 3-(3-methyl-1-piperazinyl)-2-pyrazinyl ether

The title compound was prepared according to the procedure described in Example 4, Step 2, starting from 2-chloro-3-[2-(4-chlorophenoxy)ethoxy]pyrazine*(150 mg, 0.53 mmol) and 2-methylpiperazine (256 mg, 2.56 mmol) with the exception that a final extraction step between EtOAc and 5% aqueous NaOH was carried out. This gave 143 mg (77%) of the title product. HRMS m/z calcd for $C_{17}H_{21}ClN_4O_2(M)^+$348.1353, found 348.1370. Anal. $(C_{17}H_{21}ClN_4O_2)$C, H, N.

*Prepared according to the procedure described in Example 4, Step 1.

Example 30

2-(2-Methoxyphenoxy)-1-methylethyl 3-(3-methyl-1-piperazinyl)-2-pyrazinyl ether

The title compound was prepared according to the procedure described in Example 4, Step 2, starting from 2-chloro-3-[2-(2-methoxyphenoxy)-1-methylethoxy]pyrazine* (150 mg, 0.51 mmol) and 2-methylpiperazine (260 mg, 2.6 mmol) with the exception that a final extraction step between EtOAc and 5% aqueous NaOH was carried out. This gave 118 mg (65%) of the title product. HRMS m/z calcd for $C_{19}H_{26}N_4O_3M)^+$358.2005, found 358.2018. Anal. $(C_{19}H_{26}N_4O_3)$ C, H, N.

*Prepared according to the procedure described in Example 4, Step 1.

Example 31

2,3-Dihydro-1,4-benzodioxin-2-ylmethyl 3-(3-methyl-1-piperazinyl)-2-pyrazinyl ether The title compound was prepared according to the procedure described in Example 4, Step 2, starting from 2-chloro-3-(2,3-dihydro-1,4-benzodioxin-2-ylmethoxy)pyrazine* (150 mg, 0.54 mmol) and 2-methylpiperazine (293 mg, 2.92 mmol) with the exception that a final extraction step between EtOAc and 5% aqueous NaOH was carried out. This gave 118 mg (64%) of the title product. HRMS m/z calcd for $C_{18}H_{22}N_4O_3(M)^+$342.1692, found 342.1678. Anal. $(C_{18}H_{22}N_4O_3)$ H, N; C: calcd, 63.14; found, 62.30.

*Prepared according to the procedure described in Example 4, Step 1.

Example 32

2-(Phenoxy)ethyl 3-(4-ethyl-1-piperazinyl)-2-pyrazinyl ether

The title compound was prepared according to the procedure described in Example 4, Step 2, starting from 2-chloro-3-(2-phenoxyethoxy)pyrazine (150 mg, 0.60 mmol; from Example 1, Step 1) and N-ethylpiperazine (250 mg, 2.19 mmol) with the exception that a final extraction step between EtOAc and 5% aqueous NaOH was carried out. This gave 127 mg (64%) of the title product. Anal. $(C_{18}H_{24}N_4O_2)$ C, H, N.

Example 33

2-(2-Chlorophenoxy)ethyl 3-(4-ethyl-1-piperazinyl)-2-pyrazinyl ether

The title compound was prepared in an analogous manner to Example 4, Step 2, starting from 2-chloro-3-[2-(2-chlorophenoxy)ethoxy]pyrazine*(150 mg, 0.53 mmol) and N-ethylpiperazine (221 mg, 1.93 mmol) with the exception that a final extraction step between EtOAc and 5% aqueous NaOH was carried out. This gave 100 mg (52%) of the title product. Anal. $(C_{18}H_{24}Cl_4O_2)$ C, H, N.

*Prepared according to the procedure described in Example 4, Step 1.

Example 34

2-(4-Chlorophenoxy)ethyl 3-(4-ethyl-1-piperazinyl)-2-pyrazinyl ether

The title compound was prepared according to the procedure described in Example 4. Step 2, starting from 2-chloro-3-[2-(4-chlorophenoxy)ethoxy]pyrazine*(150 mg, 0.53 mmol) and N-ethylpiperazine (221 mg, 1.93 mmol) with the exception that a final extraction step between EtOAc and 5% aqueous NaOH was carried out. This gave 138 mg (72%) of the title product. HRMS m/z calcd for $C_{18}H_{23}ClN_4O_2(M)^+$362.1510, found 362.1526. Anal. $(C_{18}H_{23}ClN_4O_2)$C, H, N.

*Prepared according to the procedure described in Example 4, Step 1.

Example 35

2,3-Dihydro-1,4-benzodioxin-2-ylmethyl 3-(4-ethyl-1-piperazinyl)-2-pyrazinyl ether The title compound was prepared according to the procedure described in Example 4, Step 2, starting from 2-chloro-3-(2,3-dihydro-1,4-benzodioxin-2-ylmethoxy)pyrazine* (150 mg, 0.54 mmol) and N-ethylpiperazine (219 mg, 1.92 mmol) with the exception that a final extraction step between EtOAc and 5% aqueous NaOH was carried out. This gave 128 mg (66%) of the title product. HRMS m/z calcd for $C_{19}H_{24}N_4O_3(M)^+$356.1848, found 356.1848. Anal. $(C_{19}H_{24}N_4O_3)$ C, H, N.

*Prepared according to the procedure described in Example 4, Step 1.

Example 36

2-(2-Methoxyphenoxy)-1-methylethyl 3-(4-ethyl-1-piperazinyl)-2-pyrazinyl ether

The title compound was prepared according to the procedure described in Example 4, Step 2, starting from 2-chloro-3-[2-(2-methoxyphenoxy)-1-methylethoxy] pyrazine* (150 mg, 0.51 mmol) and N-ethylpiperazine (222 mg, 1.94 mmol) with the exception that a final extraction step between EtOAc and 5% aqueous NaOH was carried out. This gave 127 mg (67%) of the title product. HRMS m/z calcd for $C_{20}H_{28}N_4O_3(M)^+$ 372.2161, found 372.2174. Anal. $(C_{20}H_{28}N_4O_3)$ C, H, N.

*Prepared according to the procedure described in Example 4, Step I.

Example 37

2-(3-Bromophenoxy)ethyl 3-(1-piperazinyl)-2-pyrazinyl ether

Step 1: 2-(3-Bromophenoxy)ethyl 3-chloro-2-pyrazinyl ether.

A mixture of 3-bromophenol (1.73 g, 10.0 mmol), ethylene oxide (0.44 g, 10 mmol). $Et_3N$ (3 drops) and dioxane (4 mL) was heated at 100° C. in a sealed tube for 2 d. The solution was cooled in an ice-bath and KO-t-Bu (1.07 g, 9.50 mmol) followed by 2,3-dichloropyrazine (1.34 g, 9 mmol) were added along with dioxane (1 mL). The mixture was stirred at room temperature for 90 min, diluted with $CH_2Cl_2$ and filtered. The filtrate was concentrated and the residue was purified by chromatography-on silica gel (gradient: isohexane to 25% EtOAc/isohexane) to give 2.21 g (75%) of the title product as a white solid: mp 57–58° C. Anal. $(C_{12}H_{10}BrClN_2O_2)$ C, H, N.

Step 2: 2-(3-Bromophenoxy)ethyl 3-(1-piperazinyl)-2-pyrazinyl ether.

Piperazine (1.29 g, 15.0 mmol) and $K_2CO_3$ (0.69 g, 5.0 mmol) were added to a solution of 2-(3-bromophenoxy) ethyl 3-chloro-2-pyrazinyl ether (1.65 g, 5.00 mmol) in acetonitrile (25 mL) at room temperature. The mixture was heated at reflux for 21 h, allowed to cool, concentrated and the residue was partitioned between water and EtOAc. The layers were separated and the organic phase was washed with water and brine, and dried over $MgSO_4$. Purification by chromatography on silica gel (gradient: PhMe to PhMe/MeOH/$Et_3N$, 8:1:1) gave 1.61 g (85%) of the title compound as a pale yellow oil that slowly solidified on standing: mp 62–63° C. Anal. $(C_{16}H_{19}BrN_4O_2)$ C, H, N.

Example 38

2-[2-(2-Chlorophenoxy)ethoxy]-3-(1-piperazinyl) quinoxaline

Step 1: 2-Chloro-3-[2-(2-chlorophenoxy)ethoxy] quinoxaline.

2-(2-Chlorophenoxy)ethanol (0.229 g, 1.33 mmol) was treated with NaH (55% dispersion in mineral oil; 0.058 g, 1.33 mmol) in dioxane (2 mL). After stirring at room temperature for 3 h, the mixture was added dropwise to a slurry of 2,3-dichloroquinoxaline (0.320 g, 1.60 mmol) in dioxane (1 mL). The resulting mixture was stirred at room temperature for 15 h to produce the intermediate 2-chloro-3-[2-(2-chlorophenoxy)ethoxy]quinoxaline which was used directly in the next step.

Step 2: 2-[2-(2-Chlorophenoxy)ethoxy]-3-(1-piperazinyl) quinoxaline.

Piperazine (0.580 g, 6.65 mmol) was added to the crude material from Step 1 and the resulting mixture was stirred at room temperature for 5 h. The solvent was evaporated, and the crude mixture was dissolved in DMSO and precipitated with water. The precipitate was purified by chromatography on silica gel using EtOAc/HOAc/MeOH/$H_2O$ (40:3:3:2) as eluent to afford 0.100 g (22%) of the title compound as a yellow oil. HRMS m/z calcd for $C_{20}H_{21}ClN_4O_2(M)^+$ 384.1353, found 384.1334.

Examples 39–45 were prepared according to the procedure of Example 38, starting from 2,3-dichloroquinoxaline and the appropriate alcohol.

Example 39

2-[2-(4-Chlorophenoxy)ethoxy]-3-(1-piperazinyl) quinoxaline

The title compound was prepared starting from 2-(4-chlorophenoxy)ethanol (0.229 g, 1.33 mmol) to give 0.250 g (56%) of a yellow solid: mp 108–112° C.; HRMS m/z calcd for $C_{20}H_{21}ClN_4O_2(M)^+$ 384.1353, found 384.1347.

Example 40

2-[2-(Phenylthio)ethoxy]-3-(1-piperazinyl) quinoxaline

The title compound was prepared starting from 2-(phenylthio)ethanol (0.205 g, 1.33 mmol) to give 0.045 g (9%) of a yellow oil. HRMS m/z calcd for $C_{20}H_{22}N_4OS$ $(M)^+$ 366.1514, found 366.1509.

Example 41

2-(1-Methyl-2-phenoxyethoxy)-3-(1-piperazinyl) quinoxaline

The title compound was prepared starting from 1-methyl-2-phenoxyethanol (0.202 g, 1.33 mmol) to give 0.084 g (17%) of a yellow oil. HRMS m/z calcd for $C_{21}H_{24}N_4O_2$ $(M)^+$ 364.1899, found 364.1908.

Example 42

2-[1-Methyl-2-(4-methylphenoxy)ethoxy]-3-(1-piperazinyl)quinoxaline

The title compound was prepared starting from 1-methyl-2-(4-methylphenoxy)ethanol (0.221 g, 1.33 mmol) to have 0.047 g (9%) of a yellow oil. Anal. $(C_{22}H_{26}N_4O_2)$C, H, N.

Example 43

2-[2-(2-Methoxyphenoxy)-1-methylethoxy]-3-(1-piperazinyl)quinoxaline

The title compound was prepared starting from 1-methyl-2-(2-methoxyphenoxy)ethanol (0.242 g, 1.33 mmol) to give 0.072 g (14%) of a yellow oil. Anal. $(C_{22}H_{26}N_4O_3)$ C, H, N: calcd, 14.20; found, 13.70.

Example 44

2-(2,3-Dihydro-1,4-benzodioxin-2-ylmethoxy)-3-(1-piperazinyl)quinoxaline

The title compound was prepared starting from 2,3-dihydro-1,4-benzodioxin-2-ylmethanol (0.221 g, 1.33 mmol) to give 0.18 g (35%) of a yellow oil. Anal. $(C_{21}H_{22}N_4O_3)$ C, H, N.

Example 45

2-[2-(2-Naphthyloxy)ethoxy]-3-(1-piperazinyl) quinoxaline

The title compound was prepared starting from 2-(2-naphthyloxy)ethanol (0.250 g, 1.33 mmol) to give 0.22 g (41%) of a yellow solid. HRMS m/z calcd for $C_{24}H_{24}N_4O_2$ $(M)^+$ 400.1899, found 400.1902.

Example 46

2-(2-Phenoxyethylamino)-3-(1-piperazinyl)pyrazine

Step 1: 2-Chloro-3-(2-phenoxyethylamino)pyrazine.

A mixture of 2-phenoxyethylamine (2.65 g, 19.3 mmol), 2,3-dichloropyrazine (2.88 g, 19.3 mmol) and $K_2CO_3$ (2.67 g, 19.3 mmol) in acetonitrile (8 mL) was stirred in a sealed tube for 12 h at room temperature, and for a further 9.5 h at 80° C. The reaction mixture was diluted with ether, filtered, and concentrated. The residue was purified by chromatography on silica gel using n-hexane/EtOAc (7:3) as eluent to give 2.36 g (49%) of the title compound as a yellowish oil that solidified on standing: mp 51–53° C.; HRMS m/z called for $C_{12}H_{12}ClN_3O$ $(M)^+$249.0669, found 249.0659, Anal. $(C_{12}H_{12}ClN_3O)$C, H, N.

Step 2: 2-(2-Phenoxyethylamino)-3-(1-piperazinyl)pyrazine.

A mixture of the product from Step 1 above (1.59 g, 6.37 mmol), piperazine (1.56 g, 18.2 mmol), and $K_2CO_3$ (0.88 g, 6.4 mmol) in acetonitrile (10 mL) was stirred at 140° C. for 12 h in a sealed tube. After cooling, the reaction mixture was diluted with $CH_2Cl_2$, filtered, and concentrated. The semi-solid residue %% as purified by chromatography on silica gel using $CHCl_3$/MeOH (9:1) as eluent to give a beige oil. This oil was redissolved in $CHCl_3$, and filtered through a short (3 cm) plug of alumina covered with $K_2CO_3$. The pad was washed with several portions of $CHCl_3$ and the resulting filtrate was concentrated to afford 1.48 g (78%) of the title product as a pale yellow oil. HRMS m/z calcd for $C_{16}H_{21}N_5O$ $(M)^+$299.1746, found 299.1753. Anal. $(C_{16}H_{21}N_5O\cdot\frac{1}{3}H_2O)$C, H, N.

Example 47

N-Methyl-N-(2-phenoxyethyl)-3-(1-piperazinyl)-2-pyrazinamine, Fumarate

Step 1: 3-Chloro-N-methyl-N-(2-phenoxyethyl)-2-pyrazinamine.

A mixture of 2,3-dichloropyrazine (6.64 g, 44.6 mmol) and N-methyl-N-(2-phenoxyethyl)amine* (4.5 g, 29.8 mmol) in DMF (5 mL) was placed in a sealed Pyrex tube and heated in a microwave oven (Labwell MW10) for 1×2 min followed by 2×1 min at 75 W. The mixture was concentrated and the resulting oil was purified by column chromatography on silica using hexane/EtOAc (95:5 followed by 93:7) to give 5.56 g (71%) of the title product as a colorless oil. HRMS m/z calcd for $C_{13}H_{14}ClN_3O$ $(M)^+$263.0825, found 263.0824.

*Previously described in *J. Chem. Soc.* 1963, 1385–1400.

Step 2: N-Methyl-N-(2-phenoxyethyl)-3-(1-piperazinyl)-2-pyrazinamine, Fumarate.

A mixture of the product obtained in Step 1 (5.0 g, 19 mmol) and piperazine (5.0 g, 59.4 mmol) in DMF (10 mL) was placed in a sealed Pyrex tube and heated in a microwave oven (Labwell MW10) for 2.5 min at 75 W. The mixture was concentrated and the remaining yellow oil was partitioned between water and $CHCl_3$. The water phase was extracted with $CHCl_3$ (×2) and the combined organic phases were extracted with 0.5 M aqueous HCl (×2). The combined aqueous phases were made alkaline (11M NaOH) and extracted with $CHCl_3$ (×3). The combined organic phases were washed with water and brine, dried ($MgSO_4$), and concentrated to give the free base of the title product as a light yellow oil. The free base was converted to its fumarate salt. Yield 1.38 g (17%) of off-white crystals from methanol; mp 154° C. Anal. $(C_{17}H_{23}N_5O\cdot C_4H_4O_4)$ H, N; C: calcd, 58.7, found, 58.05.

Example 48

2-(Phenoxy)ethyl 3-(3-pyrrolidinyloxy)-2-pyrazinyl ether

2-Chloro-3-(2-phenoxyethoxy)pyrazine (150 mg, 0.60 mmol; from Example 1, Step 1) was added to a stirred mixture of 3-pyrrolidinol (260 mg, 2.99 mmol) and NaH (55% dispersion in mineral oil; 110 mg, 2.50 mmol) in dioxane (2 mL), and the reaction was stirred at room temperature for 2 h. EtOAc was added and the mixture was washed with water, dried ($MgSO_4$), and concentrated. The residue was purified by chromatography on silica gel using EtOAc/MeOH/HOAc/$H_2O$ (50:40:9:1) as eluent to give 38 mg (22%) of the title compound. Anal. $(C_{16}H_{19}N_3O_3)$ H; C: calcd, 63.77; found, 62.20; N: calcd, 13.94; found, 13.0.

Example 49

2-(Phenoxy)ethyl 3-[(3R)-pyrrolidinyloxy]-2-pyrazinyl ether

Step 1: 2-(Phenoxy)ethyl 3-[N-tert-butoxycarbonyl (3R)-pyrrolidinyloxy]-2-pyrazinyl ether.

2-Chloro-3-(2-phenoxyethoxy)pyrazine (250 mg, 1.00 mmol; from Example 1, Step 1) was added to a mixture of N-Boc-(R)-3-pyrrolidinol (225 mg, 1.20 mmol) and KO-t-Bu (140 mg, 1.25 mmol) in toluene (5 mL), and the reaction was stirred at 95° C. for 30 min. The reaction mixture was diluted with toluene, washed with water, dried ($MgSO_4$), and concentrated under reduced pressure. The residue was purified by chromatography on silica gel using toluene/EtOAc (9:1) as eluent to give 261 mg (65%) of the title product which was used in the next step without further characterization.

Step 2: 2-(Phenoxy)ethyl 3-[(3R)-pyrrolidinyloxy]-2-pyrazinyl ether.

The product from Step 1 above was treated with $CH_2Cl_2$/trifluoroacetic acid/$H_2O$ (50:45:5; 4 mL) for 30 min. The mixture was concentrated and the residue was partitioned between 5% aqueous NaOH and $CH_2Cl_2$. After separation, the organic layer was dried ($MgSO_4$) and concentrated. The residue was purified by chromatography on silica gel using $CH_2Cl_2$/MeOH (8:2) as eluent to give 44 mg (15%) of the title product: $[\alpha]_D=-4.6°$ (c 0.017, MeOH); HRMS m/z calcd for $C_{16}H_{19}N_3O_3$ $(M)^+$301.1426, found 301.1427.

Example 50

2-(Phenoxy)ethyl 3-(4-piperidinyloxy)-2-pyrazinyl ether

The title compound was prepared according to the procedure described in Example 49 starting from 2-chloro-3-(2-phenoxyethoxy)pyrazine (250 mg, 1.00 mmol; from Example 1, Step 1) and N-Boc-4-hydroxypiperidine (234 mg, 1.16 mmol) to give 112 mg (35%) of the title product. HRMS m/z calcd for $C_{17}H_{23}N_3O_3(M)^*$ 315.1583, found 315.1570.

Example 51

2-(Phenoxy)ethyl 3-[(2S)-pyrrolidinylmethoxy]-2-pyrazinyl ether

The title compound was prepared according to the procedure described in Example 49, starting from 2-chloro-3-(2-phenoxyethoxy)pyrazine (250 mg, 1.00 mmol; from Example 1, Step 1) and N-Boc-L-prolinol (250 mg, 1.24 mmol). The intermediate product 2-(phenoxy)ethyl 3-[N-tert-butoxycarbonyl (2S)-pyrrolidinylmethoxy]-2-pyrazinyl ether was not characterized. Yield 23 mg (7%); $[\alpha]_D=13.2°$ (c 0.016, MeOH). HRMS m/z calcd for $C_{17}H_{21}N_3O_3(M)^+$ 315.1583, found 315.1598.

Example 52

2-(2-Methoxyphenoxy)ethyl 3-(1-piperazinyl)-2-pyrazinyl ether

Step 1: 2-Chloro-3-(4-tert-butoxycarbonyl-1-piperazinyl)pyrazine.

A mixture of N-Boc-piperazine (11.47 g, 61.5 mmol), $K_2CO_3$ (8.5 g, 61 mmol) and 2,3-dichloropyrazine (9.20 g, 61.7 mmol) in acetonitrile (100 mL) was stirred at 100° C. for 40 h. The reaction mixture was concentrated, dissolved in toluene, washed with water, dried ($MgSO_4$), and concentrated. The residue was purified by chromatography on silica gel using toluene/EtOAc (7:3) as eluent to give 18.3 g (100%) of the title product. HRMS m/z calcd for $C_{13}H_{19}N_4O_2(M)^+$ 298.1197, found 298.1206.

Step 2: 2-[3-(4-tert-Butoxycarbonyl-1-piperazinyl)-2-pyrazinyloxy]ethanol.

KO-t-Bu (9.92 g, 103 mmol) was added to a mixture of the product obtained in Step 1 (18.14 g, 60.7 mmol) and ethylene glycol (25 mL, 448 mmol) in pyridine (125 mL) at 85° C. The reaction mixture was stirred for 15 h and then poured into ice-water and extracted with toluene. The organic phase was dried ($MgSO_4$) and concentrated. The residue was purified by chromatography on silica gel using toluene/EtOAc (1:1) as eluent to give 16.9 g (85%) of the title product. HRMS m/z calcd for $C_{15}H_{24}N_4O_4(M)^+$ 324.1798, found 324.1784.

Step 3: 2-(2-Methoxyphenoxy)ethyl 3-(1-piperazinyl)-2-pyrazinyl ether.

1,1'-Azobis(N,N-dimethylfomamide) (TMAD; 60 mg, 0.35 mmol) was dissolved in THF (1 mL) and DMF (0.5 mL) and added to a stirred solution of the product from Step 2 (100 mg, 0.31 mmol), 2-methoxyphenol (124 mg, 1.00 mmol) and triphenylphosphine (92 mg, 0.35 mmol) in THF (1 mL). The reaction mixture was stirred for 15 h and then concentrated under reduced pressure. The residue was passed through a bed of silica gel using toluene/EtOAc/MeOH (45:45:10) as eluent, and the pure fractions were combined, concentrated and treated with $CH_2Cl_2$/TFA/$H_2O$ (50:45:5; 5 mL) for 30 min. The mixture was concentrated and the residue was purified by chromatography on silica gel using EtOAc/HOAc/MeOH/$H_2O$ (20:3:3:2) as eluent. The combined product-containing fractions were concentrated and partioned between 5% aqueous NaOH and $CH_2Cl_2$. The organic phase was concentrated, and the residue was purified by chromatography on silica gel using $CH_2Cl_2$/MeOH (8:2) as eluent to give 11.2 mg (11%) of the title product. HRMS m/z calcd for $C_{17}H_{22}N_4O_3(M)^+$ 330.1692, found 330.1707.

Examples 53–68 were prepared according to the procedure described in Example 52, Step 3, starting from 2-[3-(4-tert-butoxycarbonyl-1-piperazinyl)-2-pyrazinyloxy]ethanol and the requisite phenolic compound (1 mmol unless otherwise noted).

Example 53

2-(4-n-Butoxyphenoxy)ethyl 3-(1-piperazinyl)-2-pyrazinyl ether, Trifluoroacetate The title compound was prepared starting from p-butoxyphenol, but no extraction with NaOH and without the third chromatographic step, to give 92 mg (19%) as the trifluoroacetate salt. HRMS m/z calcd for $C_{20}H_{28}N_4O_3(M)^+$ 372.2161, found 372.2162.

Example 54

2-(2-Isopropoxyphenoxy)ethyl 3-(1-piperazinyl)-2-pyrazinyl ether

The title compound was prepared starting from 2-isopropoxyphenol to give 216 mg (60%). HRMS m/z calcd for $C_{19}H_{26}N_4O_3(M)^+$ 358.2005, found 358.2006.

Example 55

2-(1-Naphthyloxy)ethyl 3-(1-piperazinyl)-2-pyrazinyl ether

The title compound was prepared starting from 1-naphthol to give 142 mg (40%). HRMS m/z calcd for $C_{20}H_{22}N_4O_2(M)^+$ 350.1743, found 350.1758.

Example 56

2-(2,5-Difluorophenoxy)ethyl 3-(1-piperazinyl)-2-pyrazinyl ether, Trifluoroacetate The title compound was prepared starting from 2,5-difluorophenol, but no extraction with NaOH and without the third chromatographic step, to give 21 mg (6%) as the trifluoroacetate salt. HRMS m/z calcd for $C_{16}H_{18}F_2N_4O_2(M)^+$ 336.1398. Found 336.1407.

Example 57

2-(3,5-Dimethoxyphenoxy)ethyl 3-(1-piperazinyl)-2-pyrazinyl ether

The title compound was prepared starting from 3,5-dimethoxyphenol to give 52 mg (14%). HRMS m/z calcd for $C_{18}H_{24}N_4O_4(M)^+$ 360.1798, found 360.1808.

Example 58

2-[2-(2-Methoxy-5-nitrophenoxy)ethoxy]-3-(1-piperazinyl)pyrazine, Hydrochloride The title compound was prepared starting from 2-methoxy-5-nitrophenol (0.524 g, 3.08 mmol) to give 0.53 g (42%). Pos-EI-MS shows M+ and 10 ions supporting the stated structure. HRMS m/z calcd for $C_{17}H_{21}N_5O_5(M)^+$ 375.1543, found 375.1561. Anal. ($C_{17}H_{21}N_5O_5$.0.5HCl.1.3$H_2O$)C, H, N.

Example 59

2-(2,6-Dimethoxyphenoxy)ethyl 3-(1-piperazinyl)-2-pyrazinyl ether, Trifluoroacetate The title compound was prepared starting from 2,6-dimethoxyphenol to give 142 mg (30%). HRMS m/z calcd for $C_{18}H_{24}N_4O_4(M)^+$ 360.1798, found 360.1797.

Example 60

2-(2,3-Dimethoxyphenoxy)ethyl 3-(1-piperazinyl)-2-pyrazinyl ether

The title compound was prepared starting from 2,3-dimethoxyphenol to give 110 mg (31%). HRMS m/z calcd for $C_{18}H_{24}N_4O_4(M)^+$360.1798, found 360.1800.

Example 61

2-(2-Acetylphenoxy)ethyl 3-(1-piperazinyl)-2-pyrazinyl ether, Trifluoroacetate

The title compound was prepared starting from 2-hydroxyacetophenone (170 mg, 1.25 mmol) and 2-[3-(4-tert-butoxycarbonyl-1-piperazinyl)-2-pyrazinyloxy]ethanol (325 mg, 1 mmol, prepared in Example 52, Step 2), but no extraction with NaOH and without the third chromatographic step, to give 170 mg (37%) of the trifluoroacetate. HRMS m/z calcd for $C_{18}H_{22}N_4O_3(M)^+$42.1692, found 342.1704.

Example 62

2-(2-Acetyl-5-methoxyphenoxy)ethyl 3-(1-piperazinyl)-2-pyrazinyl ether, Trifluoroacetate The title compound was prepared starting from 2-hydroxy-4-methoxy-acetophenone (208 mg, 1.25 mmol) and 2-[3-(4-tert-butoxycarbonyl-1-piperazinyl)-2-pyrazinyloxy]ethanol (325 mg, 1 mmol; prepared in Example 52, Step 2), but no extraction with NaOH and without the third chromatographic step, to give 128 mg (26%) of the trifluoroacetate. HRMS m/z calcd for $C_{19}H_{24}N_4O_4(M)^+$372.1798, found 372.1810.

Example 63

2-(2-Acetyl-3,5-dimethoxyphenoxy)ethyl 3-(1-piperazinyl)-2-pyrazinyl ether, Trifluoroacetate The title compound was prepared starting from 2-hydroxy-4,6-dimethoxyacetophenone (245 mg, 1.25 mmol) and 2-[3-(4-tert-butoxycarbonyl-1-piperazinyl)-2-pyrazinyloxy]ethanol (325 mg, 1.00 mmol; prepared in Example 52, Step 2), but no extraction with NaOH and without the third chromatographic step, to give 216 mg (42%) of the trifluoroacetate. HRMS m/z calcd for $C_{20}H_{26}N_4O_5(M)^+$402.1903, found 402.1886.

Example 64

2-(5,6,7,8-Tetrahydro-2-naphthyloxy)ethyl 3-(1-piperazinyl)-2-pyrazinyl ether, Trifluoroacetate The title compound was prepared starting from 5,6,7,8-tetrahydro-2-naphthol (185 mg, 1.25 mmol) and 2-[3-(4-tert-butoxycarbonyl-1-piperazinyl)-2-pyrazinyloxy]ethanol (325 mg, 1.00 mmol; prepared in Example 52, Step 2), but no extraction with NaOH and without the third chromatographic step, to give 155 mg (33%) of the trifluoroacetate. HRMS m/z calcd for $C_{20}H_{26}N_4O_2(M)^+$354.2056, found 354.2068.

Example 65

2-(2-Fluoro-6-methoxyphenoxy)ethyl 3-(1-piperazinyl)-2-pyrazinyl ether

The title compound was prepared starting from 2-fluoro-6-methoxyphenol (178 mg, 1.25 mmol) and 2-[3-(4-tert-butoxycarbonyl-1-piperazinyl)-2-pyrazinyloxy]ethanol (1.17 mmol; prepared in Example 52, Step 2) to give 230 mg (66%) of a yellow oil. HRMS m/z calcd for $C_{17}H_{21}FN_4O_3$(M)$^+$348.1598, found 348.1602.

Example 66

2-(2-Methoxy-4-methylphenoxy)ethyl 3-(1-piperazinyl)-2-pyrazinyl ether

The title compound was prepared starting from 2-methoxy-4-methylphenol (162 mg, 1.25 mmol) and 2-[3-(4-tert-butoxycarbonyl-1-piperazinyl)-2-pyrazinyloxy]ethanol (1.00 mmol; prepared in Example 52, Step 2) to give 233 mg (67%) of a yellow solid. HRMS m/z calcd for $C_{18}H_{24}N_4O_3(M)^+$344.1848, found 344.1839.

Example 67

7-Isoquinolinyl 2-{[3-(1-piperazinyl)]-2-pyrazinyl}oxy)ethyl ether, Difumarate

The title compound was prepared starting from 7-hydroxyisoquinoline (435 mg, 3.00 mmol) and 2-[3-(4-tert-butoxycarbonyl-1-piperazinyl)-2-pyrazinyloxy]ethanol (1.00 mmol; prepared in Example 52, Step 2). The free base of the title compound was converted to its fumarate salt. Yield 45 mg (2%); mp 157° C. (dec). HRMS m/z calcd for $C_{19}H_{21}N_5O_2(M)^+$351.1695, found 351.1695. Anal. ($C_{19}H_{21}N_5O_2 \cdot 2.3C_4H_4O_4$).

Example 68

2-(2-Chloro-4-methoxyphenoxy)ethyl 3-(1-piperazinyl)-2-pyrazinyl ether

The title compound was prepared starting from 2-chloro-4-methoxyphenol (103 mg, 0.65 mmol) and 2-[3-(4-tert-butoxycarbonyl-1-piperazinyl)-2-pyrazinyloxy]ethanol (0.61 mmol; prepared in Example 52, Step 2) according to the procedure described in Example 52, Step 3, but utilizing diethyl azodicarboxylate (DEAD) instead of TMAD. Yield 50 mg (21%) HRMS m/z calcd for $C_{17}H_{21}ClN_4O_3(M)^+$ 364.1302, found 364.1307.

Example 69

2-{2-[2-Fluoro-5-(trifluoromethyl)phenoxy]ethoxy}-3-(1-piperazinyl)pyrazine

2-Fluoro-5-(trifluoromethyl)phenol (0.54 g, 3.0 mmol) was added to a stirred solution of DEAD (0.52 g, 3.0 mmol), PPh$_3$ (0.79 g, 3.0 mmol) and 2-[3-(4-tert-butoxycarbonyl-1-piperazinyl)-2-pyrazinyloxy]ethanol (0.49 g, 1.5 mmol; prepared in Example 52, Step 2) in THF (50 mL). The reaction mixture was stirred at room temperature overnight. The solvent was evaporated and the residue was purified by column chromatography on silica using isohexane/EtOAc (80:20) as eluent. The N-Boc protected intermediate obtained was treated with CH$_2$Cl$_2$/TFA (75:25; 5 mL) for 1 h at room temperature and concentrated. The residue was purified by column chromatography on silica using EtOAc/MeOH/Et$_3$N (80:15:5) as eluent to give 0.22% g (38%) of the title compound. MS m/z 387 (M+H)$^+$. HRMS m/z calcd for $C_{17}H_{18}F_4N_4O_2(M)^+$386.1366, found 386.1367.

Example 70

8-(2-{[3-(1-piperazinyl)-2-pyrazinyl]oxy}ethoxy)-2H-1,4-benzoxazin-3(4H)-one, Maleate Step 1: 8-Hydroxy-2H-1,4-benzoxazin-3(4H)-one.

The title compound was prepared according to procedure described in *J. Med. Chem.* 1996, 39, 3533–3538 by replacing 2-amino-m-cresol with 3-amino-pyrocatechol.*The crude product was purified by column chromatography on silica gel using EtOAc/isohexane (1:2 to 2:1) as eluent. Solid; yield 70%. MS m/z 165 (M)$^+$. Anal. ($C_8H_7NO_3$) C, H, N.
*Previously reported in *Liebigs Ann. Chem.* 1957, 608, 128 and *Synth. Commun.* 1997, 27, 1661–1668.

Step 2: 8-(2-{[3-(1-piperazinyl)-2-pyrazinyl]oxy}ethoxy)-2H-1,4-benzoxazin-3(4H)-one, Maleate.

The title compound was prepared according to the procedure of Example 69 starting from the product of Step 1 above. Yield 42%. MS m/z 372 (M+H)$^+$. Anal. ($C_{18}H_{21}N_5O_4.C_4H_4O_4$) C, H, N.

Example 71

2-{2-[3-(Methylsulfonyl)phenoxy]ethoxy}-3-(1-piperazinyl)pyrazine

Step 1: 3-(Methylsulfonyl)phenol.

The title compound was prepared by a slightly modified literature procedure.*3-aminophenyl methyl sulfone hydrochloride (1.18 g, 5.70 mmol) was suspended in water/$CH_2Cl_2$. The mixture was neutralized with 25% aqueous NaOH. The $CH_2Cl_2$ layer was isolated and evaporated to dryness. Aqueous $H_2SO_4$ (60%; 10 mL) was added to the residue and the solution was cooled to 0° C. A solution of $NaNO_2$ (0.345 g, 5.00 mmol) in water (5 mL) was added dropwise. The solution was stirred at 0° C. for 30 min. and at 90° C. for 30 min. The reaction mixture was allowed to come to room temperature. Extraction with $CH_2Cl_2$, drying ($MgSO_4$), and concentration gave 0.39 g (40%) of the title compound as a solid. MS m/z 172 (M)$^+$. HRMS m/z calcd for $C_7H_8O_3S$ (M)$^+$172.0194, found 172.0198.
*J. Chem. Soc. 1938, 899–905.

Step 2. 2-{2-[3-(Methylsulfonyl)phenoxy]ethoxy}-3-(1-piperazinyl)pyrazine.

The title compound was prepared according the procedure of Example 69 starting from the product of Step 1. Yield 26%. MS m/z 379 (M+H)$^+$. HRMS m/z calcd for $C_{17}H_{22}N_4O_4S$ (M)$^+$378.1362, found 378.1343.

Example 72

7-(2-{[3-(1-piperazinyl)-2-pyrazinyl]oxy}ethoxy)-2H-chromen-2-one

The title compound was prepared according to the procedure of Example 69 starting from 7-hydroxy-2H-chromen-2-one. Yield 29%. MS m/z 369 (M+H)$^+$. HRMS m/z calcd for $C_{19}H_{20}N_4O_4$(M)$^+$368.1485, found 368.1478

Example 73

2-(2,3,6-Trifluorophenoxy)ethyl 3-(1-piperazinyl)-2-pyrazinyl ether

The title compound was prepared according to the procedure of Example 69 starting from 2,3,6-trifluorophenol. Yield 46%. MS m/z 355 (M+H)$^+$. HRMS m/z calcd for $C_{16}H_{17}F_3N_4O_2$(M)$^+$354.1304, found 354.1288.

Example 74

2-(2,4,5-Trifluorophenoxy)ethyl 3-(1-piperazinyl)-2-pyrazinyl ether

The title compound was prepared according to the procedure of Example 69 starting from 2,4,5-trifluorophenol. Yield 43%. MS m/z 355 (M+H)$^+$. HRMS m/z calcd for $C_{16}H_{17}F_3N_4O_2$(M)$^+$354.1304, found 354.1304.

Example 75

2-(2-Hydroxyphenoxy)ethyl 3-(1-piperazinyl)-2-pyrazinyl ether

The title compound was prepared according to the procedure of Example 69 starting from catechol. Yield 37%. MS m/z 317 (M+H)$^+$. HRMS m/z calcd for $C_{16}H_{20}N_4O_3$ (M)$^-$316.1535, found 316.1535.

Example 76

2-(3-Hydroxyphenoxy)ethyl 3-(1-piperazinyl)-2-pyrazinyl ether

The title compound was prepared according to the procedure of Example 69 starting from resorcinol. Yield 36%. MS m/z 317 (M+H)$^+$. HRMS m/z calcd for $C_{16}H_{20}N_4O_3$ (M)$^+$316.1535, found 316.1525.

Example 77

2-[3-(4-Morpholinyl)phenoxy]ethyl 3-(1-piperazinyl)-2-pyrazinyl ether 1,1'-Azobis(N,N-dimethylformamide) (TMAD; 256 mg, 1.50 mmol) was added to a solution of 2-[3-(4-tert-butoxycarbonyl-1-piperazinyl)-2-pyrazinyloxy]ethanol (400 mg, 1.24 mmol; prepared in Example 52, Step 2), 3-(4-morpholinyl)phenol (441 mg, 1.23 mmol) and triphenylphosphine (646 mg, 2.46 mmol) in THF (3 mL). The reaction mixture was stirred at room temperature for 2.5 h and then concentrated. The residue was purified by repeated chromatography on silica gel using toluene and toluene/EtOAc (8:2) as eluents. Solvents were evaporated and the residue was treated with $CH_2Cl_2$/TFA/$H_2O$ (1:0.9:0.1; 5 mL) at room temperature for 0.5 h After concentration 5 M NaOH was added followed by extraction with $CH_2Cl_2$. The organic phase was dried ($K_2CO_3$), filtered, and concentrated. The residue was purified by chromatography on silica gel using $CHCl_3$/MeOH (9:1) as eluent to give 50 mg (10%) of the title product as on oil. HRMS m/z calcd for $C_{20}H_{27}N_5O_3$ (M)$^+$385.2114, found 385.2100.

Examples 78–82 were prepared according to the procedure of Example 77 starting from 2-[3-(4-tert-butoxycarbonyl-1-piperazinyl)-2-pyrazinyloxy]ethanol and the requisite phenolic compound.

Example 78

2-(1,3-Benzodioxol-4-yloxy)ethyl 3-(1-piperazinyl)-2-pyrazinyl ether

The title compound was prepared starting from 1,3-benzodioxol-4-ol*(340 mg, 1.24 mmol) to give 125 mg (29%) of an oil. HRMS m/z calcd for $C_{17}H_{20}N_4O_4$(M)$^+$ 344.1485, found 344.1487.
*Prepared as described in *Chem. Pharm. Bull.* 1980, 28, 2414–2421.

Example 79

2-(2,3-Dihydro-1,4-benzodioxin-5-yloxy)ethyl 3-(1-piperazinyl)-2-pyrazinyl ether The title compound was prepared starting from 2,3-dihydro-1,4-benzodioxin-5-ol*(374 mg, 1.24 mmol) to give 260 mg (59%) of a solid: mp 98–99° C. HRMS m/z calcd for $C_{18}H_{22}N_4O_4$(M)$^+$358.1641, found 358.1648.
*Prepared as described in *J. Am. Chem Soc.* 1959, 81, 5199–5201.

Example 80

2-(2-Allylphenoxy)ethyl 3-(1-piperazinyl)-2-pyrazinyl ether

The title compound was prepared starting from 2-allylphenol (330 mg, 1.24 mmol) to give 200 mg (47%) of an oil. HRMS m/z calcd for $C_{19}H_{24}N_4O_2(M)^+$ 340.1899, found 340.1888.

Example 81

2-(3-Aminophenoxy)ethyl 3-(1-piperazinyl)-2-pyrazinyl ether

The title compound was prepared starting from 3-aminophenol (268 mg, 1.24 mmol) to give 49 mg (13%) of an oil. HRMS m/Z calcd for $C_{16}H_{21}N_5O_2(M)^+$ 315.1695, found 315.1705.

Example 82

2-(1-Oxoindanyl-4-yloxy)ethyl 3-(1-piperazinyl)-2-pyrazinyl ether

The title compound was prepared starting from 4-hydroxy-1-indanone (365 mg, 1.24 mmol) to give 19 mg (4%) of an oil. HRMS m/z calcd for $C_{19}H_{22}N_4O_3(M)^+$ 354.1692, found 354.1705.

Example 83

2-(2,6-Difluorophenoxy)ethyl 3-(1-piperazinyl)-2-pyrazinyl ether

The title compound was prepared according to the procedure of Example 77 starting from 2,6-difluorophenol (239 mg, 1.84 mmol), TMAD (384 mg, 2.25 mmol), 2-[3-(4-tert-butoxycarbonyl-1-piperazinyl)-2-pyrazinyloxy]ethanol (600 mg, 1.86 mmol; prepared in Example 52, Step 2), and triphenylphosphine (969 mg, 3.69 mmol) to give 279 mg (45%) of a solid: mp 101–102° C. HRMS m/z calcd for $C_{16}H_{18}F_2N_4O_2(M)^+$ 336.1398, found 336.1403.

Example 84

5-Nitro-8-(2-{[3-(1-piperazinyl)-2-pyrazinyl]oxy}ethoxy)quinoline, Hydrochloride DEAD (0.485 mL, 3.08 mmol) was added to a stirred solution of 2-[3-(4-tert-butoxycarbon)-1-piperazinyl)-2-pyrazinyloxy]ethanol (1.00 g, 3.08 mmol; prepared in Example 52, Step 2), 8-hydroxy-5-nitroquinoline (0.589 g, 3.08 mmol) and PPh$_3$ (0.85 g, 3.24 mmol) in THF (10 mL). The mixture was stirred at room temperature for 2 h, and concentrated. The residue was passed through a silica column using toluene/EtOAc (1:1) as eluent. The N-Boc protected intermediate obtained was treated with CH$_2$Cl$_2$/TFA/H$_2$O (50:45:5; 15 mL) for 30 min at room temperature and concentrated. The residue was dissolved in 0.1 M aqueous HCl and washed with toluene. The water phase was concentrated to give 0.206 g (15%) of the title product. Pos-EI-MS shows M$^+$ and 7 ions supporting the stated structure: HRMS m/z calcd for $C_{19}H_{20}N_6O_4(M)^+$ 396.1546, found 396.1557.

Example 85

6-Methoxy-7-(2-{[3-(1-piperazinyl)-2-pyrazinyl]oxy}ethoxy)-2H-chromen-2-one, Dihydrochloride DEAD (0.50 mL, 3.2 mmol) was added dropwise to a stirred mixture of 2-[3-(4-tert-butoxycarbonyl-1-piperazinyl)-2-pyrazinyloxy]ethanol (1.00 g, 3.08 mmol; prepared in Example 52, Step 2), scopoletin (0.60 g, 3.1 mmol) and triphenylphosphine (0.87 g, 3.3 mmol) in THF (10 mL) at room temperature. After 1 h, the reaction mixture was diluted with EtOAc and washed with water. The organic phase was dried, (MgSO$_4$), concentrated and the residue was purified by column chromatography on silica using toluene/EtOAc (7:3) as eluent. The pure fractions were combined and treated with CH$_2$Cl$_2$/TFA/H$_2$O (50:45:5; 5 mL) for 30 min at room temperature. The mixture was diluted with 0.2 M aqueous HCl and washed with EtOAc (×3). The aqueous layer was concentrated to give 0.075 g (5%) of the title product. Pos-EI-MS shows M$^+$ and 15 ions supporting the stated structure. Anal ($C_{20}H_{22}N_4O_5$·1.3 HCl·1.4H$_2$O)C, H, N.

Example 86

4-(2-{[3-(1-piperazinyl)-2-pyrazinyl]oxy}ethoxy)-2,1,3-benzothiadiazole, Dihydrochloride Step 1: tert-Butyl 4-{3-[2-(2,1,3-benzothiadiazol-4-yloxy)ethoxy]-2-pyrazinyl}-1-piperazinecarboxylate.

DEAD (0.52 mL, 3.3 mmol) was added to a slurry of 2-[3-(4-tert-butoxycarbonyl-1-piperazinyl)-2-pyrazinyloxy]ethanol (1.00 g, 3.08 mmol; prepared in Example 52, Step 2), 4-hydroxy-2,1,3-benzothiadiazole*(0.46 g, 3.0 mmol) and resin bound PPh$_3$ (1.1 g, 3.3 mmol) and shaken until HPLC showed no starting material. The mixture was filtered to remove the resin, concentrated and purified by column chromatography on silica to give 0.163 g (12%) of the title compound. Pos-EI-MS shows M$^+$ and 11 ions supporting the stated structure. HRMS m/z calcd for $C_{21}H_{26}N_6O_4S$ (M)$^+$ 458.1736, found 458.1716.

*The starting material 4-hydroxy-2,1,3-benzothiadiazole was obtained as described in *Khim. Geterotsikl Soedin* 1973, 7, 926–9).

Step 2: 4-(2-{[3-(1-piperazinyl)-2-pyrazinyl]oxy}ethoxy)-2,1,3-benzothiadiazole, Dihydrochloride.

The product from Step 1 above (0.163 g, 0.356 mmol) was treated with CH$_2$Cl$_2$/TFA/H$_2$O (50:45:5; 5 mL) at room temperature for 30 min. The reaction mixture was concentrated and diluted with 0.1 M aqueous HCl and washed with toluene. The water phase was concentrated and the residue crystallized from MeOH/diethyl ether to give 0.088 g (57%) of the title product. Pos-EI-MS shows M$^+$ and 7 ions supporting the stated structure; HRMS m/z calcd for $C_{16}H_{18}N_6O_2S$ (M)$^+$358.1212, found 358.1207. Anal ($C_{18}H_{18}N_6O_2S$·2HCl H$_2$O)C, H, N.

Example 87

8-(2-{[3-(1-piperazinyl)-2-pyrazinyl]oxy}ethoxy)quinazoline, Maleate

DEAD (0.657 mL, 4.00 mmol) was added to a stirred solution of 8-quinazolinol*(0.55 g, 3.76 mmol), 2-[3-(4-tert-butoxycarbonyl-1-piperazinyl)-2-pyrazinyloxy]ethanol (1.216 g, 3.75 mmol; prepared in Example 52, Step 2) and PPh$_3$ (1.048 g, 4.00 mmol) in THF (12 mL). The reaction was stirred at room temperature for 2 h and then poured into 5% aqueous NaOH and extracted with EtOAc. The organic layer was dried (MgSO$_4$) and concentrated. The residue was purified by column chromatography on silica using toluene/EtOAc/MeOH (49:50:1). The pure fractions were combined and treated with CH$_2$Cl$_2$/TFA/H$_2$O (50:45:5; 5 mL) at room temperature for 30 minutes, poured into 0.5 M aqueous HCl and washed with EtOAc. The water phase was alkalinized to pH 12 and extracted with EtOAc, dried (MgSO$_4$), and concentrated to give 0.499 g (1.40 mmol) of the free base of the title compound. The free base was dissolved in dioxane (10 mL), and maleic acid (0.162 g, 1.40 mmol) in dioxane (2 mL) was added and the solution concentrated to give 0.65 g (37%) of the title product. Pos-EI-MS shows M$^+$ and 9 ions supporting the stated structure. Anal (C$_{18}$H$_{20}$N$_6$O$_2$.1.3C$_4$H$_4$O$_4$) C, H, N.

*The starting material 8-quinazolinol was obtained as described in *J. Chem. Soc.* 1952, 4985–4993.

Example 88

5-(2-{[3-(1-Piperazinyl)-2-pyrazinyl]oxy}ethoxy) quinoxaline, Hydrochloride

TMAD (0.55 g, 3.20 mmol) was added to a stirred solution of 2-[3-(4-tert-butoxycarbonyl-1-piperazinyl)-2-pyrazinyloxy]ethanol (1.00 g, 3.08 mmol; prepared in Example 52, Step 2), 5-hydroxyquinoxaline*(0.45 g, 3.08 mmol) and PPh$_3$ (0.85 g, 3.24 mmol) in THF (20 mL). The reaction was stirred at room temperature for 1.5 h and at 65° C. for 2 h. The reaction mixture was concentrated and the residue was purified by column chromatography on silica using toluene/EtOAc (1:1) as eluent. The resulting solid was crystallized twice from diethyl ether/petroleum ether to remove PPh$_3$O. The recrystallized material (0.50 g) was dissolved in MeOH (15 mL) and 1 M HCl (3.5 mL) was added. The resulting mixture was stirred at room temperature for 4 h (only 10% N-Boc-deprotection had occurred according to HPLC/MS). The mixture was concentrated and the residue was treated with CH$_2$Cl$_2$/TFA/H$_2$O (50:45:5; 20 mL) for 1 h. After concentration in vacuo, the residue was dissolved in 0.1 M aqueous HCl and washed with toluene. The water phase was lyophilized to give a yellow oil that was dissolved in 1 M HCl. The solution was concentrated and MeOH and diethyl ether was added. The precipitate formed was collected and dried in vacuum to give 0.32 g (76%) of the title product. Pos-EI-MS shows M$^+$ and 8 ions supporting the stated structure. HRMS m/z calcd for C$_{18}$H$_{20}$N$_6$O$_2$(M)$^+$352.1648, found 352.1662.

*The starting material 5-hydroxyquinoxaline was obtained as described in *J. Org. Chem.* 1951, 16, 438–442.

Example 89

1-[7-(2-{[3-(1-piperazinyl)-2-pyrazinyl] oxy}ethoxy)-1-benzofuran-2-yl]-1-ethanone, Hydrochloride DEAD (0.787 mL, 5.00 mmol) was added to a stirred solution of 2-[3-(4-tert-butoxycarbonyl-1-piperazinyl)-2-pyrazinyloxy]ethanol (1.50 g, 4.63 mmol; prepared in Example 52, Step 2), 2-acetyl-7-hydroxybenzofuran (0.88 g, 5.0 mmol) and PPh$_3$ (1.31 g, 5.0 mmol) in THF (3 mL) under gentle heating. After being stirred for 30 min at room temperature, the reaction mixture was poured into water, extracted with EtOAc, dried (MgSO$_4$) and concentrated. The residue was purified by column chromatography oil silica using toluene/EtOAc (7:3) as eluent. The pure fractions were combined and treated with CH$_2$Cl$_2$/TFA/H$_2$O (50:45:5; 5 mL) for 30 min at room temperature. The mixture was poured into 0.5 M aqueous HCl and washed with EtOAc. The aqueous layer was alkalinized, by addition of NaOH, to pH 12 and extracted with EtOAc. The organic layer was dried (MgSO$_4$), filtered and concentrated. The residue (0.250 g, 0.65 mmol) and pyridinium hydrochloride (0.075 g, 0.65 mmol) was dissolved in MeOH. The mixture was and concentrated and the residue was re-dissolved in EtOH and concentrated three more times to give 0.27 g (14%) of the title product. Pos-EI-MS shows M$^+$ and 19 ions supporting the stated structure. HRMS m/z calcd for C$_{20}$H$_{22}$N$_4$O$_4$(M)$^+$ 382.1641, found 382.1631.

Example 90

3-(Phenoxy)propyl 3-(1-piperazinyl)-2-pyrazinyl ether, Dihydrochloride

Step 1: 2-Chloro-3-(1-piperazinyl)pyrazine.*

A mixture of 2,3-dichloropyrazine (1.35 g, 15.32 mmol), piperazine (2.34 g, 27.2 mmol) and K$_2$CO$_3$ (1.25 g, 9.04 mmol) in acetonitrile (5.5 mL) was stirred at 110° C. for 1.25 h in a sealed tube. The reaction mixture was diluted with CH$_2$Cl$_2$, filtered, and concentrated to give a yellowish semisolid residue which was purified by chromatography on silica gel using CHCl$_3$/MeOH (9:1) as eluent. The obtained solid was redissolved in CHCl$_3$ and applied to a short (3 cm) plug of alumina. Elution with ether/CHCl$_3$ (9:1) afforded 1.24 g (69%) of the title product as a white solid: mp 47–53° C. HRMS m/z calcd for C$_8$H$_{11}$ClN$_4$(M)$^+$198.0672, found 198.0673.

*Previously reported in *J. Med. Chem.* 1978, 21, 536–542.

Step 2: 3-(Phenoxy)propyl 3-(1-piperazinyl)-2-pyrazinyl ether, Dihydrochloride.

2-Chloro-3-(1-piperazinyl)pyrazine (608 mg, 3.1 mmol; from Step 1 above) and 3-phenoxypropanol (570 mg, 3.7 mmol) was dissolved in dioxane (10 mL). KO-t-Bu (870 mg, 7.7 mmol) was added and the mixture was stirred at 95° C. for 6 h. The solvent was evaporated and the residue was purified by chromatography on silica gel using CH$_2$Cl$_2$/MeOH (9:1) as eluent to give the free base of the title compound as a yellow oil. The free base was converted to the dihydrochloride salt: yield 0.380 g (32%): mp 146–146.5° C. Anal. (C$_{17}$H$_{22}$N$_4$O$_2$.2HCl) C, H, N.

Examples 91–161 were prepared according to the procedure of Example 90, Step 2, starting from 2-chloro-3-(1-piperazinyl)pyrazine and the appropriate alcohol. Purification was by column chromatography on silica gel using CHC$_3$/MeOH (9:1) or CHCl$_3$/MeOH/NH$_4$OH (95:5:0.5) or other appropriate solvent system.

Example 91

2-(2-Trifluoromethylphenoxy)ethyl 3-(1-piperazinyl)-2-pyrazinyl ether

Step 1: 2-(2-Trifluoromethylphenoxy)ethanol.

A mixture of 2-trifluoromethylphenol (2.00 g, 12.3 mmol), K$_2$CO$_3$ (1.71 g, 12.3 mmol) and ethylene carbonate (1.20 g, 13.6 mmol) in dry DMF (30 mL) was heated at 150° C. for 1 h. After cooling, the reaction was quenched by addition of water (10 mL). The mixture was concentrated in vacuo and the residue partitioned between water (30 mL) and EtOAc (30 mL). The aqueous phase was extracted with additional portions of EtOAc (3×30 mL). The combined organic layers were treated with charcoal, dried over MgSO$_4$, and filtered through Celite. The filtrate was concentrated in vacuo and the remaining oil was purified by chromatography on silica gel using n-hexane/EtOAc (80:20) as eluent to give 0.50 g (20%) of the title product as white crystals: mp 74–77° C. Anal. (C$_9$H$_9$F$_3$O$_2$) C, H.

Step 2: 2-(2-Trifluoromethylphenoxy)ethyl 3-(1-piperazinyl)-2-pyrazinyl ether.

Yield 48%, mp 79–80° C. Anal. (C$_{17}$H$_{19}$F$_3$N$_4$O$_2$) C, H, N.

Example 92

2-(2-Methylthiophenoxy)ethyl 3-(1-piperazinyl)-2-pyrazinyl ether, Maleate

Step 1: 2-(2-Methylthiophenoxy)ethanol.*

The title compound was prepared according to the procedure described in Example 91, Step 1, starting from 2-(methylthio)phenol. Yield 63%: nip 47–49° C. Anal. ($C_9H_{12}O_2S$) C, H.

*Previously described in U.S. Pat. No. 3,932,498.

Step 2: 2-(2-Methylthiophenoxy)ethyl 3-(1-piperazinyl)-2-pyrazinyl ether, Maleate.

Yield 68%; mp 160–162° C. Anal. ($C_{17}H_{22}N_4O_2S.C_4H_4O_4.0.1$ THF) C, H, N.

Example 93

2-(2-Methylphenoxy)ethyl 3-(1-piperazinyl)-2-pyrazinyl ether, Maleate

Step 1: 2-(2-Methylphenoxy)ethanol.*

The title compound was prepared according to the procedure described in Example 91, Step 1, starting from o-cresol. Oil; yield 59%. HRMS m/z calcd for $C_9H_{12}O_2$ (M)$^+$ 152.0837, found 152.0840.

*Previously described in Tetrahedron 1996, 52, 177–184.

Step 2: 2-(2-Methylphenoxy)ethyl 3-(1-piperazinyl)-2-pyrazinyl ether, Maleate.

Yield 33%; mp 151–152° C. Anal. ($C_{17}H_{22}N_4O_2.C_4H_4O_4.0.5H_2O$) C, H, N.

Example 94

2-(2,5-Dimethylphenoxy)ethyl 3-(1-piperazinyl)-2-pyrazinyl ether

Step 1: 2-(2,5-Dimethylphenoxy)ethanol.*

The title compound was prepared according to the procedure described in Example 91, Step 1, starting from 2,5-dimethylphenol. Yield 60%; mp 45–48° C. Anal. ($C_{10}H_{14}O_2$) C, H.

*Previously described in J. Chem. Soc. 1914, 2117–2139.

Step 2: 2-(2,5-Dimethylphenoxy)ethyl 3-(1-piperazinyl)-2-pyrazinyl ether.

Oil, yield 65%. Anal. ($C_{18}H_{24}N_4O_2$) C, H, N.

Example 95

2-(2-Fluorophenoxy)ethyl 3-(1-piperazinyl)-2-pyrazinyl ether, Maleate

Step 1: 2-(2-Fluorophenoxy)ethanol.*

The title compound was prepared according to the procedure described in Example 91, Step 1, starting from 2-fluorophenol. Oil; yield 71%. MS m/z 156 (M)$^+$.

*Previously described in J. Indian Chem. Soc. 1962, 39, 5–8.

Step 2: 2-(2-Fluorophenoxy)ethyl 3-(1-piperazinyl)-2-pyrazinyl ether, Maleate.

Yield 46%, mp 171–173° C. Anal. ($C_{16}H_{19}FN_4O_2.C_4H_4O_4$) C, H, N.

Example 96

2-(2-Cyanophenoxy)ethyl 3-(1-piperazinyl)-2-pyrazinyl ether, Maleate

Step 1: 2-(2-Cyanophenoxy)ethanol.*

The title compound was prepared according to the procedure described in Example 91, Step 1, starting from 2-cyanophenol. Oil; yield 26%. MS m/z 163 (M)$^+$.

*Previously described in J. Chem. Soc. 1914, 2117–2139.

Step 2: 2-(2-Cyanophenoxy)ethyl 3-(1-piperazinyl)-2-pyrazinyl ether, Maleate.

Yield 40%; mp 165–166° C. Anal. ($C_{17}H_{19}N_5O_2.C_4H_4O_4$) C, H, N.

Example 97

2-[(1,1'Biphenyl)-2-yloxy]ethyl 3-(1-piperazinyl)-2-pyrazinyl ether

Step 1: 2-[(1,1'Biphenyl)-2-yloxy]ethanol.*

The title compound was prepared according to the procedure described in Example 91, Step 1, starting from 2-phenylphenol. Yield 52%; mp 71–75° C. Anal. ($C_{14}H_{14}O_2$) C, H.

*Previously described in J. Med. Chem. 1987, 30, 939–943.

Step 2: 2-[(1,1'Biphenyl)-2-yloxy]ethyl 3-(1-piperazinyl)-2-pyrazinyl ether.

Yield 53%; mp 101–103° C. Anal. ($C_{22}H_{24}N_4O_2$) C, H, N.

Example 98

4-(Phenoxy)butyl 3-(1-piperazinyl)-2-pyrazinyl ether, Dihydrochloride.*

Yield 49%; mp 129–131° C. Anal. ($C_{18}H_{24}N_4O_2.2HCl$) C, H, N.

*The starting material 4-phenoxybutanol was obtained as described in J. Org. Chem. 1965, 30, 2441–2447.

Example 99

2-[2-(2-Fluoro-5-methylphenoxy)ethoxy]-3-(1-piperazinyl)pyrazine, Fumarate

Step 1: 2-(2-Fluoro-5-methylphenoxy)ethanol.

The title compound was prepared according to the procedure described in Example 91. Step 1, starting from 2-fluoro-5-methylphenol. Oil; yield 94%. MS m/z 170 (M)$^+$.

Step 2: 2-[2-(2-Fluoro-5-methylphenoxy)ethoxy]-3-(1-piperazinyl)pyrazine, Fumarate.

Yield 71%; mp 145–146° C. Anal. ($C_{21}H_{25}FN_4O_6.0.3H_2O$) C, H, N.

Example 100

2-[2-(5-Fluoro-2-methoxyphenoxy)ethoxy]-3-(1-piperazinyl)pyrazine, Fumarate

Step 1: 2-(5-Fluoro-2-methoxyphenoxy)ethanol*.

The title compound was prepared according to the procedure described in Example 91, Step 1, starting from 5-fluoro-2-methoxyphenol**. Yield 89%. MS m/z 186 (M)$^+$. Anal. ($C_9H_{11}FO_3$) C, H.

*Previously described in EP 331943.
**Prepared as described in Bull. Soc. Chim. Belg. 1993, 102, 217–226.

Step 2: 2-[2-(5-Fluoro-2-methoxyphenoxy)ethoxy]-3-(1-piperazinyl)pyrazine, Fumarate.

Yield 76%; mp 172–176° C. Anal. ($C_{17}H_{21}FN_4O_3.C_4H_4O_4.0.3H_2O$) C, H, N.

Example 101

2-[2-(3-Fluorophenoxy)ethoxy]-3-(1-piperazinyl)pyrazine, Maleate

Step 1: 2-(3-Fluorophenoxy)ethanol*.

The title compound was prepared according to the procedure described in Example 91, Step 1, starting from 3-fluorophenol. Oil; yield 83%. MS m/z 156 (M)$^+$.

*Previously described in Magn. Reson. Chem. 1992, 30, 723–732.

Step 2: 2-[2-(3-Fluorophenoxy)ethoxy]-3-(1-piperazinyl)pyrazine, Maleate.

Solid, yield 51%; mp 141–143° C. Anal. ($C_{16}H_{19}FN_4O_2.C_4H_4O_4$) C, H, N.

Example 102

2-[2-(3-Methoxyphenoxy)ethoxy]-3-(1-piperazinyl) pyrazine, p-Toluenesulfonate

Step 1: 2-(3-Methoxyphenoxy)ethanol*.

The title compound was prepared according to the procedure described in Example 91. Step 1, starting from 3-methoxyphenol. Oil; yield 64%; MS m/z 168 (M)$^+$. Anal. ($C_9H_{12}O_3$) C, H.

*Previously described in *J. Chem. Soc.* 1935, 1098–1101 and in U.S. Pat. No. 5,025,031.

Step 2: 2-[2-(3-Methoxyphenoxy)ethoxy]-3-(1-piperazinyl)pyrazine, p-Toluenesulfonate.

Solid; yield 20%; mp 131–133° C. Anal. ($C_{17}H_{22}N_4O_3.C_7H_8O_3S$)C, H, N.

Example 103

2-[2-(3-Acetylphenoxy)ethoxy]-3-(1-piperazinyl) pyrazine

Step 1: 2-(3-Acetylphenoxy)-1-ethanol.*

The title compound was prepared according to the procedure described in Example 91. Step 1, starting from 3-hydroxyacetophenone. Oil; yield 82%. MS m/z 180 (M)$^+$. HRMS m/z calcd for $C_{10}H_{12}O_3$(M)$^+$180.0786, found 180.0787.

*Previously described in *Helv. Chim Acta* 1989, 72, 1216–1224.

Step 2: 2-[2-(3-Acetylphenoxy)ethoxy]-3-(1-piperazinyl)pyrazine, Maleate.

Yield of free base 68%. Part of the free base was converted to the maleate salt. MS m/z 343 (M+H)$^+$. Anal. ($C_{18}H_{22}N_4O_3.C_4H_4O_4$) C, H, N.

Example 104

2-[2-(3-Cyanophenoxy)ethoxy]-3-(1-piperazinyl) pyrazine

Step 1:2-(3-Cyanophenoxy)-1-ethanol.*

The title compound was prepared according to the procedure described in Example 91. Step 1, starting from 3-cyanophenol. Oil: yield 63%. MS m/z 163 (M)$^-$. Anal. ($C_9H_9NO_2$)C, H, N.

*Previously described *J. Chem. Soc.* 1914.2117–2139 and *Pharmazie* 1975.30.353–357.

Step 2: 2-[2-(3-Cyanophenoxy)ethoxy]-3-(1-piperazinyl)pyrazine. Solid; yield 74%. MS m/z 326 (M+H)$^+$. Anal. ($C_{17}H_{19}N_5O_2$) C, H, N.

Example 105

2-[2-(2,3-Difluorophenoxy)ethoxy]-3-(1-piperazinyl)pyrazine, Fumarate

Step 1: 2-(2,3-Difluorophenoxy)-1-ethanol.

The title product was prepared according to the procedure described in Example 91, Step 1, starting from 2,3-difluorophenol. Oil; yield 92%. MS m/z 174 (M)$^+$. Anal ($C_8H_8F_2O_2$) C, H.

Step 2: 2-[2-(2,3-Difluorophenoxy)ethoxy]-3-(1-piperazinyl)pyrazine, Fumarate.

Yield 35%; mp 125–130° C. Anal. ($C_{16}H_{18}F_2N_4O_2.C_4H_4O_4$) C, H, N.

Example 106

2-[2-(2,3,5-Trifluorophenoxy)ethoxy]-3-(1-piperazinyl)pyrazine, Fumarate

Step 1: 2-(2,3,5-Trifluorophenoxy)-1-ethanol.

The title product was prepared according to the procedure described in Example 91, Step 1, starting from 2,3,5-trifluorophenol. Oil; yield 83%. MS m/z 192 (M)$^+$. Anal. ($C_8H_7F_3O_2$) C, H.

Step 2: 2-[2-(2,3,5-Trifluorophenoxy)ethoxy]-3-(1-piperazinyl)pyrazine, Fumarate.

Yield 35%; mp 158–159° C. MS m/z 354 (M)$^+$; HRMS m/z calcd for $C_{16}H_{17}F_3N_4O_2$(M)$^+$354.1304, found 354.1303. Anal. ($C_{16}H_{17}F_3N_4O_2.C_4H_4O_4$) C, H, N.

Example 107

N-Phenyl-3-(2-{[3-(1-piperazinyl)-2-pyrazinyl] oxy}ethoxy)aniline, Fumarate

Step 1: 2-(3-Anilinophenoxy)-1-ethanol.*

The title product was prepared according to the procedure described in Example 91. Step 1, starting from 3-anilinophenol. Oil: yield 75% HRMS m/z calcd for $C_{14}H_{15}NO_2$(M)$^+$229.1103, found 229.1111.

*Previously described in U.S. Pat. No. 2,077,322 and EP 585500.

Step 2: N-Phenyl-3-(2-{[3-(1-piperazinyl)-2-pyrazinyl] oxy}ethoxy)aniline, Fumarate.

Yield of free base 24%. Part of the base was converted into its fumarate salt: mp 78–81° C.; HRMS m/z calcd for $C_{22}H_{25}N_5O_2$(M)$^+$391.2008, found 391.2001. Anal ($C_{22}H_{25}N_5O_2.C_4H_4O_4$) C, H, N.

Example 108

[3-(2-{[3-(1-piperazinyl)-2-pyrazinyl]oxy}ethoxy) phenyl]methanol, Maleate

Step 1: 3-(2-Hydroxyethoxy)benzaldehyde*

The title product was prepared according to the procedure described in Example 91, Step 1, starting from 3-hydroxybenzaldehyde. Oil; yield 88%; MS m/z 166 (M)$^+$. Anal. ($C_9H_{10}O_3.0.2H_2O$)C, H, N.

*Previously described in WO 9733202.

Step 2: 2-[3-(Dimethoxymethyl)phenoxy]-1-ethanol.

p-TsOH (165 mg, 0.87 mmol) was added to a solution of the product obtained in Step 1 (1.45 g, 8.73 mmol) in dry MeOH (60 mL). After being stirred for 23 h at room temperature, more p-TsOH (170 mg, 0.89 mmol) was added. After additional 4 h of stirring, the reaction was quenched by the addition of NaHCO$_3$ (saturated aqueous solution, 70 mL) and H$_2$O (50 mL). The aqueous phase was extracted with EtOAc (3×100 mL). The combined organic phases were washed with brine and dried (MgSO$_4$). Evaporation of the solvents afforded a yellow oil that was used in the next step without purification. Yield 1.59 g (86%). The product contained about 5% of starting material ($^1$H NMR).

Step 3: 2-{2-[3-(Dimethoxymethyl)phenoxy]ethoxy}-3-(1-piperazinyl)pyrazine.

Oil, yield 63%: MS m/z 344 (M—CH$_2$O)$^-$. HRMS m/z calcd for $C_{18}H_{24}N_4O_3$(M—CH$_2$O)$^+$344.1848, found 344.1847.

Step 4: 3-(2-{[3-(1-piperazinyl)-2-pyrazinyl]oxy}ethoxy) benzaldehyde.

HOAc (12 mL) and H$_2$O (4 mL) was added to a solution of the product obtained in Step 3 (858 mg, 2.29 mmol) in THF (4 mL). The reaction mixture was stirred at 45° C. for 1.5 h and then diluted with EtOAc (150 mL). The organic phase was washed with brine (x 2), aqueous saturated NaHCO$_3$ and brine. Drying (MgSO$_4$) followed by evaporation of the solvents afforded the title product (0.41 g) as an acetate salt (1.7·HOAc as determined by $^1$H NMR). This product was used in the next step without purification.

Step 5: [3-(2-{[3-(1-piperazinyl)-2-pyrazinyl]oxy}ethoxy) phenyl]methanol, Maleate.

The product obtained in Step 4 (408 mg, 1.24 mmol) was dissolved in EtOH (99%, 35 mL). Immediately upon addition of NaBH$_4$ (293 mg, 7.75 mmol) the solution turned white. The reaction mixture was stirred at room temperature for 5 h and then quenched by addition of H$_2$O (7 mL). The mixture was filtered, and the filtrate diluted with aqueous saturated NaCl (30 mL) and H$_2$O (20 mL). The aqueous solution was extracted with EtOAc (×4). The combined organic phases were washed with brine and dried (MgSO$_4$). Evaporation of the solvents gave a semi-solid residue (330 mg) that was purified by column chromatography on silica using gradient elution with EtOAc/MeOH (9:1)+1% NH$_3$ to EtOAc/MeOH (8:2)+1% NH$_3$. This afforded 76 mg (16%) of the free base of the title product as a semi-solid which was converted to its maleate salt: mp 123.2–123.5° C.; MS m/z 331 (M+H)$^+$. HRMS m/z calcd for C$_{17}$H$_{22}$N$_4$O$_3$(M)$^+$ 330.1692, found 330.1692.

Example 109

2-{2-[3-(Methoxymethyl)phenoxy]ethoxy}-3-(1-piperazinyl)pyrazine, Maleate

Step 1: 2-[(3-(Methoxymethyl)phenoxy]-1-ethanol.

Et$_3$SiH (4.0 mL, 25.0 mmol) was added to a solution of the product of Example 108. Step 1 (1.33 g, 8.00 mmol) in MeOH (14 mL). The mixture was cooled to 0° C. and concentrated H$_2$SO$_4$ (1.5 mL) was added dropwise over 1.5 min. The reaction mixture was stirred at room temperature for 4.5 h. More Et$_3$SiH (1.5 mL, 9.4 mmol) was added, and the stirring was continued for 1 h. After solvent removal in vacuo. H$_2$O was added to the residue and pH was adjusted to pH 4 by addition of 2 M aqueous NaOH. The aqueous solution was extracted with CH$_2$Cl$_2$ (×3). The combined organic phases were washed with brine, dried (MgSO$_4$) and concentrated to give an oil (1.8 g). NMR analysis of the crude product showed only 40% conversion. Therefore, the procedure was repeated by treating the residue with Et$_3$SiH (3 mL), MeOH (8 mL) and concentrated H$_2$SO$_4$ (1.2 mL). After being stirred for 4 h at room temperature more H$_2$SO$_4$ (1.2 mL) was added. The stirring was continued for a further hour and worked up as above. The crude product was purified by column chromatography on silica [gradient 100% isohexane to isohexane/EtOAc (1:1)] to give the title compound as a colorless oil. Yield 0.98 g (67%); MS m/z 182 (M)$^+$. Anal. (C$_{10}$H$_{14}$O$_3$.0.1H$_2$O) C, H.

Step 2: 2-{2-[3-(Methoxymethyl)phenoxy]ethoxy}-3-(1-piperazinyl)pyrazine, Maleate.

Yield of free base of the title compound 0.61 g (80%). Part of this material was converted to the maleate salt: mp 114–115° C.; MS m/z 345 (M+H)$^+$. Anal. (C$_{18}$H$_{24}$N$_4$O$_3$.C$_4$H$_4$O$_4$) C, H, N.

Example 110

3-(2-{[3-(1-piperazinyl)-2-pyrazinyl]oxy}ethoxy)benzamide, Maleate

Step 1: 3-(2-Hydroxyethoxy)benzamide.*

The title compound was prepared according to the procedure described in Example 91, Step 1, starting from 3-hydroxybenzamide. Yield 62%; MS m/z 181 (M)$^+$. HRMS m/z calcd for C$_9$H$_{11}$NO$_3$(M)$^+$181.0739, found 181.0739.
*Previously reported in WO 8606628.

Step) 2: 3-(2-{[3-(1-Piperazinyl)-2-pyrazinyl]oxy}ethoxy)benzamide, Maleate.

Yield of free base of the title compound 43%. The maleate salt was prepared: mp 134–137° C. MS m/z 344 (M+H)$^+$. Anal. (C$_{17}$H$_{21}$N$_5$O$_3$.C$_4$H$_4$O$_4$) C, H, N.

Example 111

N-Phenyl-4-(2-{[3-(1-piperazinyl)-2-pyrazinyl]oxy}ethoxy)aniline, Maleate

Step 1: 2-(4-Anilinophenoxy)ethanol.*

The title product was prepared according to the procedure described in Example 91, Step 1, starting from 4-anilinophenol. Solid; yield 0.85 g (75%); MS m/z 229 (M)$^+$. Anal. (C$_{14}$H$_{11}$NO$_2$) C, H, N.
*Previously described in EP 420790.

Step 2: N-Phenyl-4-(2-{[3-(1-piperazinyl)-2-pyrazinyl]oxy}ethoxy)aniline, Maleate.

Yield of free base of the title compound 44%. The maleate salt was prepared: mp 132–133° C.; MS m/z 392 (M+H)$^+$. Anal. (C$_{22}$H$_{25}$N$_5$O$_2$.C$_4$H$_4$O$_4$) C, H, N.

Example 112

Step 1: N-[4-(2-Hydroxyethoxy)phenyl]acetamide.*

The title product was prepared according to the procedure described in Example 91, Step 1, starting from 4-acetamidophenol. Solid; yield 1.38 g (52%); MS m/z 195 (M)$^+$. Anal. (C$_{10}$H$_{13}$NO$_3$.0.1H$_2$O)C, H, N.
*Previously described in J. Heterocycl. Chem. 1994, 31, 457–480.

Step 2: N-[4-(2-{[3-(1-piperazinyl)-2-pyrazinyl]oxy}ethoxy)phenyl]acetamide.

Solid; yield 0.47 g (53%); MS m/z 357 (M)$^+$. HRMS m/z calcd for C$_{18}$H$_{23}$N$_5$O$_3$(M)$^+$357.1801, found 357.1810.

Example 113

2-(1-Piperazinyl)-3-{2-[3-(trifluoromethoxy)phenoxy]ethoxy}pyrazine, Maleate

Step 1: 2-[3-(Trifluoromethoxy)phenoxy]ethanol.

The title product % vas prepared according to the procedure described in Example 91, Step 1, starting from 3-trifluoromethoxyphenyl. Oil: yield 0.75 g (60%): MS m/z 222 (M)$^+$. Anal. (C$_9$H$_9$F$_3$O$_3$) C, H.

Step 2: 2-(1-piperazinyl)-3-{2-[3-(trifluoromethoxy)phenoxy]ethoxy}pyrazine, Maleate.

Yield of free base of the title compound 61%. The maleate salt was prepared: mp 150–152° C.; MS m/z 326 (M+H)$^+$. Anal. (C$_{17}$H$_{19}$N$_5$O$_2$.C$_4$H$_4$O$_4$) C, H, N.

Example 114

2-[2-(3,5-Difluorophenoxy)ethoxy]-3-(1-piperazinyl)pyrazine, p-Toluenesulfonate

Step 1: 2-(3,5-Difluorophenoxy)-1-ethanol.

In a sealed Pyrex tube, a mixture of 3,5-difluorophenol (2.19 g, 16.8 mmol), ethylene carbonate (1.0 g, 11.4 mmol), a catalytic amount of NaH (60% in mineral oil) in DMF (1 mL) was reacted in a Labwell MW-10 microwave reactor at 50 W for 3 min. The reaction mixture was diluted with toluene and washed with 5% aqueous NaOH. The organic phase was dried (MgSO$_4$) and concentrated: This gave 1.59 g (80%) of the title compound as a light red oil. MS m/z 174 (M)$^+$.

Step 2: 2-[2-(3,5-Difluorophenoxy)ethoxy]-3-(1-piperazinyl)pyrazine p-Toluenesulfonate.

Yield 14%; mp 118–119° C. Anal. (C$_{16}$H$_{18}$F$_2$N$_4$O$_2$.C$_7$H$_8$O$_3$S)C, H, N.

Example 115

2-[2-(1,3-Benzodioxol-S-yloxy)ethoxy]-3-(1-piperazinyl)pyrazine

Step 1: 2-(1,3-Benzodioxol-5-yloxy)ethanol.*

The title compound was prepared according to the procedure of Example 114, Step 1 starting from sesamol (2.0 g, 14.5 mmol) and ethylene carbonate (1.0 g, 11.4 mmol): solid; yield 99%. MS m/z 182 (M)$^+$.

*Previously described in *J. Org. Chem.* 1960, 25, 626–632.

Step 2: 2-[2-(1,3-Benzodioxol-5-yloxy)ethoxy]-3-(1-piperazinyl)pyrazine.

Solid: yield 71%. MS m/z 345 (M+H)$^+$. Anal. ($C_{17}H_{20}N_4O_4$) C, H, N.

Example 116

2-[2-(3-Butoxyphenoxy)ethoxy]-3-(1-piperazinyl) pyrazine, Maleate

Step 1: 2-(3-Butoxyphenoxy)ethanol.

The title compund was prepared according to the procedure of Example 114, Step 1 starting from 3-n-butoxyphenol (2.0 g, 12 mmol) and ethylene carbonate (0.88 g, 10 mmol). Oil; yield 85%. MS m/z 210 (M)$^+$.

Step 2: 2-[2-(3-Butoxyphenoxy)ethoxy]-3-(1-piperazinyl)pyrazine, Maleate.

Yield of free base of the title compound 77%. Part of the free base was converted to the maleate salt. MS m/z 373 (M+H)$^+$. Anal. ($C_{20}H_{28}N_4O_3 \cdot C_4H_4O_4$) C, H, N.

Example 117

2-[2-(3-Trifluoromethylphenoxy)ethoxy]-3-(1-piperazinyl)pyrazine

Step 1: 2-(3-Trifluoromethylphenoxy)ethanol.

The title compound was prepared according to the procedure of Example 114, Step 1 starting from 3-trifluoromethylphenol (3.89 g, 24 mmol) and ethylene carbonate (1.76 g, 20 mmol) with the exception that no DMF was used. Oil; yield 64%. MS m/z 206 (M)$^+$.

Step 2: 2-[2-(3-Trifluoromethylphenoxy)ethoxy]-3-(1-piperazinyl)pyrazine, Maleate.

Yield of free base of the title compound 65%. Part of the free base was converted to the maleate salt. MS m/z 369 (M+H)$^+$. HRMS m/z calcd for $C_{17}H_{19}F_3N_4O_2$(M)$^+$ 368.1460, found 368.1460.

Example 118

2-[2-([1,1'-Biphenyl]-3-yloxy)ethoxy]-3-(1-piperazinyl)pyrazine, Maleate

Step 1: 2-(3-Phenylphenoxy)ethanol.*

The title compound was prepared according to the procedure of Example 114, Step 1 starting, from 3-phenylphenol (1.72 g, 0.1 mmol) and ethylene carbonate (0.80 g, 9.1 mmol) and DMF (3 mL). Semi-solid; yield 86%. MS m/z 214 (M)$^+$.

*Previously described in U.S. Pat. No. 2,140,824.

Step 2: 2-[2-([1,1'-Biphenyl]-3-yloxy)ethoxy]-3-(1-piperazinyl)pyrazine, Maleate.

Yield of free base 70%. Part of the free base was converted to the maleate salt. MS m/z 377 (M+H)$^+$. Anal. ($C_{22}H_{24}N_4O_2 \cdot C_4H_4O_4$) C, H, N.

Example 119

2-[2-(3-Acetamidophenoxy)ethoxy]-3-(1-piperazinyl)pyrazine, Maleate

Step 1: 2-(3-Acetamidophenoxy)-1-ethanol*.

The title product was prepared according to the procedure described in Example 114, Step 1, starting from 3-acetamidophenol (2.10 g, 13.9 mmol) and ethylene carbonate (0.88 g, 10 mmol). The crude product was purified by column chromatography on silica using toluene/EtOAc/MeOH (49:49:2). Oil; yield 99%. MS m/z 195 (M)$^+$.

*Previously described in *J. Am. Chem. Soc.* 1939, 61, 355–357.

Step 2: 2-[2-(3-Acetamidophenoxy)ethoxy]-3-(1-piperazinyl)pyrazine, Maleate.

Yield 38%; mp 154–155° C. Anal. ($C_{18}H_{23}N_5O_3 \cdot C_4H_4O_4$) C, H, N.

Example 120

2-[4-(2-{[3-(1-piperazinyl)-2-pyrazinyl]oxy}ethoxy) phenoxy]ethanol, Maleate

The title product was prepared from 1,4-bis(2-hydroxyethoxy)benzene. Yield of free base of the title compound 51%. The maleate salt was prepared: mp 127–129° C. MS m/z 361 (M+H). Anal. ($C_{18}H_{24}N_4O_4 \cdot C_4H_4O_4$) C, H, N.

Example 121

2-[3-(2-{[3-(1-Piperazinyl)-2-pyrazinyl]oxy}ethoxy) phenoxy]ethanol, Maleate

The title product wasp prepared from 1,3-bis(2-hydroxyethoxy)benzene. Yield of free base of the title compound 45%. The maleate salt was prepared: nip 111–114° C.; MS m/z 361 (M+H)$^+$. Anal. ($C_{18}H_{24}N_4O_4 \cdot C_4H_4O_4 \cdot 0.1H_2O$) C, H, N.

Example 122

2-(Benzofuran-2-ylmethoxy)-3-(1-piperazinyl) pyrazine, Hydrochloride.*

Yield 44%; nip 160–161° C. Anal. ($C_{17}H_{18}N_4O_2 \cdot HCl$) C, H, N.

*The starting material benzofuran-2-ylmethanol was obtained from benzofuran-2-carboxaldehyde by reduction with sodium borohydride.

Example 123

2-(2,3-Dihydrobenzofuranyl-2-ylmethoxy)-3-(1-piperazinyl)pyrazine, Dihydrochloride Yield 33%; mp 172–174° C. Anal. ($C_{17}H_{20}N_4O_2 \cdot 2HCl$) C, H, N. The starting material 2,3-dihydrobenzofuran-2-ylmethanol*was obtained from benzofuran-2-carboxaldehyde by reduction with sodium borohydride and subsequent catalytic hydrogenation.*Previously described in *Bioorg. Med. Chem. Lett.* 1999, 9, 401–406.

Example 124

2-(1-Piperazinyl)-3-(tetrahydro-2-furanylmethoxy) pyrazine, Hydrochloride

The title compound was prepared starting from tetrahydrofurfuryl alcohol. Yield 65%; mp 130–136° C. Anal. ($C_{13}H_{20}N_4O_2 \cdot HCl \cdot H_2O$)C, H, N.

Example 125

2-(1-piperazinyl)-3-[3-(2-pyridinyl)propoxy] pyrazine, Maleate

The title compound was prepared starting from 2-pyridinepropanol. Yield 51% nip 147–148° C. Anal. ($C_{16}H_{21}N_5O \cdot 1.05C_4H_4O_4$) C, H, N.

Example 126

2-(1-piperazinyl)-3-[3-(3-pyridinyl)propoxy] pyrazine, Maleate

The title compound was prepared starting from 3-pyridinepropanol. Yield 43%; mp 128–130° C. Anal. ($C_{16}H_{21}N_5O \cdot C_4H_4O_4$) C, H, N.

Example 127

2-(1-piperazinyl)-3-[3-(4-pyridinyl)propoxy] pyrazine, Maleate

The title compound was prepared starting from 4-pyridinepropanol. Yield 41%; mp 90–91° C. Anal. ($C_{16}H_{21}N_5O \cdot C_4H_4O_4 \cdot 0.7H_2O$) C, H, N.

Example 128

2-[3-(6-Methyl-2-pyridinyl)propoxy]-3-(1-piperazinyl)pyrazine, Maleate

The title compound was prepared starting from 6-methyl-2-pyridinepropanol. Yield 30%; mp 134–136° C. Anal. ($C_{17}H_{23}N_5O \cdot C_4H_4O_4$) C, H, N.

Example 129

2-[(E)-3-Phenyl-2-propenyloxy]-3-(1-piperazinyl) pyrazine

The title compound was prepared starting from cinnamyl alcohol. Oil; yield 39%. Anal. ($C_{17}H_{20}N_4O \cdot 0.2H_2O$) C, H, N.

Example 130

2-(3,4-Dihydro-2H-1,4-benzoxazin-2-ylmethoxy)-3-(1-piperazinyl)pyrazine,

Dihydrochloride. Yield 22%; mp 171–175° C. Anal. ($C_{17}H_{21}N_5O_2 \cdot 2HCl$) C, H, N.
*The starting material 3,4-dihydro-2H-1,4-benzoxazin-2-ylmethanol was prepared as described in *J. Heterocycl. Chem.* 1996, 33, 191–196.

Example 131

2-(4-Methyl-3,4-dihydro-2H-1,4-benzoxazin-2-ylmethoxy)-3-(1-piperazinyl)-pyrazine, Hydrochloride.*

Yield 49%; mp 119° C. (dec). Anal. ($C_{18}H_{23}N_5O_2 \cdot 1.33HCl$) C, H, N.
*The starting material 3,4-dihydro-4 methyl-2H-1,4-benzoxazin-2-ylmethanol has previously been described in *J. Heterocycl. Chem.* 1996, 33, 191–196.

Example 132

2-(2,3-Dihydro-1,4-benzoxathiin-2-ylmethoxy)-3-(1-piperazinyl)pyrazine, Fumarate.*

Yield 41%; mp 178–79° C. Anal. ($C_{17}H_{20}N_4O_2S \cdot C_4H_4O_4$) C, H, N.
*The starting material 2,3-dihydro-1,4-benzoxathiin-2-yl)-methanol was prepared as described in *J. Pharm. Sci.* 1972, 61, 228–231.

Example 133

2-(3,4-Dihydro-2H-chromen-2-ylmethoxy)-3-(1-piperazinyl)pyrazine, Hydrochloride.*

Yield 45%; mp 170–175° C. Anal. ($C_{18}H_{23}N_4O_2 \cdot HCl$) C, H, N.
*The starting material 3,4-dihydro-2H-chromen-2-ylmethanol was prepared as described in *Eur. J. Med. Chem.* 1985, 20, 117–120.

Example 134

2-(5-Isoquinolinyloxy)ethyl 3-(1-piperazinyl)-2-pyrazinyl ether, Maleate

Step 1: 2-(5-Isoquinolinyloxy)ethanol.
A mixture of 5-hydroxyisoquinoline (2.05 g, 14.1 mmol), ethylene carbonate (1.43 g, 16.2 mmol), $K_2CO_3$ (0.97 g, 7.1 mmol) in DMF (6 mL) was heated at 155° C. for 1.5 h under stirring in a sealed tube. After cooling, the mixture was diluted with $CHCl_3$ and filtered through a pad of Celite. The brownish filtrate was concentrated in vacuo, and the residue was purified by chromatography on silica gel using EtOAc as eluent to give 1.8 g (67%) of the title product as a beige oil which solidified on standing: mp 64–67° C.; HRMS m/z calcd for $C_{11}H_{11}NO_2$ (M)$^+$189.0790, found 189.0789. Anal. ($C_{11}H_{11}NO_2$) C, H, N.

Step 2: 2-(5-Isoquinolinyloxy)ethyl 3-(1-piperazinyl)-2-pyrazinyl ether, Maleate.
Yield 55% as the free base. The free base was converted to the maleate salt: mp 178–180.5° C.; HRMS m/z calcd for $C_{19}H_{21}N_5O_2$(M)$^+$351.1695, found 351.1694. Anal. ($C_{19}H_{21}N_5O_2 \cdot C_4H_4O_4$) C, H, N.

Example 135

2-(5-Quinolinyloxy)ethyl 3-(1-piperazinyl)-2-pyrazinyl ether, Maleate

Step 1: 2-(5-Quinolinyloxy)ethanol
The title compound was prepared according to the procedure described in Example 134, Step 1, starting from 5-hydroxyquinoline (0.93 g, 6.40 mmol). Yield 1.19 g (91%); mp 109–111° C.; HRMS m/z calcd for $C_{11}H_{11}NO_2$ (M)$^-$189.0790, found 189.0786. Anal. ($C_{11}H_{11}NO_2$) C, H, N.

Step 2: 2-(5-Quinolinyloxy)ethyl 3-(1-piperazinyl)-2-pyrazinyl ether, Maleate.
Yield 61% as the free base. The free base was converted to the maleate salt: mp 132–135° C.; HRMS m/z calcd for $C_{19}H_{21}N_5O_2$(M)$^+$351.1695, found 351.1681. Anal. ($C_{19}H_{21}N_5O_2 \cdot 1.8C_4H_4O_4$) C, H, N.

Example 136

2-(6-Quinolinyloxy)ethyl 3-(1-piperazinyl)-2-pyrazinyl ether, Maleate

Step 1: 2-(6-Quinolinyloxy)ethanol.
The title compound was prepared according to the procedure described in Example 91, Step 1, starting from 6-hydroxyquinoline. Yield 78%; mp 68–70° C. Anal. ($C_{11}H_{11}NO_2$) C, H, N.

Step 2: 2-(6-Quinolinyloxy)ethyl 3-(1-piperazinyl)-2-pyrazinyl ether, Maleate.
Yield 33%; mp 167–169° C. Anal. ($C_{19}H_{21}N_5O_2 \cdot C_4H_4O_4$) C, H, N.

Example 137

2-(7-Quinolinyloxy)ethyl 3-(1-piperazinyl)-2-pyrazinyl ether, Maleate

Step 1: 2-(7-Quinolinyloxy)ethanol.
The title compound % vas prepared according to the procedure described in Example 91. Step 1, starting from 7-hydroxyquinoline. Yield 76%; mp 93–95° C. Anal. ($C_{11}H_{11}NO_2$) C, H, N.

Step 2: 2-(7-Quinolinyloxy)ethyl 3-(1-piperazinyl)-2-pyrazinyl ether, Maleate.
Yield 39%: mp 156–158° C. Anal. ($C_{19}H_{21}N_5O_2 \cdot C_4H_4O_4$) C, H, N.

Example 138

2-(8-Quinolinyloxy)ethyl 3-(1-piperazinyl)-2-pyrazinyl ether

Step 1: 2-(8-Quinolinyloxy)ethanol.*
The title compound was prepared according to the procedure described in Example 91, Step 1, starting from 8-hydroxyquinoline. Yield 48%; mp 82–84° C. Anal. ($C_{11}H_{11}NO_2$) C, H, N.

*Previously described in *Pharm. Chem. J.* 1994, 28, 934–936.

Step 2: 2-(8-Quinolinyloxy)ethyl 3-(1-piperazinyl)-2-pyrazinyl ether.

Yield 62%; mp 98–100° C. Anal. ($C_{19}H_{21}N_5O_2.0.05$ EtOAc) C, H, N.

Example 139

5-Chloro-8-(2-{[3-(1-piperazinyl)-2-pyrazinyl]oxy}ethoxy)-2-quinolinamine, Fumarate Step 1: 2-[(5-Chloro-8-quinolinyl)oxy]-1-ethanol.

The title compound was prepared according to the procedure described in Example 91, Step 1, starting from 5-chloro-8-hydroxyquinoline (3.59 g, 20 mmol). Yield 48%. Pos-EI-MS shows $M^+$ and 5 ions supporting the stated structure; HRMS m/z calcd for $C_{11}H_{10}ClNO_2(M)^+$ 223.0400, found 223.0392. Anal. ($C_{11}H_{10}ClNO_2$) C, H, N.

Step 2: 5-Chloro-8-(2-{[3-(1-piperazinyl)-2-pyrazinyl]oxy}ethoxy)-2-quinolinamine, Fumarate.

The crude product was purified by column chromatography on silica using $CHCl_3/MeOH/NH_4OH$ (90:10:0.3) as eluent. After evaporation of solvents from the combined pure fractions, the resulting free base was converted to its fumaric acid salt. Recrystallization from water afforded 1.22 g (50%) of the title product as white crystals: mp 178° C. (dec). Anal. ($C_{19}H_{20}N_5O_2.C_4H_4O_4$) C, H, N.

Example 140

2-(Benzofuran-7-yloxy)ethyl 3-(1-piperazinyl)-2-pyrazinyl)-2-ether, Maleate

Step) 1: 2-(Benzofuran-7-yloxy)ethanol.

The title compound was prepared according to the procedure described in Example 91, Step 1, starting from 7-hydroxybenzofuran* and was isolated as a semi-solid; yield 79%.

*Prepared as described in *J. Med. Chem.* 1987, 30, 62–67.

Step 2: 2-(Benzofuran-7-yloxy)ethyl 3-(1-piperazinyl)-2-pyrazinyl ether, Maleate.

Yield 42% as the free base. A portion of the free base was converted to the maleate salt: mp 177–179° C.; MS m/z 341 $(M+H)^+$. Anal. ($C_{18}H_{20}N_4O_3.C_4H_4O_4$) C, H, N.

Example 141

7-(2-{[3-(1-piperazinyl)-2-pyrazinyl]oxy}ethoxy)-1H-indole

Step 1: 2-(1H-Indol-7-yloxy)-1-ethanol.

A mixture of 7-hydroxyindole (1.00 g, 7.51 mmol) and ethylene oxide (0.33 g, 7.50 mmol) in dioxane (3 mL) was placed in a reaction tube. NaH (60% in oil; 0.100 g, 2.45 mmol) was added and the reaction mixture was stirred at 100° C. for 5 days. The reaction mixture was poured into water, extracted with EtOAc, dried ($MgSO_4$) and concentrated. The residue was purified by chromatography on silica gel using toluene/EtOAc (1:1) as eluent to give 0.45 g (34%) of the title product. Pos-EI-MS shows $M^+$ and 5 ions supporting the stated structure. HRMS m/z calcd for $C_{10}H_{11}NO_2$ $(M)^+$177.0790, found 177.0799.

Step 2: 7-(2-{[3-(1-piperazinyl)-2-pyrazinyl]oxy}ethoxy)-1H-indole

The product obtained in Step 1 above (0.200 g, 1.13 mmol) and dioxane (4 mL) was placed in a reaction tube and NaH (60% in oil; 0.060 g, 1.50 mmol) was added. When the gas evolution had ceased, 2-chloro-3-(1-piperazinyl)pyrazine (0.228 g, 1.15 mmol; from Example 90, Step 1) was added and the tube sealed. The mixture was stirred at 100° C. for 3 h. After cooling, the reaction mixture was poured into water and extracted with EtOAc. The organic layer was extracted with 0.5 M aqueous HCl. The pH of the aqueous phase was adjusted to pH 11 with NaOH and extracted with EtOAc. The organic layer was dried ($MgSO_4$) and concentrated to give 0.31 g (81%) of the title product. Pos-EI-MS shows $M^+$ and 9 ions supporting the stated structure. HRMS m/z calcd for $C_{18}H_{21}N_5O_2(M)^-$339.1695, found 339.1696.

Example 142

6-(2-{[3-(1-piperazinyl)-2-pyrazinyl]oxy}ethoxy)-1H-indole

Step 1: 2-(1H-Indol-6-yloxy)-1-ethanol.

A mixture of 6-hydroxyindole (2.66 g, 20 mmol) and $K_2CO_3$ (3.04 g, 22 mmol) was stirred in DMF (10 mL) at 80° C. for 10 min. A solution of ethylene carbonate (1.94 g, 22 mmol) in DMF (4 mL) was added and the mixture was heated at 125° C. for 3 h. The mixture was concentrated, diluted with water, and extracted with toluene. The organic phase was washed with 1 M aqueous $Na_2CO_3$ and brine. The organic layer was dried ($Na_2SO_4$) and concentrated. The residue was purified by flash chromatography on silica using EtOAc/toluene (1:4→36:65) as eluent. Yield 1.02 g (29%); mp 74–77° C.; HRMS m/z calcd for $C_{10}H_{11}NO_2(M)^+$ 177.0790, found 177.0784. Anal. ($C_{10}H_{11}NO_2$) C, H, N.

Step 2: 6-(2-{[3-(1-piperazinyl)-2-pyrazinyl]oxy}ethoxy)-1H-indole.

Yield 59%; mp 111–113° C.; MS-EI m/z 339 $(M)^+$. Anal. ($C_{18}H_{21}N_5O_2$) C, H, N.

Example 143

2-Methyl-5-(2-{[3-(1-piperazinyl)-2-pyrazinyl]oxy}ethoxy)-1,3-benzothiazole Hydrochloride Step 1: 2-[(2-Methyl-1,3-benzothiazol-5yl)oxy]ethanol.

The title compound was prepared according to the procedure described in Example 91, Step 1, starting from 2-methyl-1,3-benzothiazol-5-ol. Yield 61%; mp 67–68° C. HRMS m/z calcd for $C_{10}H_{11}NO_2S$ $(M)^+$209.0510, found 209.0502. Anal. ($C_{10}H_{11}NO_2S$)C, H, N.

Step) 2: 2-Methyl-5-(2-{[3-(1-piperazinyl)-2-pyrazinyl]oxy}ethoxy)-1,3-benzothiazole, Hydrochloride.

Yield 58%; mp 188–190° C. HRMS m/z calcd for $C_{18}H_{21}N_5O_2S$ $(M)^+$371.1416, found 371.1421. Anal. ($C_{18}H_{21}N_5O_2S.HCl.0.3H_2O$) C, H, N.

Example 144

2-[2-(2-Methoxy-5-methylphenoxy)ethoxy]-3-(1-piperazinyl)pyrazine, Maleate

Step 1: 2-(2-Methoxy-5-methylphenoxy)ethanol.

The title compound was prepared according to the procedure described in Example 91, Step 1, starting from 2-methoxy-5-methylphenol. Yield 56%; mp 42–43° C. Anal. ($C_{10}H_{14}O_3$) C, H.

Step 2: 2-[2-(2-Methoxy-5-methylphenoxy)ethoxy]-3-(1-piperazinyl)pyrazine, Maleate.

Yield 56%; mp 148–149° C. Anal. ($C_{18}H_{24}N_4O_3.C_4H_4O_4$) C, H, N.

Example 145

7-(2-{[3-(1-piperazinyl)-2-pyrazinyl]oxy}ethoxy)-1-naphthylamine, Maleate

Step 1: 2-[(8-Amino-2-naphthyl)oxy]ethanol, Hydrochloride.

The title compound was prepared according to the procedure described in Example 91, Step 1, starting from 8-amino-2-naphthol. Yield 40%; mp 185° C. (dec). Anal. ($C_{12}H_{13}NO_2.HCl$) C, H, N.

Step 2: 7-(2-{[3-(1-piperazinyl)-2-pyrazinyl]oxy}ethoxy)-1-naphthylamine, Maleate.

Yield 21%; mp 120° C. (dec). Anal. ($C_{20}H_{23}N_5O_2 \cdot 1.7C_4H_4O_4$) C, H, N.

Example 146

2-(7-Nitro-2,3-dihydro-1,4-benzodioxin-2-ylmethoxy)-3-(1-piperazinyl)pyrazine

Step 1: 7-Nitro-2-hydroxymethyl-2,3-dihydro-1,4-benzodioxine.

Trifluoroacetic anhydride (20 mL, 149 mmol) was added dropwise to solution of 2-hydroxymethyl-2,3-dihydro-1,4-benzodioxine (6.64 g, 40 mmol) and $NH_4NO_3$(84.8 g, 60 mmol) in $CH_2Cl_2$(300 mL). The reaction mixture was stirred at room temperature for 4 h and then concentrated under reduced pressure. The residue was purified by chromatography on silica gel using EtOAc/isohexane (1:3 to 2:3) as eluent to give a small fraction (0.3 g, 4%) of the pure title compound and 6.5 g of a mixture of the C6- and C7 regioisomeric nitro derivatives. The regioisomeric mixture was taken on to Example 147 Step 1, without separation.

Step 2: 2-(7-Nitro-2,3-dihydro-1,4-benzodioxin-2-ylmethoxy) 3-(1-piperazinyl)pyrazine.

The title compound was prepared starting from the pure product obtained in Step 1 above. Oil; yield 43%; mp 133–135° C. HRMS m/z calcd for $C_{17}H_{19}N_5O_5(M)^+$ 373.1386, found 373.1367.

Example 147

2-(7-Acetamido-2,3-dihydro-1,4-benzodioxin-2-ylmethoxy)-3-(1-piperazinyl)pyrazine Step 1: 7-Amino-2-hydroxymethyl-2,3-dihydro-1,4-benzodioxine.

A mixture of 6- and 7-nitro-2-hydroxymethyl-2,3-dihydro-1,4-benzodioxine (6.3 g, 30 mmol; from Example 146, Step 1), ammonium formate (2.8 g, 45 mmol), and 10% Pd/C (0.4 g) in MeOH (200 mL) was stirred at room temperature for 3 h. The reaction mixture was filtered through a pad of Celite. The pad was washed with several portions of MeOH and the filtrate was concentrated in vacuo. The mixture of 6- and 7-amino substituted-2,3-dihydro-1,4-benzodioxin derivatives was separated by chromatography on silica gel using EtOAc/isohexane (1:3 to 2:3) as eluent to give 2.8 g (58%) of the title product as an oil which was used directly in the next step.

Step 2: 7-Acetamido-2-hydroxymethyl-2,3-dihydro-1,4-benzodioxine.

Acetic anhydride (0.24 g, 2.4 mmol) was added to a stirred mixture of the title compound from Step 1 above (0.30 g, 1.66 mmol) and $Et_3N$ (0.70 g, 6.9 mmol) in $CH_2Cl_2$(30 mL). The reaction was stirred at room temperature for 15 h. More acetic anhydride (0.10 g, 1.0 mmol) was added and the mixture was stirred for a further 5 h at room temperature. The mixture was concentrated and the residue purified by chromatography on silica gel using EtOAc/isohexane (1:3 to 2:3) as eluent to give 170 mg (46%) of the title product as an oil.

Step 3: 2-(7-Acetamido-2,3-dihydro-1,4-benzodioxin-2-ylmethoxy),3-(1-piperazinyl)pyrazine.

Oil; yield 45%. HRMS m/z calcd for $C_{19}H_{23}N_5O_4(M)^+$ 385.1750, found 385.1741.

Example 148

2-[(2S)-2,3-Dihydro-1,4-benzodioxin-2-ylmethoxy]-3-(1-piperazinyl)pyrazine, Hydrochloride.*

Mp 160° C. (dec). Anal. ($C_{17}H_{20}N_4O_3 \cdot HCl$) C, H, N.
*The starting material (S)-2-hydroxymethyl-2,3-dihydro-1,4-benzodioxine was prepared as described in *Tetrahedron Lett.* 1988, 29, 3671–3674.

Example 149

2-[(2R)-2,3-Dihydro-,4-benzodioxin-2-ylmethoxy]-3-(1-piperazinyl)pyrazine, Hydrochloride.*

Mp 165° C. (dec). Anal. ($C_{17}H_{20}N_4O_3 \cdot HCl$) C, H, N.
*The starting material (R)-2-hydroxymethyl-2,3-dihydro-1,4-benzodioxine was prepared as described in *Tetrahedron Lett.* 1988, 29, 3671–3674.

Example 150

2-(3-Pyridyloxy)ethyl 3-(1-piperazinyl)-2-pyrazinyl ether, Hydrochloride

Step 1: 2-(3-Pyridyloxy)ethanol.*

A mixture of 3-hydroxypyridine (2.00 g, 21 mmol), 2-chloroethanol (1.69 g, 21 mmol) and $K_2CO_3$(8.7, 63 mmol) in DMF (10 mL) was stirred at 130° C. for 3 h. After cooling, the black mixture was filtered through a short bed of alumina using acetone as eluent to afford a brown oil which was partitioned between water (30 mL) and $CH_2Cl_2$ (40 mL). The aqueous phase was extracted with $CH_2Cl_2$(3× 40 mL), and the combined organic extracts were dried over $MgSO_4$ and filtered. The filtrate was concentrated to give, 0.55 g (19%) of the title compound as a light brown oil. Anal. ($C_7H_9NO_2 \cdot 0.2H_2O$)C, H, N.
*Previously described in EP 286242(A2).

Step 2: 2-(3-Pyridyloxy)ethyl 3-(1-piperazinyl)-2-pyrazinyl ether, Hydrochloride.

Yield 41%; mp 170–175° C. Anal. ($C_{15}H_{19}N_5O_2 \cdot 2HCl \cdot 2H_2O$)C, H, N.

Example 151

2-(4-Pyridyloxy)ethyl 3-(1-piperazinyl)-2-pyrazinyl ether, Hydrochloride

Step 1: 2-(4-Pyridyloxy)ethanol.*

The title compound was prepared according to the procedure described in Example 150, Step 1. Yield 19%; mp 119–121° C. Anal. ($C_7H_9NO_2$) C, H, N.
*Previously described in *J. Chem. Soc., Perkin Trans* 2, 1987, 1867–1870.

Step 2: 2-(4-Pyridyloxy)ethyl 3-(1-piperazinyl)-2-pyrazinyl ether, Hydrochloride.

Yield 58%; mp 170° C. (dec). Anal. ($C_{15}H_{19}N_5O_2 \cdot 2HCl \cdot 2H_2O$)C, H, N.

Example 152

2-(2-Pyridyloxy)ethyl 3-(1-piperazinyl)-2-pyrazinyl ether, Maleate

Step 1: 2-(2-Pyridyloxy)ethanol, Hydrochloride.*

A mixture of ethylene carbonate (2.78 g, 31.5 mmol), 2-hydroxypyridine (3.00 g, 31.5 mmol) and potassium carbonate (4.36 g, 31.5 mmol) in DMF (50 mL) was heated at 150° C. for 1 h. After cooling, the reaction mixture was concentrated in vacuo. The residue was dissolved in water (5 mL) and applied to a column with hydromatrix material. The column was eluted with EtOAc. The elute was concentrated and the remaining oil was purified by silica gel chromatography using isohexane/EtOAc (6:4) as eluent. This furnished the free base of the title compound as an oil which was converted to the hydrochloride salt: yield 1.00 g (18%); mp 97–98° C. Anal. ($C_7H_9NO_2 \cdot HCl$) C, H, N.
*The free base of the title compound has been reported in *J. Org. Chem.* 1977, 42, 1500–1508.

Step 2: 2-(2-Pyridyloxy)ethyl 3-(1-piperizinyl)-2-pyrazinyl ether, Maleate.

Yield 27%; mp 130–132° C. Anal. ($C_{15}H_{19}N_5O_2 \cdot C_4H_4O_4$) C, H, N.

Example 153

2-(6-Methyl-3-pyridyloxy)ethyl 3-(1-piperazinyl)-2-pyrazinyl ether, Hydrochloride

Step 1: 2-(6-Methyl-3-pyridyloxy)ethanol.

The title compound was prepared according to the procedure described in Example 91, Step 1, starting from 3-hydroxy-6-methylpyridine. Yield 25%, mp 49–51° C. Anal. ($C_8H_{11}NO_2$) C, H, N.

Step 2: 2-(6-Methyl-3-pyridyloxy)ethyl 3-(1-piperazinyl)-2-pyrazinyl ether, Hydrochloride.

Yield 50%; mp 157° C. (dec). Anal. ($C_{16}H_{21}N_5O_2.2.3HCl.0.2\ Et_2O$) C, H, N.

Example 154

2-(2-Methyl-3-pyridyloxy)ethyl 3-(1-piperazinyl)-2-pyrazinyl ether, Hydrochloride

Step 1: 2-(2-Methyl-3-pyridyloxy)ethanol.

The title compound was prepared according to the procedure described in Example 150, Step 1, starting from 3-hydroxy-2-methylpyridine. Yield 36%; mp 75–80° C. Anal. ($C_8H_{11}NO_2$) C, H, N.

Step 2: 2-(2-Methyl-3-pyridyloxy)ethyl 3-(1-piperazinyl)-2-pyrazinyl ether, Hydrochloride.

Yield 36%; mp 50° C. (dec). Anal. ($C_{16}H_{21}N_5O_2.3.1HCl.0.2\ Et_2O$) C, H, N.

Example 155

2-(5-Chloro-3-pyridyloxy)ethyl 3-(1-piperazinyl)-2-pyrazinyl ether, Hydrochloride

Step 1: 2-(5-Chloro-3-pyridyloxy)ethanol.

The title compound was prepared according to The procedure described in Example 150. Step 1, starting from 5-chloro-3-pyridinol. Yield 25%; mp 38–40° C. HRMS m/z calcd for $C_7H_8ClNO_2(M)^+$ 173.0244, found 173.0244.

Step 2: 2-(5-Chloro-3-pyridyloxy)ethyl 3-(1-piperazinyl)-2-pyrazinyl ether, Hydrochloride.

Yield 65%; mp 104° C. (dec). Anal. ($C_{15}H_{18}ClN_5O_2.1.9HCl.0.3Et_2O$) C, H, N.

Example 156

2-[2-(1-Benzothien-3-yloxy)ethoxy]-3-(1-piperazinyl)pyrazine, Maleate

Step 1: 2-(1-Benzothien-3-yloxy)ethanol.

A mixture of 3-bromobenzothiophene (3.00 g, 14.1 mmol), KO-t-Bu (4.74 g, 42.2 mmol), copper (II) oxide (0.56 g, 7.0 mmol) and potassium iodide (2.34 g, 14.1 mmol) in ethylene glycol (10 mL) was stirred at 140° C. for 24 h. The reaction was quenched with water (100 mL) and filtered through a pad of Celite. The water phase was extracted with EtOAc (3×50 mL). The organic phase was treated with $MgSO_4$ and silica, filtered through Celite and concentrated. The remaining oil was purified by column chromatography on silica using isohexane/EtOAc (6:4) as eluent. The product crystallized on standing to give 1.63 g (60%) of the title product: mp 55–56° C. Anal. ($C_{10}H_{10}O_2S$) C, H.

Step 2: 2-[2-(1-Benzothien-3-yloxy)ethoxy]-3-(1-piperazinyl)pyrazine, Maleate.

Solid; yield 0.23 g (32%): mp 147–149° C. Anal. ($C_{18}H_{20}N_4O_2S.C_4H_4O_4$) C, H, N.

Example 157

2-(3-Thienyloxy)ethyl 3-(1-piperazinyl)-2-pyrazinyl ether, Dihydrochloride.*

Yield 39%, mp 75–85° C. Anal. ($C_{14}H_{18}N_4O_2S.2.1HCl$) C, H, N.

*The starting material 2-(3-thienyloxy)ethanol was prepared as described in *Synth. Met.* 1988, 26, 153–168.

Example 158

2-(2,3-Dihydro-2,2-dimethyl-7-benzofuranyloxy)ethyl 3-(1-piperazinyl)-2-pyrazinyl ether, Maleate

A mixture of 2,3-dihydro-2,2-dimethyl-7-benzofuranol (0.82 g, 5.0 mmol), ethylene oxide (0.22 g, 5.0 mmol), triethylamine (3 drops) and dioxane (4 mL) was heated at 100° C. in a sealed tube for 3 d. The solution was cooled in an ice-bath and KO-t-Bu (0.56 g, 5 mmol) followed by 2-chloro-3-(1-piperazinyl)pyrazine (0.79 g, 4.0 mmol; from Example 90, Step 1) were added. The mixture was stirred at room temperature for 30 min and at 100° C. for 4 h, allowed to cool, diluted with $CH_2Cl_2$ and filtered. The filtrate was concentrated and purified by chromatography on silica gel (gradient: PhMe to PhMe/MeOH/$Et_3N$, 8:1:1) to give 1.46 g of a beige viscous oil. Maleic acid (0.46 g, 4.0 mmol) and dry MeOH (10 mL) was added. The mixture was heated until a clear solution formed. Upon cooling, the maleate salt of the title compound crystallized as a pale beige solid: yield 1.40 g (72%); mp 156–157° C. Anal. ($C_{20}H_{26}N_4O_3.C_4H_4O_4$) C, H, N.

Example 159

2-(1,3-Benzoxazol-4-yloxy)ethyl 3-(1-piperazinyl)-2-pyrazinyl ether, Maleate

Step 1: 2-(1,3-Benzoxazol-4-yloxy)ethanol.

$K_2CO_3$ (254 mg, 1.84 mmol) was added to a stirred solution of 4-hydroxybenzoxazole* (248 mg, 1.84 mmol) in DMF (5 mL) at room temperature. The mixture was heated at 90° C. for 15 min and ethylene carbonate (176 mg, 2.00 mmol) was added. The mixture was stirred at 150° C. for 2 h and allowed to attain room temperature. The mixture was diluted with water (2 mL) and MeOH (2 mL), and concentrated. The residue was partitioned between water and $CH_2Cl_2$. The aqueous layer was separated and extracted with $CH_2Cl_2$ (2×10 mL). The organic phases were pooled and washed with water and brine, and dried over $MgSO_4$. The filtrate was concentrated to give the product as a brown oil that slowly solidified: yield 278 mg (84%); mp 47–49° C. Anal. ($C_9H_9NO_3$) C, H, N.

*Prepared as described in *J. Med. Chem.* 1987, 30, 62–67.

Step 2: 2-(1,3-Benzoxazol-4-yloxy)ethyl 3-(1-piperazinyl)-2-pyrazinyl ether, Maleate. KO-t-Bu (146 mg, 1.30 mmol) was added in one portion to a stirred solution of 2-(1,3-benzoxazol-4-yloxy)ethanol (223 mg, 1.24 mmol) in dioxane (5 mL) at room temperature. After 15 min, 2-chloro-3-(1-piperazinyl)pyrazine (247 mg, 1.24 mmol; from Example 90, Step 1) was added in one portion followed by dioxane (3 mL). The mixture was stirred at room temperature for 10 min and at 100° C. for 3 h, allowed to cool, diluted with $CH_2Cl_2$ and filtered through Celite. The filtrate was concentrated and purified by chromatography on silica gel (gradient: PhMe to PhMe/MeOH/$Et_3N$, 8:1:1) to give the product (70 mg, 17%) as a beige viscous oil. The maleate salt was prepared as described in Example 158: mp 191–193° C. Anal. ($C_{17}H_{19}N_5O_3.C_4H_4O_4$) C, H, N.

Example 160

4-(2-{[3-(1-piperazinyl)-2-pyrazinyl]oxy}ethoxy)-2-quinolinamine, Trihydrochloride

Step 1: 2-[(2-Amino-4-quinolinyl)oxy]-1-ethanol.

To a mixture of 2-amino-4-hydroxyquinoline (0.505 g, 3.15 mmol) and $K_2CO_3$ (0.87 g, 6.3 mmol) in DMF (10 mL) was added of 2-bromoethanol (0.470 g, 3.78 mmol). The mixture was stirred at 150° C. for 7 h. The reaction mixture was concentrated and the residue purified by column chromatography on silica using MeOH/CHCl$_3$ (1:9) as eluent. The resulting brown oil (0.30 g, 30%), which was used directly in the next step, contained 75% of the desired product and 25% of unreacted starting material. MS m/z 205 (M+H)$^+$.

Step 2: 4-(2-{[3-(1-piperazinyl)-2-pyrazinyl]oxy}ethoxy)-2-quinolinamine, Trihydrochloride.

The product obtained in Step 1 (0.30 g, 1.5 mmol) was dissolved in DMF (4 mL) and treated with NaH (55% dispersion in mineral oil; 0.12 g, 3.0 mmol). After beeing stirred for 5 min at room temperature, 2-chloro-3-(1-piperazinyl)pyrazine (0.212 g, 1.07 mmol; from Example 90, Step 1) was added. The reaction mixture was stirred at 70° C. for 4 h and at room temp for 14 h. Purification by column chromatography on silica gel using 20% MeOH in CHCl$_3$ as eluent furnished 0.102 g (25%) of the free base of the title compound which was converted to a hydrochloric acid salt: mp 156° C. (dec). HRMS m/z calcd for C$_{19}$H$_{22}$N$_6$O$_2$(M)$^+$366.1804, found 366.1795.

Example 161

2-(3,4-Dihydro-2H-pyrido[3,2-b]1,4-oxazin-2-ylmethoxy)-3-(1-piperazinyl)pyrazine, Maleate Step 1: 3,4-Dihydro-3-oxo-2H-pyrido[3,2-b]-1,4-oxazin-2-carboxylic acid ethyl ester.

Diethyl chloromalonate (9.73 g, 50 mmol) was added to a stirred mixture of 3-hydroxy-2-aminopyridine (5.51 g, 50 mmol), triethylamine (6.97 mL, 50 mmol) and EtOH (100 mL) at room temperature. The mixture was heated at reflux for 17 h and allowed to attain room temperature. The precipitate formed was filtered off, washed with EtOH and dried to give the product as a white solid: yield 3.85 g (35%); mp 160–162° C. Anal. (C$_{10}$H$_{10}$N$_2$O$_4$) C, H, N.

Step 2: 3,4-Dihydro-2H-pyrido[3,2-b]-1,4-oxazin-2-ylmethanol.

A solution of 3,4-dihydro-3-oxo-2H-pyrido[3,2-b]-1,4-oxazin-2-carboxylic acid ethyl ester (1.10 g, 5.0 mmol) in THF (50 mL) was added over 5 min to a stirred mixture of LiAlH$_4$ (0.38 g, 10 mmol) and THF (20 mL) at 40° C. The mixture was stirred at 45° C. for 30 min and at reflux for 4 h. The mixture was allowed to attain room temperature and excess LiAlH$_4$ decomposed with 50% aqueous NaOH. The mixture was filtered through Celite, and the filtrate was concentrated. The residue (0.42 g) was extracted with CH$_2$Cl$_2$ and the extract was concentrated and purified by chromatography on silica gel (gradient: PhMe to PhMe/MeOH/Et$_3$N, 8:1:1) to give the product as a white solid: yield 0.11 g (13%); mp 123–124° C. Anal. (C$_8$H$_{10}$N$_2$O$_2$) C, H, N.

Step 3: 2-(3,4-Dihydro-2H-pyrido[3,2-b]-1,4-oxazin-2-ylmethoxy)-3-(1-piperazinyl)pyrazine, Maleate.

The title compound was prepared in an analogous manner to Example 159, Step 2, starting from 3,4-dihydro-2H-pyrido[3,2-b]-1,4-oxazin-2-ylmethanol and was isolated as a brownish solid. Yield 47%: nip 154–158° C. Anal. (C$_{16}$H$_{20}$N$_6$O$_2$.1.2C$_4$H$_4$O$_4$) C, H, N.

Example 162

2-[2-(3-Pyridinyloxy)ethoxy]-3-(1-piperazinyl) quinoxaline, Maleate

Step 1: 2-Chloro-3-(1-piperazinyl)quinoxaline, Maleate.*

A mixture of 2,3-dichloroquinoxaline (3.05 g, 15.3 mmol), piperazine (2.64 g, 30.6 mmol) and K$_2$CO$_3$ (2.12 g, 15.3 mmol) in acetonitrile (20 mL) was stirred at 55° C. for 1 h. The reaction mixture was diluted with CHCl$_3$, filtered, and concentrated to give a yellowish solid which was purified by chromatography on silica gel using CHCl$_3$/MeOH (9:1) as eluent. The resulting solid was redissolved in CHCl$_3$ and applied to a short (4 cm) plug of alumina. Elution with CHCl$_3$ afforded 3.08 g (81%) of the free base of the title compound, which was isolated as a light yellow solid. A portion of the free base was converted to the maleate and recrystallized from MeOH/ether: mp 165–166° C.; HRMS m/z calcd for C$_{12}$H$_{13}$ClN$_4$ (M)$^+$248.0829, found 248.0830. Anal. (C$_{12}$H$_{13}$ClN$_4$.C$_4$H$_4$O$_4$) C, H, N.

*The corresponding hydrochloride salt has been reported in *J. Med. Chem.* 1981, 24, 93–101.

Step 2: 2-[2-(3-Pyridinyloxy)ethoxy]-3-(1-piperazinyl) quinoxaline, Maleate.

KO-t-Bu (0.57 g, 5.1 mmol) was added to a stirred solution of 2-(3-pyridyloxy)ethanol (0.97 g, 7.0 mmol; from Example 150, Step 1) in dioxane (20 mL) and the mixture was stirred for 3 min at room temperature. The free base from Step 1 above (0.97 g, 3.89 mmol) was then added and the resulting mixture was stirred at 80° C. for 4 h. The reaction mixture was diluted with CH$_2$Cl$_2$, filtered, and concentrated to give a yellowish oil which was purified by chromatography on silica gel using CHCl$_3$/MeOH (9:1) as eluent. The resulting oil was redissolved in CHCl$_3$ and applied to a short (4 cm) plug of alumina. Elution with CHCl$_3$ afforded 1.20 g (88%) of the free base of the title compound as a light beige oil. The free base was converted to the maleate salt and recrystallized from MeOH/ether: mp 137–139° C.; HRMS m/z calcd for C$_{19}$H$_{21}$N$_5$O$_2$ (M)$^+$ 351.1695, found 351.1701. Anal. (C$_{19}$H$_{21}$N$_5$O$_2$.1.3C$_4$H$_4$O$_4$) C, H, N.

Example 163

2-[2-(3-Pyridinyloxy)ethoxy]-3-(1-piperazinyl)-6,7-difluoroquinoxaline, Maleate

Step 1: 2-Chloro-3-(1-piperazinyl)-6,7-difluoroquinoxaline.

Piperazine (0.86 g, 10 mmol) was added to a stirred suspension of 6,7-difluoro-2,3-dichloroquinoxaline*(1.18 g, 5 mmol) in EtOH (50 mL) at room temperature. The mixture was heated at 75° C. for 17 h, allowed to cool and filtered to give the product as a pale yellow solid: yield 0.40 g (28%); mp 294–297° C. (dec). MS m/z 285/287 (M+H)$^+$.

*Previously described in *J. Med. Chem.* 1990, 33, 2240–2254.

Step 2: 2-[2-(3-Pyridinyloxy)ethoxy]-3-(1-piperazinyl)-6,7-difluoroquinoxaline, Maleate.

The title compound was prepared) according to the procedure described in Example 162, Step 2, starting from 2-chloro-3-(1-piperazinyl)-6,7difluoroquinoxaline (230 mg, 0.8 mmol) and 2-(3-pyridinyloxy)ethanol (140 mg, 1 mmol; from Example 150, Step 1). Yield 95 mg (31%). The maleate salt was obtained as described in Example 158: mp 110–5° C. Anal. (C$_{19}$H$_{19}$F$_2$N$_5$O$_2$.1.5C$_4$H$_4$O$_4$) C, H, N.

Example 164

2-[2-(3-Pyridinyloxy)ethoxy]-3-(1-piperazinyl)-6,7-dichloroquinoxaline, Maleate

Step 1: 3-(1-piperazinyl)-2,6,7-trichloroquinoxaline.

Piperazine (0.69 g, 8.06 mmol) was added to a stirred suspension of 2,3,6,7-tetrachloroquinoxaline (1.08 g, 4.03 mmol) in EtOH (125 mL) at room temperature. The mixture was stirred at room temperature for 8 h and filtered to give the product as a pale yellow solid: yield 0.88 g (69%), mp>300° C. MS m/z 316/318 (M)$^+$.

Step 2: 2-[2-(3-Pyridinyloxy)ethoxy]-3-(1-piperazinyl)-6,7-dichloroquinoxaline, Maleate.

The title compound was prepared according to the procedure described in Example 162, Step 2, starting from 3-(1-piperazinyl)-2,6,7-trichloroquinoxaline (270 mg, 1.00 mmol) and 2-(3-pyridinyloxy)ethanol (170 mg, 1.20 mmol; from Example 150, Step 1). Yield 135 mg (32%). The maleate salt was obtained as described in Example 158: mp 187–189° C. Anal. ($C_{19}H_{19}Cl_2N_5O_2 \cdot C_4H_4O_4$) C, H, N.

Example 165

2-[2-(3-Pyridinyloxy)ethoxy]3-(1-piperazinyl)thieno [3,4-b]pyrazine, Maleate

Step 1: 2,3-Dichlorothieno[3,4-b]pyrazine.

1,4-Dihydro-thieno[3,4-pyrazine-2,3dione* (1.26 g, 7.5 mmol) and $POCl_3$ (6.9 mL, 75 mmol) was stirred at reflux for 21 h. The dark mixture was poured onto ice and extracted with $CH_2Cl_2$ (4×30 mL). The organic extracts were pooled and concentrated to give 0.11 g (7%) of the title product which was used in the next step without purification.
*Previously described in Bull. Soc. Chim. Fr. 1983, 159–163.

Step 2: 2-Chloro-3-(1-piperazinyl)-thieno[3,4-b]pyrazine.

Piperazine (92 mg, 1.07 mmol) was added to a stirred suspension of 2,3-dichlorothieno[3,4-b]pyrazine (110 mg, 0.54 mmol) in EtOH (5 mL) at room temperature. The mixture was stirred at reflux for 16 h and filtered. The solid was purified by chromatography on silica gel (gradient: PhMe to PhMe/MeOH/Et₃N, 8:1:1) to give 40 mg (29%) of the product as an orange solid. The material was used without further purification in the next step.

Step 3: 2-[2-(3-Pyridinyloxy)ethoxy]-3-(1-piperazinyl) thieno [3,4-b]pyrazine, Maleate.

The title compound was prepared according to the procedure described in Example 162, Step 2, starting from 2-chloro-3-(1-piperazinyl)-thieno[3,4-b]pyrazine (40 mg, 0.16 mmol; from Step 2 above) and 2-(3-pyridinyloxy) ethanol (44 mg, 0.31 mmol; from Example 150, Step 1. Yield 38 mg (66%). The maleate was obtained as described in Example 158: mp 152–156° C. Anal. ($C_{17}H_{19}N_5O_2S \cdot 1.8C_4H_4O_4$) C, H, N.

Example 166

2-[2-(5-Pyrimidinyloxy)ethoxy]-3-(1-piperazinyl) quinoxaline

Step 1: 2-(5-Pyrimidinyloxy)ethanol.

KO-t-Bu (7.70 g, 68.6 mmol) was added to ethylene glycol (10.45 g, 168.4 mmol) under stirring. The mixture was gently heated in order to consume all KO-t-Bu. 5-Bromopyrimidine (8.45 g, 53.1 mmol) was added to the light brownish mixture. After 8 h of stirring at 130° C., $CH_2Cl_2$ (50 mL) was added to the brownish reaction mixture and two layers were formed. The $CH_2Cl_2$ layer was saved and the other layer was extracted with additional portions of $CH_2Cl_2$. The combined $CH_2Cl_2$ layers were concentrated in vacuo and the oily residue purified by column chromatography on silica gel using $CHCl_3/MeOH$ (9:1) as eluent to give 0.45 g (6%) of the title product as an oil sufficiently pure for the next step. HRMS m/z calcd for $C_6H_8N_2O_2(M)^+$ 140.0586, found 140.0589.

Step 2: 2-[2-(5-Pyrimidinyloxy)ethoxy]-3-(1-piperazinyl) quinoxaline.

The title compound was prepared according to the procedure described in Example 162, Step 2, starting from 2-chloro-3-(1-piperazinyl)quinoxaline (0.66 g, 2.65 mmol; from is Example 162, Step 1) and 2-(5-pyrimidinyloxy) ethanol (0.45 g, 3.20 mmol). Yield 0.55 g (59%); mp 115–117° C.; HRMS m/z calcd for $C_{18}H_{20}N_6O_2$ (M)⁺ 352.1648, found 352.1654. Anal. ($C_{18}H_{20}N_6O_2$) C, H, N.

Example 167

2-(3,4-Dihydro-2H-1,4-benzoxazin-2-ylmethoxy)-3-(1-piperazinyl)quinoxaline, 0.5 Fumarate The title product was prepared according to the procedure described in Example 162, Step 2, starting from 2-chloro-3-(1-piperazinyl)quinoxaline (described in Example 162. Step 1) and 3,4-dihydro-2H-1,4-benzoxazin-2-ylmethanol.* Yield 41%; mp 125–134° C. (dec). Anal. ($C_{21}H_{23}N_4O_4 \cdot 0.5C_4H_4O_4 \cdot 2H_2O$)C, H, N.
*See Example 130.

Example 168

2-(3,4-Dihydro-2H-chromen-2-ylmethoxy)-3-(1-piperazinyl)quinoxaline

The title product was prepared according to the procedure described in Example 162, Step 2, starting from 2-chloro-3-(1-piperazinyl)quinoxaline (described in Example 162. Step 1) and 3,4-dihydro-2H-chromen-2-ylmethanol.* The product was obtained as a yellow amorphous substance: yield 23%; mp 202–204° C.; HRMS m/z calcd for $C_{13}H_{16}N_4O_2(M)^+$376.1899, found 376.1899. Anal. ($C_{22}H_{24}N_4O_2 \cdot HCl$) H; C: calcd, 61.32; found. 60.7; N: calcd, 13.00; found 13.5.
*See Example 133.

Example 169

2,3-Dihydro-1,4-benzodioxin-2-ylmethyl 3-(4-methyl-1-piperazinyl)-2-pyrazinyl ether, Dihydrochloride Step 2: 1-(3-Chloro-2-pyrazinyl)-4-methylpiperazin A mixture of 2,3-dichloropyrazine (10.1 g, 68 mmol) and N-methylpiperazine (10.15 g, 100 mmol) in acetonitrile (250 mL) was stirred at room temperature for 60 h. The solvent was removed under reduced pressure and the residue was taken up in $CHCl_3$/brine. The dried ($MgSO_4$) organic layer was concentrated and the remaining oil was purified by chromatography on silica gel using $CHCl_3/MeOH$ (95:5) as eluent to give 10.7 g (75%) of the title compound as an oil that crystallized upon standing: mp 34–36° C. Anal. ($C_9H_{13}ClN_4$) C, H, N.

Step 2: 2,3-Dihydro-1,4-benzodioxin-2-ylmethyl 3-(4-methyl-1 piperazinyl)-2-pyrazinyl ether, Dihydrochloride.

The title compound was prepared according to the procedure described in Example 90, Step 2, starting from 1-(3-chloro-2-pyrazinyl)-4-methylpiperazine (described in Example 169, Step 1) and 2-hydroxymethyl-2,3-dihydro-1, 4-benzodioxine. Yield 87%; mp 160–167° C. Anal. ($C_{18}H_{22}N_4O_3 \cdot 2$ HCl) H, N; C: calcd, 52.06; found, 52.6.

Example 170

2-(Phenoxy)ethyl-3-(4-methyl-1-piperazinyl)-2-pyrazinyl ether, Hydrochloride

The title compound was prepared according to the procedure described in Example 90, Step 2, starting from 1-(3-chloro-2-pyrazinyl)-4-methylpiperazine (described in Example 169, Step 1) and 2-phenoxyethanol. Yield 79%; mp 172–174° C. Anal. ($C_{17}H_{22}N_4O_2 \cdot HCl$) C, H, N.

Example 171

2-(2-Phenoxy)ethyl 3-(2-methyl-1-piperazinyl)-2-pyrazinyl ether, Maleate

Step 1: 3-Chloro-2-(4-benzyl-2-methyl-1-piperazinyl) pyrazine.

A mixture of 2,3-dichloropyrazine (0.332 g, 2.23 mmol), 1-benzyl-3-methylpiperazine* (0.423 g, 2.23 mmol), and $K_2CO_3$ (0.339 g, 2.45 mmol) in acetonitrile (2.5 mL) was stirred at 115° C. for 17 h in a sealed tube. The reaction mixture was diluted with ether, filtered, and concentrated.

The brownish oily residue was purified by chromatography on silica gel using n-hexane/EtOAc (7:3) as eluent to give 0.19 g (28%) of the title product as a viscous oil that was sufficiently pure for the next step.
*Previously described in *J. Med. Chem.* 1996, 39, 2962–2970.

Step 2: 2-(2-Phenoxy)ethyl 3-(4-benzyl-2-methyl-1-piperazinyl)-2-pyrazinyl ether.

KO-t-Bu (0.087 g, 0.77 mmol) was added in one portion to a stirred solution of 2-phenoxyethanol (0.164 g, 1.19 mmol) in dioxane (5 mL) at room temperature. After being stirred for 5 min at 90° C., a solution of the product obtained in Step 1 above (0.18 g, 0.59 mmol) in dioxane (3 mL) was added. The mixture was stirred at room temperature for 10 min and at 85° C. for 2 h. The reaction mixture was diluted with ether, filtered, and concentrated. The remaining beige oil was purified by chromatography on silica gel using n-hexane/EtOAc (7:3) as eluent to give 0.22 g (93%) of the title product as an oil. HRMS m/z calcd for $C_{24}H_{28}N_4O_2$ $(M)^+$ 404.2212, found 404.2232.

Step 3: 2-(2-Phenoxy)ethyl 3-(2-methyl-1-piperazinyl)-2-pyrazinyl ether, Maleate.

Ammonium formate (0.18 g, 2.85 mmol) was added to a solution of the product from Step 2 above (0.22 g, 0.54 mmol) in ethanol (5 mL). The mixture was purged with nitrogen and 5% Pd/C (0.15 g) was added. The flask was sealed and the mixture was stirred at 90° C. for 2.5 h. The reaction mixture % vas filtered through Celite and concentrated. The residue %% as purified by chromatography on silica gel using $CHCl_3$/MeOH (10:1) to give 0.12 g (72%) of the free base of the title compound as an oil. The free base was convened to the maleate and recrystallized from MeOH/ether: mp 102–103° C.; HRMS m/z calcd for $C_{17}H_{22}N_4O_2$ $(M)^+$ 314.1743, found 314.1754. Anal. $(C_{17}H_{22}N_4O_2 \cdot C_4H_4O_4)$ C, H, N.

Example 172

(2R)-Methyl-1-[3-(2-phenoxyethoxy)-2-pyrazinyl]piperazine, Hydrochloride

Step 1: 4-tert-Butoxycarbonyl-(2R)-methylpiperazine.

Glacial acetic acid (6.3 g, 105 mmol), followed by di-tert-butyldicarbonate (23.11 g, 106 mmol), were added to a stirred solution of (2R)-methylpiperazine (10.3 g, 103 mmol) in MeOH (200 mL) at 0° C., and the resulting mixture was stirred for 1 h. The reaction mixture was allowed to warm to room temperature and stirred for further 15 h. An excess of triethylamine (20 mL, 140 mmol) was added and the reaction mixture was concentrated under reduced pressure. The residue was suspended in $CHCl_3$ and filtered through a fritted glass filter. The filtrate was concentrated, and the residue was purified by chromatography on silica gel using $CHCl_3$/MeOH (85:15) as eluent to give 21 g (65%) of the title product as an oil that crystallized upon standing. The product was used in the next step without further characterization.

Step 2: 3-Chloro-2-[4-tert-butoxycarbonyl-(2R)-methyl-1-piperazinyl]pyrazine.

A mixture of 2,3-dichloropyrazine (22.0 g, 148 mmol), 4-tert-butoxycarbonyl-(2R)-methylpiperazine (21 g, 105 mmol) and $K_2CO_3$ (30.4 g, 220 mmol) in DMF was heated at 95° C. for 15 h. The black reaction mixture was filtered through a bed of silica gel, and the filtrate was concentrated. The residue was purified by chromatography on silica gel using petroleum ether/EtOAc (9:1) as eluent to afford 3.2 g (10% over two steps) of the title compound as a colourless oil. HRMS m/z calcd for $C_{14}H_{21}ClN_4O_2$ $(M)^+$ 312.1353, found 312.1358.

Step 3: (2R)-Methyl-1-[3-(2-phenoxyethoxy)-2-pyrazinyl]piperazine, Hydrochloride.

KO-t-Bu (0.52 g, 4.66 mmol) was added to a solution of 2-phenoxyethanol (0.42 g, 3.0 mmol) in dioxane (15 mL) and the mixture was stirred at room temperature for 15 minutes. 4-tert-Butoxycarbonyl-(2R)-methylpiperazine (0.73 g, 2.33 mmol: from Step 1 above) was added to the suspension and the reaction was stirred at 85° C. for 15 h. The reaction mixture was filtered through Celite and the filtrate was concentrated under reduced pressure. The crude product was purified by chromatography on silica gel using $CHCl_3$/MeOH/$NH_4OH$ (97:3:0.2) as eluent. The resulting oil was dissolved in $CH_2Cl_2$1TFA (1:1) and the mixture was stirred at room temperature for 15 h. The mixture was concentrated under reduced pressure and the remaining oil was partitioned between 1 M NaOH/$CHCl_3$. The organic phase was dried ($MgSO_4$) and the solvent evaporated. The resulting oil was purified by chromatography on silica gel using $CHCl_3$/MeOH/$NH_4OH$ (95:5:0.2) as eluent to provide the free base of the title compound. The free base was precipitated as its hydrochloride salt with HCl/ether to give 0.36 g (44%) of the title compound as white crystals: mp 164–166° C.; HRMS m/z calcd for $C_{17}H_{22}N_4O_2$ $(M)^+$ 314.1731, found 314.1743. Anal. $(C_{17}H_{22}N_4O_2 \cdot HCl)$ C, H, N.

Examples 173–177 were prepared according to the procedure of Example 172, step 3.

Example 173

(2R)-Methyl-1-{3-[2-(3-pyridinyloxy)ethoxy]-2-pyrazinyl}piperazine, Hydrochloride The title compound was prepared starting from 2-(3-pyridyloxy)ethanol (from Example 150, Step 1) and 3-chloro-2-[4-tert-butoxycarbonyl-(2R)-methyl-1-piperazinyl]pyrazine (from Example 172, Step 2). The pure free base was precipitated as its hydrochloride salt with HCl/ether to give the title compound as white crystals: yield 31%; mp 180–183° C.; HRMS m/z calcd for $C_{16}H_{21}N_5O_2$ $(M)^+$ 315.1695, found 315.1689. Anal. $(C_{16}H_{21}N_5O_2 \cdot 1.33HCl)$ C, H, N.

Example 174

(2S)-Methyl-1-{3-[2-(3-pyridinyloxy)ethyloxy]-2-pyrazinyl}piperazine, Hydrochloride The title compound was prepared starting from 2-(3-pyridyloxy)ethanol (from Example 150, Step 1) and 3-chloro-2-[4-tert-butoxycarbonyl-(2S)-methyl-1-piperazinyl]pyrazine (prepared according to the procedure of Example 172, Step 2, with the exception that (2S)-methyl piperazine was substituted for (2R)-methylpiperazine). MS m/z 316 (M+H)$^+$. Yield 58%; mp 170–172° C. Anal. $(C_{16}H_{21}N_5O_2 \cdot 1.45HCl)$ C, H, N.

Example 175

(2S)-Methyl-1-[3-(2-phenoxyethoxy)-2-pyrazinyl]piperazine, Hydrochloride

The title compound was prepared starting from 2-phenoxy-1-ethanol and 3-chloro-2-[4-tert-butoxycarbonyl-(2S)-methyl-1-piperazinyl]pyrazine (prepared according to the procedure of Example 172, Step 2, with the exception that (2S)-methylpiperazine was substituted for (2R)-methylpiperazine). MS m/z 315 (M+H)$^+$. Yield 68%; mp 162–163° C. Anal. $(C_{17}H_{22}N_4O_2 \cdot HCl)$ C, H, N.

Example 176

(2R)-2-Methyl-1-(3-{2-[(6-methyl-3-pyridinyl)oxy]ethoxy}-2-pyrazinyl)piperazine, Fumarate The title product was prepared from 2-(6-methyl-3-pyridyloxy)ethanol (from Example 153, Step 1) and 3-chloro-2-[4-tert-butoxycarbonyl-(2R)-methyl-1-piperazinyl]pyrazine (from Example 172, Step 2). The crude product was purified by column chromatography on silica using $CHCl_3/MeOH/NH_4OH$ (95:5:0.2) as eluent. After evaporation of the solvent from the combined pure fractions, the resulting free base was precipitated as its fumaric acid salt. Recrystallization from MeOH/ether gave 46% of the title product as an amorphous solid: mp 115° C. (dec). Anal. $(C_{17}H_{23}N_5O_2 \cdot C_4H_4O_4)$ C, H, N.

Example 177

(2R)-Methyl-1-{3-]2-(2-amino-8-quinolinyloxy)ethoxy]-2-pyrazinyl}piperazine, Fumarate Step 1: 2-(2-Amino-8-quinolinyloxy)-ethanol.

A mixture of 2-amino-8-quinolinol (3.20 g, 20.0 mmol), ethylene carbonate (1.76 g, 20.0 mmol) and KO-t-Bu (2.24 g, 20.0 mmol) in DMF (20 mL) was stirred at 90° C. for 15 h. The mixture was poured into brine, extracted with EtOAc, dried ($MgSO_4$), and concentrated under reduced pressure. The residue was purified by chromatography on silica gel using toluene/EtOAc/MeOH (50:50:2) as eluent to give 1.13 g (28%) of the title product as a solid HRMS m/z calcd for $C_{11}H_{12}N_2O_2 (M)^+ 204.0899$, found 204.0906.

Step 2: (2R)-Methyl-1-{3-[2-(2-amino-8-quinolinyloxy)ethoxy]-2-pyrazinyl}piperazine, Fumarate.

The title compound was prepared starting from 2-(2-amino-8-quinolinyloxy)ethanol and 3-chloro-2-[4-tert-butoxycarbonyl-(2R)-methyl-1-piperazinyl]pyrazine (from Example 172, Step 2). The pure free base was precipitated as its fumaric acid salt to give the title compound as yellow, slightly hygroscopic, crystals: yield 5%; mp 160–163° C. (dec). HRMS m/z calcd for $C_{20}H_{24}N_6O_2 (M)^+ 380.1961$, found 380.1958.

Example 178

2-Ethyl-1-{3-[2-(3-pyridinyloxy)ethoxy]-2-pyrazinyl}piperazine, Fumarate

Step 1:1-Benzyl-3-ethylpiperazine.

Benzyl bromide (38.7 g, 0.22 mol) was added in portions to an ice cold (~0° C.) solution of 2-ethylpiperazine (25 g, 0.22 mol) in DMF (150 mL) with such a rate that the temperature did not exceed 20° C. The mixture was stirred for 1 h, the solvent was evaporated and the residue was partitioned between $CHCl_3/0.5$ M HCl. The aqueous phase was made alkaline (11M NaOH) and extracted three times with $CHCl_3$. The combined organic phases were dried ($MgSO_4$) and concentrated. The resulting oil was purified by column chromatography on silica using $CHCl_3$, followed by $CHCl_3/MeOH/NH_4OH$ (95:5:0.3) as eluents to give 31.6 g (70%) of the title compound as a yellowish oil. Anal. $(C_{13}H_{20}N_2)$ H, N; C: calc, 76.42 found 75.85; H, N.

Step 2: 4-Benz-1-(3-chloro-2-pyrazinyl)-2-ethylpiperazine.

A mixture of 2,3-dichloropyrazine (3.9 g, 27 mmol), 1-benzyl-3-ethylpiperazine (4.6 g, 22.5 mmol; from Step 1) and $K_2CO_3$ (6.2 g, 45 mmol) in DMF (10 mL) was stirred at 100° C. for 4 days. The solvent from the filtered reaction mixture was evaporated off and the residue was purified by column chromatography on silica using heptane/EtOAc (90:10) as eluent to yield 5.0 g (71%) of the title compound as a light yellow oil. HRMS m/z calcd for $C_{17}H_{21}ClN_4 (M)^+ 316.1455$, found 316.1448.

Step 3:1-(3-Chloro-2-pyrazinyl)-2-ethylpiperazine, Hydrochloride.

1-Chloroethyl chloroformate (2.11 g, 15.2 mmol) was added with a syringe during 1 h to an ice cold (~0° C.) solution of 4-benzyl-1-(3-chloro-2-pyrazinyl)-2-ethylpiperazine (3.22 g, 10.1 mmol, from Step 2) in dry $CH_2Cl_2$ (30 mL). The reaction-was-allowed to slowly reach room temperature and stirred for 48 h. The solvent was evaporated from the reaction mixture and MeOH was added to the resulting oil. The mixture was heated to reflux for 2 h, the solvent was evaporated and the resulting oil was partitioned between $CHCl_3/H_2O$. The aqueous phase was made alkaline and extracted with $CHCl_3$ (×3). The combined organic phases were dried ($MgSO_4$), and the solvent was evaporated. The resulting oil was purified by column chromatography on silica using $CHCl_3/MeOH/NH_4OH$ (95:5:0.2) as eluent to give a quantitative yield (2.35 g) of the free base of the title compound as a slightly yellow oil. An analytical sample was prepared as its hydrochloric acid salt (from HCl/ether): mp 195–197° C. Anal. $(C_{10}H_{15}ClN_4 \cdot HCl)$ C, H, N.

Step 4. 2-Ethyl-1-{3-[2-(3-pyridinyloxy)ethoxy]-2-pyrazinyl}piperazine, Fumarate.

The title compound was prepared starting from 2-(3-pyridyloxy)ethanol (from Example 150, Step 1) and the product obtained in Step 3 according to the procedure described in Example 162, Step 2. The crude product was purified by column chromatography on silica using $CHCl_3/MeOH/NH_4OH$ (90:10:0.3) as eluent. After evaporation of the solvent from the combined pure combined fractions, the resulting free base was converted to its fumarate salt and crystallized from MeOH to afford 0.21 g (8%) of the title compound as light yellow crystals: mp 125–127° C.; HRMS m/z calcd for $C_{17}H_{23}N_5O_2 (M)^+ 329.1852$, found 329.1845. Anal. $(C_{17}H_{23}N_5O_2 \cdot C_4H_4O_4)$ C, H, N.

Example 179 cis-2,6-Dimethyl-1-{3-[2-(3-pyridinyloxy)ethoxy]-2-pyrazinyl}piperazine, Fumarate Step: 1-Benzyl-cis-3,5-dimethylpiperazine.*

To an ice cold (~0° C.) suspension of cis-2,6-dimethylpiperazine (4.0 g, 35 mmol) in DMF (100 mL) was benzyl bromide (6.0 g, 35.0 mmol) added in portions under a period of 45 min and the reaction mixture was stirred at room temperature for 48 h. The solvent was evaporated from the suspension and the residue was dissolved in aqueous HCl and washed twice with $CHCl_3$. The aqueous phase was made alkaline and extracted twice with $CHCl_3$. The combined organic phases were washed with $H_2O$ and brine, dried ($MgSO_4$), and concentrated to give 4.9 g (68%) of the title product as a colorless oil.

*Previously described in *J. Med. Chem.* 1964, 7, 241–242 and *Org. Prep. Proc. Int.* 1976, 8, 19–23.

Step 2: 4-Benzyl-1-(3-chloro-2-pyrazinyl)-cis-2,6-dimethylpiperazine.

A mixture of 2,3-dichloropyrazine (4.9 g, 32.9 mmol), 1-benzyl-cis-3,5-dimethylpiperazine (5.9 g, 29.0 mmol), tributylamine (5.9 g, 32 mmol) and diphenyl ether (70 mL) was heated in a sealed tube at 220° C. for 3 days. The reaction mixture was cooled to ambient temperature and EtOAc (200 mL) and toluene (100 mL) were added. The organic phase was extracted with 5 M aqueous HCl (×3) and the combined aqueous phases were extracted with $CHCl_3$ (×3). The combined organic layers, which contained the product, were washed with aqueous NaOH (5 M), dried (MgSO$_4$), and the solvent was evaporated. The crude product (0.96 g), about 80% pure based on GC, was used in the next step without further purification.

Step 3. 1-(3-Chloro-2-pyrazinyl)cis-2,6-dimethylpiperazine, Hydrochloride.

The title compound was prepared by treating the product obtained in Step 2 with 1-chloroethyl chloroformate according to the procedure described in Example 178, Step 3. The crude product % vas purified by column chromatography on silica using CHCl$_3$/MeOH/NH$_4$OH (95:5:0.2, followed by 90:10:0.5) as eluent to give 0.50 g (8% over two steps) of the free base of the title compound as a colorless oil. An analytical sample was precipitated as its HCl salt with HCl/ether: mp 199–200° C. Anal. (C$_{10}$H$_{15}$ClN$_4$.HCl) C, H, N.

Step 4: cis-2,6-Dimethyl-1-{3-[2-(3-pyridinyloxy)ethoxy]-2-pyrazinyl}piperazine, Fumarate.

The title compound was prepared starting from 2-(3-pyridyloxy)ethanol (from Example 150, Step 1) and the product obtained in Step 3 according to the procedure of Example 162, Step 2. The crude product was purified by column chromatography on silica using CHCl$_3$/MeOH/NH$_4$OH (95:5:0.2) as eluent. After evaporation of the solvent from the combined pure fractions, the resulting oil was crystallized as its fumaric acid salt from MeOH/ether to afford 0.29 g (36%) of the title compound as white crystals: mp 157° C. (dec). Anal. (C$_{17}$H$_{23}$N$_5$O$_2$.C$_4$H$_4$O$_4$) C, H, N.

Example 180

N-[8-(2-{[31-piperazinyl)-2-pyrazinyl]oxy}ethoxy)-2-quinolinyl]acetamide

Step 1: tert-Bu tyl 4-(3-{2-[(2-amino-8-quinolinyl)oxy]ethoxy}-2-pyrazinyl)-1-piperazinecarboxylate.

The product of Example 177, Step 1 (503 mg, 2.46 mmol) and 2-chloro-3-(4-tert-butoxycarbonyl-1-piperazinyl)pyrazine (659 mg, 2.21 mmol, from Example 52, Step 1) were dissolved in dry dioxane (20 mL). K-t-Bu (305 mg, 2.72 mmol) was added and the reaction mixture was heated. The reaction mixture was heated at 80° C. under inert atmosphere for 3.5 h (monitoring by MS). The reaction mixture was concentrated in vacuo and the residue was dissolved in EtOAc. The organic phase was washed with H$_2$O and the aqueous phase was back-extracted with CH$_2$Cl$_2$. The combined organic phases were washed with brine and dried (MgSO$_4$). Evaporation of the solvents gave a yellow oil (1.37 g), that was purified by column chromatography using EtOAc/Et$_3$N (95:5) as eluent to give the title compound as a yellow solid: yield 898 mg (87%); MS m/z 467 (M+H)$^+$. Anal. (C$_{24}$H$_{30}$N$_6$O$_4$.0.9H$_2$O)C, H, N.

Step 2: tert-Butyl 4-[3-(2-{[2-(acetylamino)-8-quinolinyl]oxy}ethoxy)-2-pyrazinyl]-1-piperazinecarboxylate.

The product obtained in Step 1 (502 mg, 1.08 mmol) was dissolved in pyridine. Ac$_2$O (0.42 mL, 4.45 mmol) was added, and the reaction mixture was stirred under inert atmosphere at room temperature for 5 h. Concentration in vacuo afforded a yellow oil, which was purified by column chromatography using EtOAc/Et$_3$N (95:5) as eluent to give the title product as a yellow solid: yield 531 mg (97%); MS m/z 509 (M+H)$^+$. Anal. (C$_{26}$H$_{32}$N$_6$O$_5$.0.4H$_2$O)C, H, N.

Step 3: N-[8-(2-{[3-(1-piperazinyl)-2-pyrazinyl]oxy}ethoxy)-2-quinolinyl]acetamide.

TFA (1.5 mL) was added to a solution of the product from Step 2 (112 mg, 0.22 mmol) in CH$_2$Cl$_2$(1.5 mL) at 0° C. and the mixture was stirred under inert atmosphere for 1 h. The reaction mixture was diluted with CH$_2$Cl$_2$ and washed with 2 M aqueous NaOH (×4) and brine. The organic layer was dried (MgSO$_4$) and concentrated. The crude solid product (83 mg) was purified by column chromatography on silica using CHCl$_3$/MeOH (9:1)+1% NH$_3$ as eluent to give the title compound as an oil that solidified after repeated additions of pentane: yield 67 mg (75%); MS m/z 409 (M+H)$^+$. Anal. (C$_{21}$H$_{24}$N$_6$O$_3$.0.6H$_2$O.0.1C$_5$H$_{12}$) C, H, N.

Example 181

N-Methyl-8-(2-{[3-(1-piperazinyl)-2-pyrazinyl]oxy}ethoxy)-2-quinolinamine

Step 1: 2-(Methylamino)-8-quinolinol.

To a solution of 2-chloro-8-hydroxyquinoline*(2.0 g, 11.1 mmol) in EtOH (40 mL) was added H$_2$NMe (40% aqueous solution, 40 mL, 464 mmol). The mixture was heated in a sealed Pyrex tube at 100° C. for 24 h. The solvent was evaporated and the resulting crude product was purified by column chromatography [gradient: CH$_2$Cl$_2$/MeOH (99:1) to 1% NH$_4$OH in C H$_2$Cl$_2$/MeOH (80:20)] to give the title compound as a black-green solid. Yield 1.31 g (67%); MS m/z 174 (M)$^+$. Anal. (C$_{10}$H$_{10}$N$_2$O)C, H, N.
*Prepared as described in J. Org. Chem. 1971, 36, 3490–3493.

Step) 2: 2-{[2-(Methylamino)-8-quinolinyl]oxy}-1-ethanol.

The title compound was prepared according to the procedure of Example 91, Step 1, starting form the product obtained in Step 1 above. The crude product was purified by, column chromatography on silica gel using EtOAc/MeOH (95:5) containing Et$_3$N (2%). Solid, yield 1.21 g (88%); MS m/z 218 (M)$^+$. Anal. (C$_{12}$H$_{14}$N$_2$O$_2$.0.6H$_2$O)C, H, N.

Step 3: N-Methyl-8-(2-{[3-(1-piperazinyl)-2-pyrazinyl]oxy}ethoxy)-2-quinolinamine.

The title compound was prepared according to the procedure of Example 90, Step 2, starting from the product obtained in Step 2 above and 2-chloro-3-(1-piperazinyl)piperazine (from Example 90, Step 1). The crude product was purified by column chromatography (gradient: 1% NH$_4$OH in EtOAc/MeOH (90:10) to 1% NH$_4$OH in EtOAc/MeOH (80:20) in first purification step and gradient 0.5% NH$_4$OH in CHCl$_3$/MeOH (95:5) to 1% NH$_4$OH in CHCl$_3$/MeOH (90:10) in second purification). Yield 31%; mp 54.0–56.5° C.; MS m/z 381 (M+H)$^+$. Anal. (C$_{20}$H$_{24}$N$_6$O$_2$.0.5H$_2$O)C, H, N.

Example 182

2-[2-(1,3-Benzodioxol-4-yloxy)ethoxy]-3-(2-methyl-1-piperazinyl)quinoxaline, Hydrochloride Step 1: Step 1: 4-tert-Butoxycarbonyl-2-methylpiperazine.*

The title compound was prepared according to the procedure described in Example 172, Step 1, except that racemic 2-methylpiperazine was used instead of (2R)-methylpiperazine. Yield 82% of the free base. An analytical sample was prepared by conversion to the hydrochloride salt: mp 162° C. (dec). Anal. (C$_{10}$H$_{20}$N$_2$O$_2$.HCl) C, H, N.
*Previously described in J. Med. Chem. 1993, 36, 690–698.

Step 2: tert-Butyl 4-(3-chloro-2-quinoxalinyl)-3-methyl-1-piperazinecarboxylate.

A mixture of the title product from Step 1 above (12.3 g, 61.4 mmol), 2,3-dichloroquinoxaline (14.4 g, 72.2 mmol), and K$_2$CO$_3$ (13.8 g, 100 mmol) in DMF (100 mL) was stirred at 85° C. for 15 h. The mixture was filtered and the resulting filtrate was concentrated under reduced pressure. The residue was purified by chromatography on silica gel using petroleum ether/EtOAc (94:6) as eluent to give 5.8 g (36%) of a reddish oil that crystallized on standing: mp 93–97° C. Anal. (C$_{18}$H$_{23}$ClN$_4$O$_2$)C, H, N.

Step 3: 2-(1,3-Benzodioxol-4-yloxy)ethanol.

A mixture of 1,3-benzodioxol-4-ol*(0.74 g, 5.36 mmol), ethylene carbonate (0.47 g, 5.3 mmol) and K$_2$CO$_3$ (0.67 g, 4.8 mmol) in DMF (30 mL) was heated at 150° C. After the evolution of carbon dioxide had ceased (1 h), the reaction mixture was filtered and concentrated. The crude product was purified by chromatography on silica gel using petroleum ether/EtOAc (70:30) as eluent to give 0.64 g (65%) of the title product as an oil which spontaneously crystallized to a white solid: mp 56–57° C. Anal. ($C_9H_{10}O_4$) C, H.
*See Example 78.

Step 4: 2-[2-(1,3-Benzodioxol-4-yloxy)ethoxy]-3-(2-methyl-1-piperazinyl)quinoxaline, Hydrochloride.

KO-t-Bu (0.41 g, 3.7 mmol) was added to a solution of 2-(1,3-benzodioxol-4-yloxy)ethanol (0.33 g, 1.8 mmol; from Step 3 above) in dioxane (15 mL). After 15 min of stirring at room temperature, the title compound from Step 2 above (0.73 g, 2.0 mmol) was added and the mixture was stirred at 95° C. for 1.5 h. The reaction mixture was filtered through a pad of Celite, concentrated in vacuo, and the residue was purified by chromatography on silica gel using petroleum ether/EtOAc (9:1) as eluent. The resulting oil was dissolved in $CH_2Cl_2$/TFA (1:1, 20 mL) and stirred at room temperature for 15 h. The mixture was concentrated and the resulting oil was co-evaporated twice with 2 M HCl. The residue was recrystallized from water to give 0.22 g (26%) of the title compound as white crystals: mp 133–138° C.; HRMS m/z calcd for $C_{17}H_{22}N_4O_2$ (M)+408.1798, found 408.1782. Anal. ($C_{22}H_{24}N_4O_4 \cdot HCl\ H_2O$)C, H, N;

Example 183

5,6-Dimethyl-2-(2-phenoxyethoxy)-3-(1-piperazinyl)pyrazine, Dihydrochloride

Step 1. 2-Chloro-5,6-dimethyl-3-(1-piperazinyl)pyrazine.

The title compound was prepared according to the procedure described in Example 90, Step 1, starting from 2,3-dichloro-5,6-dimethylpyrazine*(0.60 g, 3.39 mmol) and piperazine (0.88 g, 10.2 mmol). Yield 0.51 g (66%). MS m/z 226 (M)+.
*Prepared as described in *J. Am. Chem. Soc.* 1956, 78, 4071–4077.

Step 2: 5,6-Dimethyl-2-(2-phenoxyethoxy)-3-(1-piperazinyl)pyrazine, Dihydrochloride.

The product from Step 1 above (506 mg, 2.20 mmol) and 2-phenoxyethanol (370 mg, 2.70 mmol) was dissolved in dioxane (10 mL). KO-t-Bu (626 mg, 5.60 mmol) was added and the resulting mixture was stirred at 95° C. for 4 h. The solvent was evaporated and the residue was purified by chromatography on silica gel to give the free base as a yellow oil. The free base was converted to the dihydrochloride salt which was obtained as a monohydrate: yield 0.46 g (50%); mp 138–140° C. Anal. ($C_{18}H_{24}N_4O_2 \cdot 2HCl \cdot H_2O$)C, H, N.

Example 184

1-[2-(2-Phenoxyethoxy)phenyl]piperazine, Hydrochloride

Step 1: tert-Butyl 4-(2-hydroxyphenyl)-1-piperazinecarboxylate.

Triethylamine (8.23 mL, 59.5 mmol) was added to a stirred solution of 2-(1-piperazinyl)phenol dihydrobromide (9.87 g, 29.0 mmol) in a mixture of water and dioxane (1:1, 60 mL). The reaction mixture was cooled on an ice-bath (0° C.) and di-tert-butyldicarbonate (6.33 g, 29.0 mmol) was added in one portion. The resulting mixture was allowed to warm to room temperature and stirred for 15 h. The mixture was concentrated to a small volume. Water (20 mL) was added and the white crystals formed were filtered off and dried (1 mm Hg, 70° C.) to give a quantitative yield (7.24 g) of the title compound: mp 115–117° C. Anal. ($C_{15}H_{22}N_2O_3$) C, H, N.

Step 2: 1-[2-(2-Phenoxyethoxy)phenyl]piperazine, Hydrochloride.

The product from Step 1 above (0.55 g, 2.0 mmol) was added to a stirred solution of NaO-t-Bu (0.55 g, 2.0 mmol) in DME (5 mL). After 5 min, β-bromophenetole (0.56 g, 2.8 mmol) was added, and the reaction was stirred at 55° C. for 15 h, 2 M HCl was added, and the reaction mixture was stirred for another 3 h. The reaction mixture was concentrated in vacuo and the residue was partitioned between 2 M NaOH/CHCl$_3$. The aqueous phase was extracted with CHCl$_3$ (×3). The combined organic layers were dried (MgSO$_4$), concentrated, and the residue was purified by chromatography on silica gel using CHCl$_3$/MeOH/NH$_4$OH (90:10:0.4) as eluent to give the free base of the title compound. The free base was treated with HCl/ether, and the resulting hydrochloride salt was dried (80° C., 1 mmHg) to afford 0.254 g (35%) of the title compound as a light brown semi-solid material that solidified upon standing. Anal. ($C_{18}H_{22}N_2O_2 \cdot HCl \cdot H_2O$)H, N, C: calc, 61.27; found, 61.9.

Example 185

1-[3-(2-Phenoxyethoxy)-2-pyridinyl]piperazine, Dihydrochloride

Step 1: 2-Chloro-3-(2-phenoxyethoxy)pyridine.

A mixture of 2-chloro-3-hydroxypyridine (3.0 g, 23.1 mmol), β-bromophenetole (4.66 g, 23.2 mmol), and K$_2$CO$_3$ (8.0 g, 57.9 mmol) in DMF (50 mL) was heated at 100° C. for 1.5 h. The solvent was removed under reduced pressure and the residue was partitioned between EtOAc and H$_2$O. The organic phase was dried (MgSO$_4$), filtered, and the solvent evaporated. The solid residue was triturated with a small amount of ether and dried (65° C., 1 mmHg) to afford 4.23 g (74%) of the title product as white crystals: mp 77–78° C. Anal. ($C_{13}H_{12}ClNO_2$) C, H, N.

Step 2: 1-[3-(2-Phenoxyethoxy)-2-pyridinyl]piperazine, Dihydrochloride.

A mixture of the product from Step 1 above (0.84 g, 3.1 mmol) and piperazine hexahydrate (5.3 g, 27.3 mmol) was heated in a sealed tube at 165° C. for 1 h. After cooling, the mixture was diluted with water (100 mL) and extracted twice with EtOAc. The combined and dried (MgSO$_4$) organic phases were concentrated in vacuo and the residue was purified by chromatography on silica gel using CHCl$_3$/MeOH/NH$_4$OH (90:10:0.4) as eluent to give the free base of the title compound. The free base was treated with HCl/ether, and the resulting dihydrochloride salt was dried (80° C., 1 mmHg) to afford 0.598 g (52%) of the title compound as a light yellow solid: mp 91–120° C. Anal. ($C_{17}H_{21}N_3O_2 \cdot 2HCl$) C, H, N.

Example 186

2-(2,3-Dihydrobenzofuran-7-yloxy)ethyl 3-(1-piperazinyl)-2-pyrazinyl ether, Maleate The title compound obtained in Example 140, Step 2, (390 mg, 0.85 mmol) was dissolved in MeOH (50 mL) and hydrogenated over 10% Pd/C (50 mg) at atmospheric pressure for 7 h. The reaction mixture was filtered through Celite and concentrated. The residue was purified by chromatography on silica gel using EtOAc/MeOH/Et$_3$N (9:1:0.25) as eluent to give 57 mg (20%) of the free base of the title compound. The free base was converted to the maleate and recrystallized from MeOH/ether: mp 149–154° C.; MS m/z 343 (M+H)+. Anal. ($C_{18}H_{22}N_4O_3 \cdot 1.1C_4H_4O_4 \cdot 0.6H_2O$)C, H, N.

Example 187

5-Chloro-2-(1-piperazinyl)-3-[2-(3-pyridinyloxy)ethoxy]pyrazine, Fumarate

Step 1: 3,5-Dichloro-2-(1-piperazinyl)pyrazine.

To a suspension of 2-chloro-3-(1-piperazinyl)pyrazine (11.7 g, 58.7 mmol; from Example 90, Step 1) in CHCl$_3$ (50 mL) was N-chlorosuccinimid (14.4 g, 108 mmol) added and the mixture was heated at reflux for 30 minutes. The reaction mixture was cooled to ambient temperature and extracted twice with water. The combined aqueous phases were made alkaline (11M NaOH), saturated with NaCl, cooled, and extracted with EtOAc (×3). Concentration of the combined, dried (MgSO$_4$), organic phases afforded 6.12 g (45%) of the title compound as a brown oil which crystallized upon standing: mp 89–97° C. Anal. (C$_8$H$_{10}$Cl$_2$N$_4$.⅓H$_2$O)C, H, N.

Step 2: 5-Chloro-2-(1-piperazinyl)-3-[2-(3-pyridinyloxy)ethoxy]pyrazine, Fumarate The title compound was prepared starting from 2-(3-pyridyloxy)ethanol (from Example 150, Step 1) and the product from Step 1 according to the procedure described in Example 162, Step 2. The crude product was purified by column chromatography on silica using CHCl$_3$/MeOH/NH$_4$OH (95:5:0.2, followed by 90:10:0.3) as eluent. After evaporation of the solvent from the combined pure fractions, the resulting oil was crystallized as its fumaric acid salt from MeOH/ether to afford 3.06 g (39%) of the title compound as light yellow crystals mp 162° C. (dec). Anal. (C$_{15}$H$_{18}$ClN$_5$O$_2$·C$_4$H$_4$O$_4$)

Example 188

5-Bromo-2-(1-piperazinyl)-3-[2-(3-pyridinyloxy)ethoxy]pyrazine, Acetate

Step 1: 5-Bromo-3-chloro-2-(1-piperazinyl)pyrazine.

To a mixture of 2-chloro-3-(1-piperazinyl)pyrazine (5.94 g, 30 mmol, from Example 90, Step 1) and Na$_2$CO$_3$ (6.0 g, 57 mmol) in AcOH (25 mL) was added a solution of Br$_2$ (6.00 g 38.0 mmol) in AcOH (25 mL) dropwise at room temperature. The reaction mixture was stirred overnight. Water (50 mL) was added and the solution was stirred for 30 min and then concentrated to a small volume. Water (20 mL) was added and the solution was basified to pH 9 by adding solid Na$_2$CO$_3$. The mixture was extracted with CH$_2$Cl$_2$ containing 10% MeOH. The combined extract was evaporated to dryness and the residue was recrystallized from MeOH to give 7.43 g (89%) of the title compound: mp 114–115° C. HRMS m/z calcd for C$_8$H$_{10}$BrClN$_4$ (M)$^+$ 275.9777, found 275.9765.

Step 2: 5-Bromo-2-(1-piperazinyl)-3-[2-(3-pyridinyloxy)ethoxy]pyrazine, Acetate.

To a solution of the product obtained in Step 1 above (3.73 g, 13.5 mmol) and 2-(3-pyridyloxy)ethanol (2.06 g, 14.8 mmol, from Example 150, Step 1) in DMSO (10 mL) was added NaH (50% in mineral oil; 0.93 g, 20 mmol) at room temperature. The mixture was stirred at room temperature overnight. EtOAc (100 mL) was added and the mixture was washed with water, dried over Na$_2$CO$_3$ and filtered. AcOH (1.0 mL) was added to the filtrate. Crystals were formed upon cooling. The crystals were collected, washed with ethyl ether, and dried in vacuum to give 2.45 g (41%) of the title product: mp 108–109° C. Anal. (C$_{15}$H$_{18}$BrN$_5$O$_2$·CH$_3$COOH)C, H, N.

Example 189

5-Methyl-2-(1-piperazinyl)-3-[2-(3-pyridinyloxy)ethoxy]pyrazine

Step 1: tert-Butyl 4-(5-bromo-3-[2-(3-pyridinyloxy)ethoxy]-2-pyrazinyl)-1-piperazinecarboxylate.

To a solution of the free base of the product obtained in Example 188. Step 2, (0.70 g. 1.85 mmol) in EtOAc (10 mL) and Et$_3$N (2 mL) was added (T-BuOC)$_2$O (0.46 g, 2.0 mmol). The mixture was stirred at room temperature overnight. The reaction mixture was washed with 2 M aqueous NaOH and brine, dried over Na$_2$CO$_3$ and concentrated. The residue was purified by column chromatography on silica gel, using ethyl ether/hexane (1:3 to 3:1) as eluent to give 0.64 g (72%) of the title product as an oil. MS m/z 481 (M)$^+$.

Step 2: tert-Butyl 4-{5-Methyl-3-[2-(3-pyridinyloxy)ethoxy]-2-pyrazinyl}-1-piperazinecarboxylate.

To a mixture of the product obtained in Step 1 (0.38 g, 0.8 mmol) and NiCl$_2$(dppp) (0.054 g, 0.10 mmol) in dry THF (3 mL) was added dropwise 2N dimethylzinc in toluene (0.5 mL, 1 mmol) at room temperature under stirring. [The reaction was monitored by TLC on SiO$_2$ using ethyl ether/n-hexane (1:1)]. After 4 h, an additional portion (0.3 mL, 0.6 mmol) of the dimethylzinc solution was added. The reaction was stirred for another 2 h and quenched with water (3 mL). The mixture was extracted with ethyl acetate. The organic extract was washed with brine, dried over Na$_2$CO$_3$ and concentrated to give 0.29 g of a yellowish oil. Column chromatography on silica gel, using ethyl ether/n-hexane (1:1 to 4:1) as eluent, gave 0.19 g (57%) of the title product as an oil. MS m/z 415 (M)$^+$. HRMS m/z calcd for C$_{21}$H$_{29}$N$_5$O$_4$ (M)$^+$415.2220, found 415.2200.

Step 3: 5-Methyl-2-(1-piperazinyl)-3-[2-(3-pyridinyloxy)ethoxy]pyrazine.

To a solution of the product obtained in Step 2 (0.507 g, 1.22 mmol) in CH$_2$Cl$_2$ (3.0 mL) was added TFA (1.5 mL) at 5° C. The solution was stirred for 2 h and evaporated to dryness. The residue was dissolved in water (5 mL) and the solution was basified with 50% aqueous NaOH to pH>13 and extracted with EtOAc. The organic extract was dried over Na$_2$CO$_3$. Evaporation of the solvent gave 0.51 g of the free base. Attempts to prepare a salt of the free base from oxalic acid, fumaric acid or acetic acid failed. The free base was re-generated [treatment with 10% NH$_3$ aqueous solution, extraction with EtOAc and drying (Na$_2$CO$_3$)]to give 0.15 g (40%) of the title compound as an oil. MS m/z 315 (M)$^+$. HRMS m/z calcd for C$_{16}$H$_{21}$N$_5$O$_2$ (M)$^+$315.1695, found 311.1701.

Example 190

2-{2-[(3-Methoxy-2-pyrazinyl)oxy]ethoxy}-3-(1-piperazinyl)pyrazine, Maleate

Step 1: tert-Butyl 4-(3-{2-[(3-Chloro-2-pyrazinyl)oxy]ethoxy}-2-pyrazinyl)-1-piperazinecarboxylate.

NaH (50% in mineral oil; 0.153 g, 3.50 mmol) was added to a stirred solution of 2-[3-(4-tert-butoxycarbonyl-1-piperazinyl)-2-pyrazinyloxy]ethanol (1.00 g, 3.08 mmol; prepared in Example 52, Step 2) and 2,3-dichloropyrazine (1.0 g, 6.71 mmol) in dioxane (10 mL). The reaction was stirred in a sealed tube at 100° C. overnight. The reaction mixture was poured into water and extracted with diethyl ether. The ether phase was dried (MgSO$_4$), concentrated and purified by column chromatography on silica using toluene/EtOAc (7:3) as eluent to give 0.823 g (61%) of the title product: Pos-EI-MS shows M$^+$ and 14 ions supporting the stated structure. HRMS m/z calcd for C$_{19}$H$_{25}$ClN$_6$O$_4$ (M)$^+$ 436.1626, found 436.1606.

Step 2: tert-Butyl 4-(3-{2-[(3-methoxy-2-pyrazinyl)oxy]ethoxy}-2-pyrazinyl)-1-piperazinecarboxylate.

NaH (50% in mineral oil; 0.010 g, 2.1 mmol) was added to a stirred solution of the product from Step 1 (0.38 g, 0.87 mmol) in dioxane (8 mL) and MeOH (2 mL) in a reaction tube. As the gas evolution had ceased, the tube was sealed and the mixture was stirred at 100° C. for 15 min. The reaction was poured into water and extracted with toluene, dried (MgSO$_4$) and concentrated. The residue was purified by column chromatography on silica using toluene/EtOAc (7:3) as eluent to give 0.178 g (47%) of the title product. Pos-EI-MS shows M$^+$ and 11 ions supporting the stated structure. HRMS m/z calcd for C$_{20}$H$_{28}$N$_6$O$_5$ (M)$^+$432.2121, found 432.2126.

Step 3: 2-{2-[(3-Methoxy-2-pyrazinyl)oxy]ethoxy}-3-(1-piperazinyl)pyrazine, Maleate.

The product from Step 2 (0.175 g, 0.40 mmol) product was treated with CH$_2$Cl$_2$/TFA/H$_2$O (50:45:5: 10 mL) for 30 min at room temperature, poured into 0.11M aqueous HCl and washed with toluene (×2). The aqueous phase was alkalinized to pH 11 with NaOH, and extracted with diethyl ether (×3). The organic layers were dried (MgSO$_4$) and concentrated to give 0.120 g (0.36 mmol) of the free base of the title product. Maleic acid (0.042 g, 0.36 mmol) in dioxane (0.5 mL) was added to a solution of the free base in dioxane (3 mL) and left to crystallize to give 0.147 g (82%) of the title product. Pos-EI-MS shows M$^+$ and 11 ions supporting the stated structure. HRMS m/z calcd for C$_{15}$H$_{20}$N$_6$O$_3$ (M)$^+$332.1597, found 332.1607.

Example 191

2-{(2-[((2-Methoxy-3-pyridinyl)oxy]ethoxy}-3-(1-piperazinyl)pyrazine, Fumarate

Step 1: 2-Bromo-3-(2-hydroxyethoxy)pyridine.

The title compound was prepared from 2-bromo-3-hydroxypyridine according to the procedure described in Example 91, Step 1. Oil; yield 2.33 g (76%).

Step 2: 3-(2-Hydroxyethoxy)-2-methoxypyridine.

A mixture of the product obtained in Step 1 (2.33 g, 10.7 mmol) and NaOMe (0.634 mg, 11.8 mmol) in MeOH (50 mL) was refluxed overnight. The reaction mixture was filtered and concentrated. The residue was purified by column chromatography on silica, using CH$_2$Cl$_2$/MeOH/heptane (4:1:5) as eluent, to give 0.81 g (45%) of the title compound as a colorless oil.

Step 3: 2-{2-[(2-Methoxy-3-pyridinyl)oxy]ethoxy}-3-(1-piperazinyl)pyrazine, Fumarate.

2-Chloro-3-(1-piperazinyl)pyrazine (0.454 g, 2.13 mmol, from Example 90, Step 1) was added to a mixture of the product obtained in Step 2 (0.380 g, 2.25 mmol) and NaOt-Bu (0.432 g, 4.50 mmol) in dioxane (25 mL). The reaction mixture was stirred at 90° C. for 2 h and then quenched by adding MeOH (0.6 mL, 13.3 mmol). Silica gel was added and the mixture was filtered and concentrated in vacuo). The residue was purified by column chromatography using CHCl$_3$/MeOH/heptane (4:1:5) containing 0.2% aqueous NH$_3$ as eluent to give 0.257 g (40%) of the free base of the title compound as a colorless oil. The free base was dissolved in MeOH (3 mL) and converted into its fumarate salt by adding fumaric acid (0.104 g, 0.87 mmol) in MeOH (3 mL) followed by addition of ether to obtain 0.214 g (56%) of the title compound as white needles: mp 181–183° C.; Anal. (C$_{20}$H$_{25}$N$_5$O$_7$) C, H, N.

Example 192

(2R)-1-(3-{2-[((2-Methoxy-3-pyridinyl)oxy]ethoxy)}-2-pyrazinyl)-2-methylpiperazine, Fumarate Step 1: (R)-3-Methyl-1-tritylpiperazine.

(2R)-Methylpiperazine-L-(+)-tartrate* (300 g, 1.2 mol) was added to a hot stirred solution of KOH (240 g, 4.3 mol) in H$_2$O (240 mL). Two phases were formed and the mixture was cooled to room temperature and extracted with CH$_2$Cl$_2$ (3×400 mL). The extracts were dried over K$_2$CO$_3$ and filtered. Trityl chloride (260 g, 0.93 mol) was slowly added to a well-stirred solution of the generated (R)-2-metyhylpiperazine* in CH$_2$Cl$_2$ under cooling (exotermic). After 45 min, the solution was poured into a solution of K$_2$CO$_3$ (140 g, 1.00 mol) in water (500 mL). The resulting organic phase was separated and dried over K$_2$CO$_3$, and the solvent was evaporated. This gave 370 g of the title product as an oil, which was used without purification.

*Previously reported in *J. Med. Chem.* 1990, 33, 1645–1656.

Step 2: (2R)-1-(3-Chloro-2-pyrazinyl)-2-methylpiperazine.

A mixture of the product obtained in Step 1 above, 2,3-dichloropyrazine (154 g, 1.00 mmol) and K$_2$CO$_3$ (160 g, 1.20 mol) in DMF (1 L) was heated at 110° C. for 20 h with vigorous stirring. (TLC monitoring system: CHCl$_3$: EtOH (20:1); silica). The mixture was cooled and poured slowly into water (6 L) with stirring. The solid was collected, washed with water, dried, dissolved in CHCl$_3$ (1 L), diluted with n-heptane (1 L), and filtered through SiO$_2$. Solvents were evaporated off. The resulting oil was dried under vacuum (3 mm/50° C., 30 min) to remove the DMF. The oil was dissolved in hot ethanol (1 L.), and HCl (10% aqueous solution, 300 mL) was added slowly. Trityl carbinol began to crystallize out after 10 min. After 30 min, the formed trityl carbinol was filtered off and the ethanol was evaporated. The aqueous solution was extracted by ether (2×200 mL) and made basic by addition of K$_2$CO$_3$ to pH 12. The alkaline layer was extracted with CHCl$_3$ (3×200 mL). The combined organic layers were dried (K$_2$CO$_3$) and concentrated to give 140 g (66%) of the title compound.

Step 3: (2R)-1-(3-{2-[(2-Methoxy-3-pyridinyl)oxy]ethoxy}-2-pyrazinyl)-2-methylpiperazine, Fumarate.

The product obtained in Step 2(0.494 g, 2.18 mmol) was added to a solution of 3-(2-hydroxyethoxy)-2-methoxypyridine (0.410 g, 2.42 mmol; from Example 191, Step 2) and NaOt-Bu (0.349 g, 3.63 mmol) in dioxane (25 mL) at 90° C. The reaction mixture was stirred at 90° C. for 2 h and then quenched by adding MeOH (0.6 mL, 13.3 mmol). Silica gel was added and the mixture was filtered and concentrated in vacuo. The residue was purified by column chromatography on silica using CHCl$_3$/MeOH/n-heptane (4:1:5) containing 0.2% aqueous NH$_3$ as eluent to give 0.382 g (45%) of the free base of the title compound as a colorless oil. Part of the free base (0.150 g, 0.48 mmol) was converted to its fumarate salt to give 0.061 g (28%) of the title compound: mp 141–143° C. Anal. (C$_{21}$H$_{27}$N$_5$O$_7$.0.25H$_2$O) C, H, N.

Example 193

2-{2-[(2-Chloro-3-pyridinyl)oxy]ethoxy}-3-(1-piperazinyl)pyrazine, Fumarate

Step 1: 2-[(2-Chloro-3-pyridinyl)oxy]ethanol.

The title compound was prepared from 2-chloro-3-hydroxypyridine according to the procedure described in Example 91, Step 1. Oil; yield (77%; purity about 80% according to $^1$H NMR). This material was used without further purification in the next synthetic step. HRMS m/z calcd for C$_7$H$_8$ClNO$_2$ (M)$^+$173.0240. Found: 173.0244.

Step 2: 2-{2-[(2-Chloro-3-pyridinyl)oxy]ethoxy}-3-(1-piperazinyl)pyrazine, Fumarate.

The title compound was prepared according to the procedure of Example 90, Step 2, except that the reaction was carried out at room temperature, starting from the product obtained in Step 1 above and 2-chloro-3-(1-piperazinyl) pyrazine (from Example 90, Step 1). The crude product was purified by column chromatography on silica. Using CHCl$_3$/MeOH/NH$_4$OH(95:5:0.25, followed by 90:10:03) as eluent. The free base of the title compound was converted to the fumarate salt. Yield 41%; mp 200° C. Anal. (C$_{18}$H$_{18}$ClN$_5$O$_2$.C$_4$H$_4$O$_4$) C, H, N.

Example 194

(2R)-1-(3-{2-[(2-Chloro-3-pyridinyl)oxy]ethoxy}-2-pyrazinyl)-2-methylpiperazine, Fumarate The title compound was prepared according to the procedure of Example 192, Step 3, except that the reaction was carried out at room temperature and replacing 3-(2-hydroxyethoxy)-2-methoxypyridine with 2-[(2-chloro-3-pyridinyl)oxy]ethanol (obtained in Example 193, Step 1). The crude product was purified by column chromatography on silica, using $CHCl_3/MeOH/NH_4OH$ (97:3:0.2, followed by 95:5:0.25) as eluent. The free base of the title compound was converted to the fumarate salt: yield 25%; mp 147° C. Anal. ($C_{16}H_{20}ClN_5O_2.C_4H_4O_4$) C, H, N.

Example 195

2-{2-[(2-Bromo-3-pyridinyl)oxy]ethoxy}-3-(1-piperazinyl)pyrazine, Fumarate

The title compound was prepared according to the procedure of Example 90, Step 2, except that the reaction was carried out at room temperature, starting from 2-bromo-3-(2-hydroxyethoxy)pyridine (obtained in Example 191, Step 1) and 2-chloro-3-(1-piperazinyl)pyrazine (from Example 90, Step 1). Yield 39%; mp 202° C. Anal. ($C_{15}H_{18}BrN_5O_2$).$C_4H_4O_4$) C, H, N.

Example 196

(2R)-1-(3-{2-[(2-Bromo-3-pyridinyl)oxy]ethoxy}-2-pyrazinyl)-2-methylpiperazine, Fumarate The title compound was prepared according to the procedure of Example 192, Step 3, except that the reaction was carried out at room temperature, starting from 2-bromo-3-(2-hydroxyethoxy)pyridine (obtained in Example 191, Step 1) and (2R)-1-(3-chloro-2-pyrazinyl)-2-methylpiperazine (from Example 192. Step 2). Yield 23%: mp 154° C. Anal. ($C_{16}H_{20}BrN_5O_2).C_4H_4O_4$) C, H, N,

Example 197

2-(2-{[2-(Methylsulfanyl)-3-pyridinyl]oxy}ethoxy)-3-(1-piperazinyl)pyrazine, Fumarate Step 1: 2-{[2-(Methylsulfanyl)-3-pyridinyl]oxy}ethanol.

To a suspension of sodium thiomethoxide (3.01 g, 42.9 mmol) in dry DMF (30 mL) was 2-[(2-chloro-3-pyridinyl)oxy]ethanol (7.82 g, 45.1 mmol, from Example 193, Step 1) added and the reaction mixture was stirred at ambient temperature for 1 h. The solvent was removed under reduced pressure and the residue was partitioned between brine/1 M aqueous NaOH and $CHCl_3$. The aqueous phase was extracted with an additional portion of $CHCl_3$ and the combined organic layers were dried ($MgSO_4$) and concentrated. The resulting red oil was purified by column chromatography on silica using toluene/$Et_3$N/MeOH (96:2:2) as eluent to give 3.0 g (36%) of the title compound as brownish crystals: mp 80° C. Anal. ($C_7H_{11}$, $NO_2$S)C, H, N.

Step 2: 2-(2-{[2-(Methylsulfanyl)-3-pyridinyl]oxy}ethoxy)-3-(1-piperazinyl)pyrazine, Fumarate.

The title compound was prepared according to the procedure of Example 90, Step 2, starting from from 2-chloro-3-(1-piperazinyl)pyrazine (from Example 90, Step 1) and the product obtained in Step 1 above. The free base of the title compound was converted to its fumarate salt: yield 47%; mp 201° C. Anal. ($C_{16}H_{21}N_5O_2S.C_4H_4O_4$) C, H, N.

Example 198

(2R)-2-Methyl-1-[3-(2-{[2-(methylsulfanyl)-3-pyridinyl]oxy}ethoxy)-2-pyrazinyl]piperazine, Fumarate The title compound was prepared according to the procedure of Example 192. Step 3, starting from (2R)-1-(3-chloro-2-pyrazinyl)-2-methylpiperazine (from Example 192, Step 2) and the product of Example 197, Step 1. The free base of the title compound was converted to the fumarate salt: yield 39%: mp 179° C. Anal. ($C_{17}H_{23}N_5O_2S.C_4H_4O_4$) C, H, N.

Example 199

2-{2-[(2-Ethoxy-3-pyridinyl)oxy]ethoxy}-3-(1-piperazinyl)pyrazine, Fumarate

Step 1: 2-Bromo-3-(2-{[tert-butyl(dimethyl)silyl]oxy}ethoxy)pyridine.

A solution of dimethyl-t-butylsilyl chloride (11.1 g, 74 mmol) in DMF (30 mL) was added to a suspension of 2-bromo-3-(2-hydroxyethoxy)pyridine (15.3 g, 70 mmol; obtained in Example 191, Step 1) and imidazole (10.0 g, 147 mmol) in DMF (30 mL). The reaction mixture was stirred at ambient temperature for 2 h, diluted with 0.5 M aqueous NaOH (0.7 L), and extracted twice with toluene. The combined organic phases were washed once with water, dried ($MgSO_4$), and concentrated. The resulting oil was treated with a mixture of petroleum ether and ethyl acetate (95:5; 50 mL) and an analytical sample of white crystals was collected. The remaining crystals were mixed with the filtrate, the solvent was evaporated and the resulting crude product was used directly in the next step. Solid; yield 18.3 g (78%); mp 81° C. Anal. ($C_{13}H_{22}BrNO_2Si$) C, H, N.

Step 2: 2-[(2-Ethoxy-3-pyridinyl)oxy]ethanol.

The product obtained in Step 1 above (13.2 g, 39.7 mmol) was added to sodium ethoxide in EtOH [prepared from Na (10.5 g, 457 mmol) and EtOH (200 mL)]. The resulting mixture was heated at 70° C. overnight. After cooling to ambient temperature, the reaction mixture was diluted with ice water (0.8 L) and extracted with EtOAc (×4). The combined organic phases were washed twice with brine, dried ($MgSO_4$) and concentrated. The resulting dark red oil was purified by column chromatography on silica using toluene/$Et_3$N (95:5), followed by (90:10), as eluent to give 3.0 g (41%) of the title product as a red oil. HRMS m/z calcd for $C_9H_{13}NO_3$ (M)$^+$183.0896. Found: 183.0895.

Step 3: 2-{2-[(2-Ethoxy-3-pyridinyl)oxy]ethoxy}-3-(1-piperazinyl)pyrazine, Fumarate.

The title compound was prepared according to the procedure of Example 90 Step 2, starting from 2-Chloro-3-(1-piperazinyl)pyrazine (from Example 90, Step 1) and the product obtained in Step 2 above. The free base of the title compound was converted to its fumarate salt: yield 30%; mp 186° C. Anal. ($C_{17}H_{23}N_5O_3.C_4H_4O_4$) C, H, N.

Example 200

(2R)-1-(3-{(2-[(2-Ethoxy-3-pyridinyl)oxy]ethoxy}-2-pyrazinyl)-2-methylpiperazine, Fumarate The title compound was prepared according to the procedure of Example 192, Step 3, starting from (2R)-1-(3-chloro-2-pyrazinyl)-2-methylpiperazine (from Example 192, Step 2) and 2-[(2-ethoxy-3-pyridinyl)oxy]ethanol (from Example 199, Step 2). The free base of the title compound was converted to its fumarate salt: yield 17%; mp 179° C. Anal. ($C_{18}H_{25}N_5O_3.C_4H_4O_4$) C, H, N.

Example 201

5-Ethoxy-3-pyridinyl 2-({3-[(2R)-2-methylpiperazinyl]-2-pyrazinyl}oxy)ethyl ether, Fumarate Step 1: 2-[(5-Ethoxy-3-pyridinyl)oxy]-1-ethanol.

The title compound was prepared according to the procedure of Example 91, Step 1, starting from 5-ethoxy-3-pyridinol (1.0 g, 7.2 mmol). Yield: 1.23 g (93%). MS m/z 184 (M+H)$^+$.

Step 2: 5-Ethoxy-3-pyridinyl 2-({3-[(2R)-2-methylpiperazinyl]-2-pyrazinyl}oxy)ethyl ether, Fumarate.

To a stirred solution of the product obtained in Step 1 (660 mg, 3.60 mmol) in dioxane (6 mL) was added K-t-BuO (438 mg, 3.90 mmol). After 15 min, (2R)-1-(3-chloro-2-pyrazinyl)-2-methylpiperazine (638 mg, 3.0 mmol: from Example 192, Step 2) was added and the solution was stirred at 85° C. for 2 h. After cooling, CHCl$_3$ was added and the mixture filtered and concentrated in vacuo. The residue was purified by chromatography on silica gel using Cl$_2$Cl$_2$/methanol (9:1) as eluent to give the free base of the title compound (0.60 g, 56%). The free base was converted to the hydrochloride salt: yield 0:53 g (37%); mp. 101–104° C.; MS m/z 360 (M+H)$^+$. HRMS m/z calcd for C$_{18}$H$_{25}$N$_5$O$_3$ (M)$^+$359.1957, found 359.1943.

Example 202

3-[(2R)-2-Methylpiperazinyl]-2-pyrazinyl 2-(5-pyrimidinyloxy)ethyl ether, Fumarate The title product was prepared according to the procedure of Example 201, Step 2, starting from 2-(5-pyrimidinyloxy)-1-ethanol (505 Mg, 3.60 mmol; from Example 166, Step 1) and (2R)-1-(3-chloro-2-pyrazinyl)-2-methylpiperazine (638 mg, 3.00 mmol; from Example 192, Step 2). The residue was purified by column chromatography on silica gel using CH$_2$Cl$_2$/methanol (9:1) as eluent to give 456 mg (48%) of the free base of the title compound. The free base was converted to the hydrochloride: mp. 145–147° C.; MS m/z 317 (M+H)$^+$. Anal. (C$_{15}$H$_{20}$N$_6$O$_2$.1.3C$_4$H$_4$O$_4$) C, H, N.

Example 203

Step 1: 2-[(6-Chloro-3-pyridinyl)oxy]-1-ethanol.

The title compound was prepared according to the procedure of Example 91, Step 1, starting from 2-chloro-5-hydroxypyridine. Solid; yield 78%. MS m/z 173 (M)$^+$. Anal. (C$_7$H$_8$ClNO$_2$) C, H, N.

Step 2: 2-{2-[(6-Chloro-3-pyridinyl)oxy]ethoxy}-3-(1-piperazinyl)pyrazine, Maleate.

The title compound was prepared according to the procedure of Example 90, Step 2, starting from the product obtained in Step 1 above. The crude product was purified by column chromatography (gradient: EtOAc/MeOH (90:10)+1% NH$_3$ to EtOAc/MeOH (80:20)+1% NH$_3$) on silica to give 22% of the free base of the title compound as a colorless oil. Part of this material was converted to its maleate salt: mp 145.9–146.3° C.; MS m/z 336 (M+H)$^+$. Anal. (C$_{15}$H$_{18}$ClN$_5$O.C$_4$H$_4$O$_4$) C. H, N.

Example 204

2-{2-[(6-Methoxy-3-pyridinyl)oxy]ethoxy}-3-(1-piperazinyl)pyrazine, Maleate

Step) 1: 2-[(6-Methoxy-3-pyridinyl)oxy]-1-ethanol.

A mixture of the product of Example 203, Step 1 (513 mg. 2.96 mmol) and freshly prepared NaOMe (3.06 g, 56.6 mmol) in dry dioxane (25 mL) was heated in a sealed Pyrex tube at 130° C. for 24 h. The solvent was evaporated under reduced pressure and the residue was dissolved in CH$_2$Cl$_2$. The organic phase was washed with brine, dried (MgSO$_4$), and concentrated to give the crude product as an oil (430 mg). Purification by column chromatography, using isohexane/EtOAc (1:1) as an eluent, gave the title product as a white solid. Yield 258 mg (51%); MS m/z 169 (M)$^+$. Anal. (C$_8$H$_{11}$NO$_3$) C, H, N.

Step 2: 2-{2-[(6-Methoxy-3-pyridinyl)oxy]ethoxy}-3-(1-piperazinyl)pyrazine, Maleate.

The title compound was prepared according to the procedure of Example 90, Step 2, starting from the product obtained in Step 1 above. Yield of free base of the title product 90%. Part of this material was converted to its maleate salt: mp 151.8–152.6° C.; MS m/z 332 (M+H)$^+$. Anal. (C$_{16}$H$_{21}$N$_5$O$_3$.C$_4$H$_4$O$_4$) C, H, N.

Example 205

4-Methoxy-N,N-dimethyl-3-[(2-({3-[(2R)-2-methylpiperazinyl]-2-pyrazinyl}oxy)ethoxy]aniline, Fumarate Step 1: 5-(Dimethylamino)-2-methoxyphenol.

To a stirred solution of 5-amino-2-methoxyphenol (5.0 g, 36 mmol) in ethanol (250 mL), was added 33% formaldehyde (4×1.5 mL at times 0, 60 min, 140 min and 185 min) and sodium cyanoborohydride (4×0.8 g, at times 30 min, 120 min, 165 min and 210 min). After each addition of the hydride, pH was adjusted to ~6 using acetic acid. The mixture was stirred for an additional 2 h and then concentrated in vacuo. The residue was partitioned between brine/diethyl ether and the organic phase was dried and concentrated. The residue was purified by column chromatography on silica gel using hexane/EtOAc (7:3) as eluent to give 1.17 g (20%) of the title compound. MS m/z 168 (M+H)$^+$.

Step 2: 2-[5-(Dimethylamino)-2-methoxyphenoxy]-1-ethanol.

The title compound was prepared according to the procedure of Example 91. Step 1, starting from 5-(dimethylamino)-2-methoxyphenol (1.17 g, 7.0 mmol; front Step 1 above): Yield: 1.44 g (97%).

Step 3: 4-Methoxy-N,N-dimethyl-3-[2-({3-[(2R)-2-methylpiperazinyl]-2-pyrazinyl}oxy)ethoxy]aniline, Fumarate.

The title product was prepared according to the procedure of Example 192, Step 3, starting from the product obtained in Step 2 above (700 mg, 3.30 mmol) and (2R)-1-(3-chloro-2-pyrazinyl)-2-methylpiperazine (585 mg. 2.75 mmol; from Example 192, Step 2). The crude product was purified by column chromatography on silica gel using CH$_2$Cl$_2$/CH$_3$OH (9:1) as eluent to give the free base of the title compound. The free base was converted to the fumaric acid salt. Yield: 135 mg (10% over all); mp. 147–149° C.; MS m/z 388 (M+H)$^+$. Anal. (C$_{20}$H$_{29}$N$_5$O$_3$.C$_4$H$_4$O$_4$) C, H, N.

Example 206

(2R)-Methyl-1-[3-(2,5-dimethoxyphenoxyethoxy)-2-pyrazinyl]piperazine, Maleate. Maleate Step 1: 2-(2,5-Dimethoxyphenoxy)-1-ethanol*.

The title compound was prepared according to the procedure of Example 91, Step 1, starting from 2,5-dimethoxyphenol.** Yield 85%; mp 50–52° C. Anal (C$_{10}$H$_{14}$O$_4$) C, H.

*Previously reported in *J. Med. Chem.* 1963, 6, 63–69. However, no experimental details were given.
**Prepared as described in *Synth. Commun.* 1995, 25, 2121–2134.

Step 2: (2R)-Methyl-1-[3-(2,5-dimethoxyphenoxyethoxy)-2-pyrazinyl]piperazine, Maleate.

The title product was prepared according to the procedure of Example 192, Step 3 starting from the product obtained in Step 1 above and (2R)-1-(3-chloro-2-pyrazinyl)-2-methylpiperazine (from Example 192, Step 2). Yield 26%; nip 105–109° C. Anal ($C_{19}H_{26}N_4O_4 \cdot C_4H_4O_4$) C, H, N.

Example 207

3-(1-piperazinyl)-2-pyrazinyl 1,2,3,4-tetrahydro-2-naphthalenylmethyl ether, Fumarate The title product was prepared according to the procedure of Example 90, Step 2, starting from 1,2,3,4-tetrahydro-naphtalenylmethanol* (0.79 g, 4.88 mmol) and 2-chloro-3-(1-piperazinyl)pyrazine (0.99 g, 4.6 mmol; from Example 90, Step 1). Oil; yield 57% of the free base. The free base was converted to the fumarate: mp 186–188° C.; Anal. ($C_{19}H_{24}N_4O \cdot C_4H_4O_4 \cdot 0.25H_2O$) C, H, N.

*Previously described in Aust. J. Chem. 1992, 45, 289–308.

Example 208

3-[(2R)-2-methylpiperazinyl]-2-pyrazinyl)1,2,3,4-tetrahydro-2-naphthalenylmethyl ether, Fumarate The title product was prepared according to the procedure of Example 192, Step 3, starting from 1,2,3,4-tetrahydro-naphtalenylmethanol (0.98 g, 6.04 mmol) and (2R)-1-(3-chloro-2-pyrazinyl)-2-methylpiperazine (1.3 g, 5.7 mmol; from Example 192, Step 2). The product was isolated as a mixture of two diastereomers. Yield of the free base was 63%. The free base was converted to the fumarate salt: mp 169–172° C. Anal ($C_{20}H_{26}N_4O \cdot C_4H_4O_4$) C, H, N.

Example 209

1-{4-[2-(3-Pyridinyloxy)ethoxy]-1,2,5-thiadiazol-3-yl}piperazine, Maleate

Step 1: 3-Chloro-4-(1-piperazinyl)-1,2,5-thiadiazole, Hydrochloride.

A mixture of 3,4-dichloro-1,2,5-thiadiazole (4.00 g, 25.8 mmol) and piperazine hexahydrate (25.0 g, 130 mmol) in DMF (25 mL) was heated at 70° C. for 20 minutes. After cooling to ambient temperature, the reaction mixture was basified (11M NaOH) and brine was added. The resulting mixture was extracted with $CHCl_3$ (×3). The combined organic phases were washed twice with brine/water (1:1), dried ($MgSO_4$) and the solvent was evaporated. The resulting oil was purified by column chromatography on silica gel using $CHCl_3$ as eluent to give 2.77 g (52%) of the title compound as a colourless oil which was converted to its hydrochloride salt: mp 231° C. (dec). Anal. ($C_6H_9ClN_4S \cdot HCl$), calc 29.89, found 30.4. H, N.

Step 2: 1-{4-[2-(3-Pyridinyloxy)ethoxy]-1,2,5-thiadiazol-3-yl}piperazine, Maleate.

The product from Step 1 above (0.70 g, 3.42 mmol), 2-(3-pyridinyloxy)-1-ethanol (0.57 g, 4.10 mmol; from Example 150, Step 1) and sodium hydride (60% in mineral oil, 0.19 g, 4.79 mmol) was stirred at 70° C. in dioxane for 14 h. The reaction mixture was filtered through a pad of silica gel and concentrated. The remaining oil was purified by by C-18 HPLC using $CH_3CN/H_2O$ (gradient: $CH_3CN$ 0% to 100%). This furnished the free base of the title compound as an oil which was converted to the maleate salt: yield 0.16 g (11%); mp 116–118° C. Anal. ($C_{13}H_{17}N_5O_2S \cdot C_4H_4O_4$) C, H, N.

Example 210

2-[2-(2,3-Dihydro-1,4-benzodioxin-6-yloxy)ethoxy]-3-(1-piperazinyl)pyrazine, Dihydrochloride Step 1: 2-(2,3-Dihydro-1,4-benzodioxin-6-yloxy)ethanol.

The title compound was prepared according to the procedure described in Example 91, Step 1 starting from 6-hydroxy-1,4-benzodioxane.* Oil; yield 55%. MS m/z 196 (M)$^+$. HRMS m/z calcd for $C_{10}H_{12}O_4$ (M)$^+$196.0736, found 196.0735.

*Prepared as described in Eur. J. Med. Chem. 1989, 24, 619–22.

Step 2: tert-butyl 4-{3-[2-(2,3-Dihydro-1,4-benzodioxin-6-yloxy)ethoxy]-2-pyrazinyl}-1-piperazinecarboxylate.

To a solution of the product obtained in Step 1 (0.22 g, 1.12 mmol) and 2-chloro-3-(1-piperazinyl)pyrazine (0.25 g, 1.26 mmol; from Example 90, Step 1) in dioxane (5 mL) was added NaH (50% in mineral oil, 0.05 g, 1.1 mmol). The solution was heated at 90° C. overnight. After cooling, EtOAc (10 mL) %%,as added and the solution was washed with water, dried over $Na_2CO_3$ and concentrated. The oily residue (0.51 g) was dissolved in a mixture of EtOAc (2 mL) and $Et_3N$ (1 mL) and $(t-BuOC)_2O$ (0.32 g, 1.5 mmol) was added. The resulting mixture was stirred at room temperature overnight. The reaction mixture was concentrated and the residue was purified by column chromatography on silica gel using MeOH/EtOAc (2:1) as eluent to give 0.43 g (93%) of the title product as an oil. MS m/z: 458 (M) HRMS m/z calcd for $C_{23}H_{30}N_4O_6$ (M)$^+$458.2165, found 458.2178.

Step 3: 2-[2-(2,3-Dihydro-1,4-benzodioxin-6-yloxy)ethoxy]-3-(1-piperazinyl)pyrazine, Dihydrochloride.

To a solution of the product obtained in Step 2 (0.43 g, 0.94 mmol) in $CH_2Cl_2$ (2 mL) was added $CF_3COOH$ (1.5 mL) at room temperature. The solution was stirred at room temperature for 5 h and evaporated to dryness. The residue was dissolved in EtOAc. The solution was washed with 25% aqueous NaOH and dried over $K_2CO_3$. A solution of HCl in $Et_2O$ was dropped into the solution until no more precipitate formed. The precipitate was collected, washed with ethyl ether, and dried in vacuum to give 251 mg (62%) of the title product: mp 158–160° C. MS m/z 358 (M)$^+$. HRMS m/z calcd for $C_{18}H_{22}N_4O_4$ (M)$^+$358.1641, found 358.1647.

Example 211

2-[3-(2-Methoxyphenyl)propoxy]-3-(1-piperazinyl) pyrazine, Maleate

A mixture of 2-chloro-3-(1-piperazinyl)pyrazine (0.40 g, 2.0 mmol; from Example 90 Step 1), 3-(2-methoxyphenyl)-propan-1-ol (0.50 g, 3.0 mmol), and KO-t-Bu (1 M in t-BuOH; 3 mL, 3 mmol) in dry dioxane (30 mL) was stirred at reflux for 20 h. The reaction was quenched by addition of water (2 mL). The solvent was evaporated and the crude mixture was passed through a column of hydromatrix material with $CH_2Cl_2$ as eluent. The elute was concentrated and the remaining oil was purified by silica gel chromatography using EtOAc/MeOH/$Et_3N$ (8:1:1) as eluent. This furnished the free base of the title compound as an oil which was converted to the maleate salt: yield 0.20 g (22%); mp 132–133° C. Anal. ($C_{18}H_{24}N_4O_2 \cdot C_4H_4O_4$) C, H, N.

Example 212

2-{[(2E)-3-(2-Methoxyphenyl)-2-propenyl]oxy}-3-(1-piperazinyl)pyrazine, Maleate

The title compound was prepared according to the procedure of Example 90. Step 2, starting from 2-chloro-3-(1-piperazinyl)pyrazine (0.50 g, 2.5 mmol, from Example 90.

Step 1) and 2-methoxy-cinnamyl alcohol (0.54 g, 3.3 mmol). Yield 0.45 g (41%); mp 136° C. (dec). Anal. ($C_{18}H_{22}N_4O_2 \cdot C_4H_4O_4$) C, H, N.

Example 213

3-(1-Piperazinyl)-2-pyrazinyl 6-quinolinylmethyl ether, Fumarate

The title compound was prepared according to the procedure of Example 90, Step 2, starting from 2-chloro-3-(1-piperazinyl)pyrazine (1.2 g, 5.6 mmol, from Example 90, Step 1) and 6-quinolinemethanol* (0.89 g, 5.6 mmol). Yield 0.80 g (94%); mp 207–209° C. Anal. ($C_{18}H_{19}N_5O \cdot C_4H_4O_4 \cdot 0.25H_2O$)C, H, N.
*Previously described in J. Org. Chem. 1953, 18, 55–58.

Example 214

N,N'-Dimethyl-N-[3-(2-phenoxyethoxy)-2-pyrazinyl]-1,2-ethanediamine

A mixture of 2-chloro-3-(2-phenoxyethoxy)pyrazine (50 mg, 0.20 mmol; from Example 1, Step 1) and N N-dimethylethylenediamine (0.2 mL, 1.9 mmol) was heated in a MicroWell 10 microwave reactor for 6 min at 100 W. The reaction mixture was partitioned between water and EtOAc and applied to a hydromatrix column. The column was eluted with EtOAc and the elute was concentrated. The product was purified by Amberchrom CG-161 m LC using $CH_3CN/H_2O$ (gradient: $CH_3CN$ 0% to 100%). Yield 2 mg (4%). MS m/z 303 $(M+H)^+$.

Example 215

N,N-Dimethyl-2-{[3-(2-phenoxyethoxy)-2-pyrazinyl]sulfanyl}ethanamine

A mixture of 2-chloro-3-(2-phenoxyethoxy)pyrazine (100 mg, 0.40 mmol, from Example 1, Step 1), dimethylamino-ethanethiol hydrochloride (56 mg, 0.40 mmol) and sodium hydride (60% in mineral oil; 32 mg, 0.80 mmol) was stirred at 60° C. for 12 h. The reaction mixture was concentrated and partitioned between water and EtOAc and applied on a hydromatrix column. The column was eluted with EtOAc and the elute vas concentrated. The product was purified by Amberchrom CG-161 m LC using $CH_3CN/H_2O$ (gradient: $CH_3CN$ 0% to 100%). Yield 24 mg(24%). MS m/z 320 $(M+H)^+$.

Example 216

(2R)-Methyl-1-(3-{2-[(1-oxido-3-pyridinyl)oxy]ethoxy}-2-pyrazinyl)piperazine
Step 1: tert-Butyl (3R)-3-methyl-4-{3-[2-(3-pyridinyloxy)ethoxy]-2-pyrazinyl}-1-piperazinecarboxylate.

Di-tert-butyl dicarbonate (1.01 g, 4.64 mmol) in dioxane (50 mL) was added to a solution of the fumararate salt of (2R)-methyl-1-{3-[2-(3-pyridinyloxy)ethoxy]-2-pyrazinyl}piperazine* (2.0 g, 4.64 mmol) in a mixture of dioxane/10% aqueous $NaHCO_3$ (1:1; 1100 mL). The reaction mixture was stirred overnight at room temperature and extracted with EtOAc (3×100 mL). The organic phase was concentrated and the residue purified by column chromatography on silica using isohexane/EtOAc (3:1 to 1:1) as eluent. This furnished 1.48 g (77%) of the title product as an oil. MS m/z 416 $(M+H)^+$. HRMS m/z calcd for $C_{21}H_{29}N_5O_4$ $(M)^{+415.2220}$ found 415.2224.
*The corresponding hydrochloride salt is described in Example 173.

Step 2: tert-Butyl (3R)-methyl-4-(3-{2-[(1-oxido-3-pyridinyl)oxy]ethoxy}-2-pyrazinyl)-1-piperazinecarboxylate.

MCPBA (2.91 g, 16.9 mmol) was added to the solution of the product obtained in Step 1 above (1.4 g, 3.37 mmol) in $CH_2Cl_2$ (50 mL). The reaction mixture was stirred for 1 h at room temperature. This gave a mixture of two unknown di-oxidized derivatives (MS). Aqueous sodium metabisulfite (10%, 50 mL) was added and the reaction mixture was stirred at room temperature until the di-oxidized products had converted to a single mono-oxidized derivative. Extraction with EtOAc (3×50 mL), concentration, and purification of the residue by column chromatography on silica, using isohexane/EtOAc (3:1 to 1:1) as eluent, furnished 0.96 g (66%) of the title product as an oil. MS m/z: 432 $(M+H)^+$. HRMS m/z calcd for $C_{21}H_{29}N_5O_5$ $(M)^+431.2169$, found 431.2171.

Step 3: (2R)-2-methyl-1-(3-{2-[(1-oxido-3-pyridinyl)oxy]ethoxy})-2-pyrazinyl)piperazine.

The product obtained in Step 2 (0.86 g, 2.0 mmol) was treated with $CH_2Cl_2$/TFA (75:25; 10 mL) for 1 h at room temperature. After concentration, the residue was purified by column chromatography on silica using $EtOAc/MeOH/Et_3N$ (80:15:5) as eluent to give 0.32 g (48%) of the title compound as an oil. MS m/332 $(M+H)^+$. HRMS m/calcd for $C_{16}H_{21}N_5O_3$ $(M)^+331.1644$, found 331.1655.

Example 217

2-[(2-Phenoxyethyl)sulfanyl]-3-(1-piperazinyl)pyrazine, Trifluoroacetate
Step 1: tert-Butyl 4-{3-[(2-hydroxyethyl)sulfanyl]-2-pyrazinyl}-1-piperazinecarboxylate.

Sodium hydroxide (0.92 g, 23 mmol) was dissolved in water (9 mL) and dioxane (15 mL). 2-Mercaptoethanol (0.54 mL, 7.7 mmol) was added while stirring and 2-chloro-3-(4-tert-butoxycarbonyl-1-piperazinyl)pyrazine (2.3 g, 7.7 mmol, from Example 52, step 1) in dioxane (10 mL) was added. The reaction mixture was heated at 100° C. for 22 h. After cooling to room temperature, it was extracted with EtOAc. The organic layer was dried ($K_2CO_3$) and the solvent was removed under reduced pressure. The residue was purified by chromatography on silica gel using hexane/EtOAc (1:1) as eluent to give 1.71 g (65%) of the title compound as an orange oil. MS m/z 341 $(M+H)^+$.
Step 2: tert-Butyl 4-{3-[(2-phenoxyethyl)sulfanyl]-2-pyrazinyl}-1-piperazinecarboxylate.

The product obtained in Step 1 (0.135 g, 0.39 mmol), triphenylphosphine (0.134 g, 0.51 mmol) and phenol (48 mg, 0.51 mmol) were dissolved in dry THF (4 mL). Diethyl azodicarboxylate (80 µL, 0.51 mmol) was then added dropwise. The reaction mixture was stirred at room temperature overnight. The solvent was then removed under reduced pressure. The residue was purified by chromatography on silica gel using hexane/EtOAc (1:1) followed by a second column using ($CH_2Cl_2 \rightarrow CH_3OH$). This gave 29 mg (18%) of the title compound as a yellow oil.
Step 3: 2-[(2-Phenoxyethyl)sulfanyl]-3-(1-piperazinyl)pyrazine, Trifluoroacetate.

The product obtained in Step 2 (30 mg, 0.072 mmol) was dissolved in $CH_2Cl_2$ (0.75 mL) and cooled to ~0° C. Trifluoroacetic acid (0.25 mL) was then added and the reaction mixture was stirred for 40 min at 5° C. The solvent was evaporated under vacuum. It gave a beige solid 26 mg of the crude product. Purification by reverse phase preparative HPLC on a SymmetryPrep $C_{18}$ column (150×19 mm, 7 µm), eluting with a gradient of 5% $CH_3CN$ in 95% water to 95% $CH_3CN$ in 5% water (0.2% TFA buffer), of a 13 mg sample gave 6 mg (39%) of the title product as a white solid. MS m/z 317 (M+H)+; HRMS m/z calcd for $C_{16}H_{20}N_4OS$ (M)+316.1358, found 316.1355. Anal. ($C_{16}H_2N_4OS.C_2HF_3O_2.0.5H_2O$)C, H, N.

Example 218

7-(2-{[4-(1-piperazinyl)-1,2,5-thiadiazol-3-yl] oxy}ethoxy)-2H-chromen-2-one

Step 1: tert-Butyl 4-(4-chloro-1,2,5-thiadiazol-3-yl)-1-piperazinecarboxylate.

A mixture of N-Boc-piperazine (2.97 g, 15.9 mmol), $K_2CO_3$ (2.20 g, 15.9 mmol) and 3,4-dichloro-1,2,5-thiadiazole (1.5 mL, 15.9 mmol) in $CH_3CN$ (30 mL) was stirred at 100° C. for 19 h and at room temperature for 4 days. The reaction mixture was then diluted with EtOAc and water. The organic phase was dried ($K_2CO_3$) and the solvent was removed under reduced pressure. The residue was purified by chromatography on two successive silica gel columns eluting with hexane/EtOAc (1:1) and (7:3), respectively. This gave 1.54 g (31%) of the title product as a yellow solid.

Step 2: tert-Butyl 4-[4-(2-hydroxyethoxy)-1,2,5-thiadiazol-3-yl]-1-piperazinecarboxylate.

K-t-BuO (1.24 g, 1 mmol) was added to a mixture of the product obtained in Step 1 (198 g, 6.5 mmol) and ethylene glycol (2.54 ml, 45.5 mmol) in pyridine (15 ml). The reaction mixture was stirred at 100° C. for 6 h and at room temperature overnight. The solution was then poured into ice-water and diluted with EtOAc. The organic phase was dried ($MgSO_4$) and the solvent removed under reduced pressure. The residue %% as purified by chromatography on silica gel eluting hexane/EtOAc (1:1) to give 1.71 g (65%) of title product as an orange oil. MS m/z 331 (M+H)+.

Step 3: tert-Butyl 4-(4-{2-[(2-oxo-2H-chromen-7-yl)oxy]ethoxy}-1,2,5-thiadiazol-3-yl)-1-piperazinecarboxylate.

Diethyl azodicarboxylate (DEAD, 61 µl, 0.39 mmol) was added drop wise to a mixture of the product obtained in Step 2 (100 mg, 0.30 mmol), triphenylphosphine (102 mg, 0.39 mmol) and 7-hydroxycoumarin (63 mg, 0.39 mmol) in dry THF (5 mL). The reaction mixture was stirred at room temperature for 5 days. After solvent removal, the residue was purified by chromatography on silica gel eluting with hexane/EtOAc (1:1) to give the title product as a white solid (176 mg) which had low purity (67% by HPLC). This material was used directly in the following step without further purification.

Step 4: 7-(2-{[4-(1-piperazinyl)-1,2,5-thiadiazol-3-yl] oxy}ethoxy)-2H-chromen-2-one.

The product obtained in Step 3 (176 mg) was diluted in $CH_2Cl_2$ (1.5 mL) and cooled to ~0° C. Trifluoroacetic acid (0.5 mL) was added and the reaction mixture was stirred for 1 h at 5° C. After solvent removal in vacuo, the residue was purified by chromatography on silica gel using hexane/EtOAc (1:1) followed by $CH_2Cl_2$/MeOH/Et$_3$N (90:5:5) as eluents This furnished 45 mg (40%) of the title product as a white solid. MS m/z 375 (M+H)+.

Example 219

Step 1: tert-Butyl 4-{4-[2-(7-isoquinolinyloxy)ethoxy]-1,2,5-thiadiazol-3-yl}-1-piperazinecarboxylate.

The title compound was prepared according to the procedure of Example 218, Step 3 starting from the product of Example 218, Step 2 (100 mg, 0.30 mmol), triphenylphosphine (102 mg, 0.39 mmol), 7-hydroxyisoquinoline (57 mg, 0.39 mmol) and diethyl azodicarboxylate (61 µl, 0.39 mmol) except that the reaction mixture was stirred at room temperature for 5 days. It gave an orange oil (0.34 g) of low purity (63% by HPLC). It was used directly in the following step without further purification.

Step 2: 7-(2-{[4-(1-piperazinyl)-1,2,5-thiadiazol-3-yl] oxy}ethoxy)isoquinoline.

The product obtained in Step 1 (340 mg) %%,as dissolved in $CH_2Cl_2$ (1.5 mL) and cooled to ~0° C. Trifluoroacetic acid (0.5 mL) was added and the reaction mixture was stirred at 5° C. for 1 h. After solvent removal in vacuo, the residue was purified by chromatography on silica gel using hexane/EtOAc (1:1) followed by $CH_2Cl_2/CH_3OH/Et_3,N$ (90:5:5) as eluents. This furnished 59 mg (55%) of the title product as a yellow oil. MS m/z (M+H)+358.

Example 220

2-{2-[3-(2-Fluoroethoxy)phenoxy]ethoxy}-3-(1-piperazinyl)pyrazine, Trifluoroacetate Step 1: tert-Butyl 4-{3-[2-(3-hydroxyphenoxy)ethoxy]-2-pyrazinyl}-1-piperazinecarboxylate.

To a stirred solution of 2-(3-hydroxyphenoxy)ethanol (7.71 g, 0.05 mol) in dry DMF to (100 mL) at ~0° C. (ice bath) was added NaH (3.90 g, 0.163 mol) in portions under $N_2$. When the $H_2$-evolution had ceased, a solution of 2-chloro-3-(4-tert-butoxycarbonyl-1-piperazinyl)pyrazine (0.05 mol, 14.9 g; from Example 52, Step 1) in dry DMF (70 mL) was added in one portion. The mixture was stirred at 65° C. for 1.75 h. After cooling, the reaction was quenched by addition of $H_2O$ in DMF. The mixture was filtered and concentrated, in vacuo. The residue was dissolved in EtOAc, washed with 1 M $KHSO_4$ and water, dried ($Na_2SO_4$+Norit), and concentrated in vacuo to give the title compound as a beige sticky oil. Yield 94%. This product was used directly in the next step without further purification.

Step 2: 2-{2-[3-(2-Fluoroethoxy)phenoxy]ethoxy}-3-(1-piperazinyl)pyrazine, Trifluoroacetate.

The product obtained in Step 1 above (83 mg, 0.20 mmol) was dissolved in $CH_2Cl_2$ (8.0 mL) and treated first with polymer supported triphenylphosphine (3.0 mmol/g) (133 mg, 0.40 mmol), 2-fluoroethanol (26 mg, 0.40 mmol) and then diethyl azodicarboxylate (DEAD; 70 mg, 0.40 mmol). The reaction mixture was shaken at room temperature, for 18 h, then filtered to remove the solid support. The filtrate was concentrated under reduced pressure then diluted with MeOH (1.5 mL) and purified by preparative C-18 HPLC using $CH_3CN/H_2O$/TFA (gradient: $CH_3CN$ 60% to 90%, TFA 0.1%) to give the Boc-protected intermediate. This material was not isolated but treated directly with a solution of 25% TFA in $CH_2Cl_2$ for 30 min then concentrated under reduced pressure to afford 24 mg (25%) of the title compound. MS m/z 363 (M+H)+.

Example 221

2-(2-{3-[2-(4-Methyl-1,3-thiazol-5-yl)ethoxy] phenoxy}ethoxy)-3-(1-piperazinyl)pyrazine, Trifluoroacetate The title compound was prepared according to the procedure of Example 220, Step 2, starting from 4-methyl-5-thiazolylethanol (57 mg, 0.40 mmol) and the product obtained in Example 220, Step 1, (83 mg, 0.20 mmol) to give 57 mg (51%) of the title compound. MS m/z 442 (M+H)+.

Example 222

2-{2-[3-(Cyclopropylmethoxy)phenoxy]ethoxy}-3-(1-piperazinyl)pyrazine, Trifluoroacetate The title compound was prepared according to the procedure of Example 220, Step 2, starting from cyclopropyl-methanol (29 mg, 0.40 mmol) and the product obtained in Example 220, Step 1, (83 mg, 0.20 mmol) to give 30 mg (31%) of the title compound. MS m/z 371 (M+H)+.

Example 223

2-{2-[3-(3-Butenyloxy)phenoxy]ethoxy}-3-(1-piperazinyl)pyrazine, Trifluoroacetate The title compound was prepared according to the procedure of Example 220, Step 2, starting from 3-buten-1-ol (29 mg, 0.40 mmol) and the product obtained in Example 220, Step 1 (83 mg, 0.20 mmol) to give 57 mg (59%) of the title compound. MS m/z 371 (M+H)+.

Example 224

N,N-Dimethyl-N-{2-[3-(2-{[3-(1-piperazinyl)-2-pyrazinyl]oxy}ethoxy)phenoxy]-ethyl}amine, Trifluoroacetate The title compound was prepared according to the procedure of Example 220: Step 2, starting from 2-dimethylaminoethanol (36 mg, 0.40 mmol) and the product obtained in Example 220, Step 1 (83 mg, 0.20 mmol) to give 37 mg (37%) of the title product. MS (ES+) m/z 388 (M+H)+.

Example 225

2-(1-Piperazinyl)-3-{2-[3-(tetrahydro-2H-pyran-4-yloxy)phenoxy]ethoxy}pyrazine, Trifluoroacetate A solution of the product obtained in Example 220. Step 1 (208 mg, 0.50 mmol) in $CH_2Cl_2$ (8.0 mL) was treated first with polymer supported triphenylphosphine (3.0 mmol/g) (200 mg, 0.60 mmol), tetrahydro-4H-pyran-4-ol (51 mg, 0.50 mmol) and then diethyl azodicarboxylate (87 mg, 0.50 mmol). The reaction mixture was shaken at room temperature for 18 h, then filtered to remove the solid support. The filtrate was concentrated under reduced pressure and the residue was purified by chromatography on silica gel. Elution with $CH_2Cl_2/Et_2O$ (10:1) gave the crude N-Boc-protected intermediate which was further purified by preparative C-18 HPLC using $CH_3CN/H_2O$/TFA (gradient: $CH_3CN$ 60% to 90%, TFA 0.1%). This material was not isolated but treated directly with a solution of 25% TFA in $CH_2Cl_2$ for 30 min then concentrated under reduced pressure to afford the title compound 19.0 mg (7%), MS m/z 401 (M+H)+.

Example 226

2-{2-[3-(2-Methoxyethoxy)phenoxy]ethoxy}-3-(1-piperazinyl)pyrazine

Step 1: tert-Butyl 4-(3-{2-[3-(2-methoxyethoxy)phenoxy]ethoxy}-2-pyrazinyl)-1-piperazinecarboxylate.

NaH (80% dispersion in mineral oil; 66 mg, 2.75 mmol) was added to a stirred solution of the product obtained in Example 220, Step 1 (716 mg, 1.84 mmol) in dry DMF (10 mL). When the $H_2$-evolution had ceased, 2-bromoethyl methyl ether (256 mg, 1.84 mmol) was added, and the mixture was stirred at 60° C. for 2.5 h. The reaction was quenched by addition of a mixture of HOAc (0.065 mL) and DMF (0.5 mL) followed by a mixture of water (0.065 mL) and DMF (0.50 mL). The resulting mixture was filtered, concentrated in vacuo, and the residue was dissolved in toluene. The solution was washed with 1 M aqueous $KHSO_4$: dried ($Na_2SO_4$) and concentrated in vacuo to give 0.60 g (69%) of the title compound as an oil which %% as used in the next step without further purification.

Step) 2: 2-{2-[3-(2-Methoxyethoxy)phenoxy]ethoxy-}-3-(1-piperazinyl)pyrazine.

The product obtained in Step 1 above was dissolved in a mixture of EtOAc (18 mL) and ether (9 mL) and 5 M HCl/ether (9 mL) was added. The mixture was stirred at room temperature for 3 h. The precipitated hydrochloride salt was filtered off and washed thoroughly with ether. The hydrochloride was dissolved in $EtOAc/MeOH/Et_3N$ (100:40:5) and purified by column chromatography) on silica using $NH_3$-satd. $EtOAc/CH_3OH$ (100:15) as eluent. The combined pure fractions were concentrated in vacuo and the resulting oil was dried (~0.8 torr, room temperature) to give 0.36 g (69%) of the title product. HRMS m/z calcd for $C_{19}H_{26}N_4O_4$ (M)+374.1954, found 374.1947.

Example 227

1-{2-[3-(2-{[3-(1-piperazinyl)-2-pyrazinyl]oxy}ethoxy)phenoxy]ethyl}-2-pyrrolidinone Diethyl azodicarboxylate (DEAD; 575 mg, 3.30 mmol), dissolved in dry THF (5 mL), was added to a stirred mixture of the compound obtained in Example 220, Step 1 (983 mg, 2.36 mmol), 1-(2-hydroxyethyl)-2-pyrrolidinone (427 mg, 3.30 mmol) and $Ph_3P$ (867 mg, 3.30 mmol) in dry THF (50 mL). The reaction mixture was stirred at room temperature overnight and the solvent was evaporated. The residue was treated with EtOAc/hexane (1:1) and solids were filtered off. The filtrate was washed with 0.5 M aqueous $Na_2CO_3$, dried ($Na_2SO_4$), and concentrated in vacuo. The residue was purified by column chromatography on silica to give 1.1 g (88%) of the r-Boc protected intermediate. This material was directly N-Boc deprotected as described in Example 220, Step 2, to give 0.50 g (50% over two steps) of the title product as an oil. HRMS m/z calcd for $C_{22}H_{29}N_5O_4$ (M)+ 427.2220, found 427.2227.

Example 228

2-(1-Piperazinyl)-3-{(2-[3-(tetrahydro-3-furanyloxy)phenoxy]ethoxy}pyrazine

The title compound was prepared according to the procedure of Example 227 starting from the product of Example 220, Step 1, and 3-hydroxytetrahydrofuran. Yield 29% over two steps. HRMS m/z calcd for $C_{20}H_{26}N_4O_4$ (M)+386.1954, found 386.1963.

Example 229

2-(1-piperazinyl)-3-{2-[3-(tetrahydro-3-furanylmethoxy) phenoxy]ethoxy},pyrazine The title compound was prepared according to the procedure of Example 227 starting from the product of Example 220, Step 1, and tetrahydro-3-furanmethanol. Yield 48% over two steps. HRMS m/z calcd for $C_{21}H_{28}N_4O_4$(M)+ 400.2111, found 400.2098.

Example 230

2-{[3-(2-{[3-(1-Piperazinyl)-2-pyrazinyl]oxy}ethoxy)phenoxy]methyl}benzonitrile, Trifluoroacetate A suspension of the product obtained in Example 220, Step 1 (62 mg, 0.15 mmol), 2-cyanobenzyl bromide (20 mg, 0.10 mmol) and polymer supported triazabicyclodecene (PTBD) (400 mg) in MeCN (8 mL) was shaken at room temperature for 48 h. The mixture was filtered and the filtrate concentrated under reduced pressure to give the crude N-Boc protected intermediate which still contained some unreacted phenol (by HPLC). This material was dissolved in MeCN (8 mL) then retreated with PTBD (300 mg) and shaken at room temperature overnight. The mixture was filtered and the filtrate was concentrated under reduced pressure. The residue was then treated directly with a solution of 25% TFA in $CH_2Cl_2$ for 30 min at room temperature. The reaction mixture was concentrated under reduced pressure to afford 32 mg (59%) of the title compound. MS m/z 432 $(M+H)^+$.

Example 231

2-{2-[3-(Benzyloxy)phenoxy]ethoxy}-3-(1-piperazinyl)pyrazine, Trifluoroacetate

The title compound was prepared according to the procedure of Example 230 starting from the product obtained in Example 220, Step 1 (62 mg, 0.15 mmol), and benzyl bromide (17 mg, 0.10 mmol) to give 14 mg (27%) of the title compound. MS m/z 407 $(M+H)^{30}$.

Example 232

2-(1-Piperazinyl)-3-(2-{3-[2-(2-pyridinyl) ethoxy]phenoxy}ethoxy)pyrazine, Trifluoroacetate A solution of the product obtained in Example 220. Step 1 (208 mg, 0.50 mmol) in $CH_2Cl_2$ (8 mL) was treated first with polymer supported triphenylphosphine (3.0 mmol/g) (200 mg; 0.60 mmol), 2-(2-hydroxyethyl)pyridine (62 mg, 0.50 mmol) and then diethyl azodicarboxylate (87 mg, 0.50 mmol). The reaction mixture was shaken at room temperature for 3 h, then filtered to remove the solid support. The filtrate was concentrated under reduced pressure and the residue was purified by chromatography on silica gel. Elution with diethyl ether gave the crude N-Boc-protected intermediate which was treated directly with a solution of 25% TFA in $CH_2Cl_2$ for 30 min at room temperature. The reaction mixture was concentrated under reduced pressure to afford 54 mg (20%) of the title compound. MS m/z 422 $(M+H)^+$.

Example 233

2-[(4-Methoxybenzyl)oxy]-3-(1-piperazinyl)pyrazine

The title compound was prepared according to the procedure of Example 90, Step 2, starting from 2-chloro-3-(1-piperazinyl)pyrazine (0.80 g, 4.0 mmol; from Example 90, Step 1) and 4-methoxybenzyl alcohol (0.88 g, 6.4 mmol). Oil; yield 72%. MS m/z 301 $(M+H)^+$.

Example 234

2-(1-Methyl-2-phenylethoxy)-3-(1-piperazinyl)pyrazine, Trifluoroacetate

The title compound was prepared according to the procedure of Example 90, Step 2, starting from 2-chloro-3-(1-piperazinyl)pyrazine (0.15 g, 0.75 mmol; from Example 90, Step 1) and 1-phenyl-2-propanol (163 mg, 1.2 mmol). MS m/z 299 $(M+H)^+$. The crude product was purified by reverse phase preparative HPLC on a SymmetryPrep $C_{18}$ column (150×19 mm, 7 µm), eluting with a gradient of 5% $CH_3CN$ in 95% water to 95% $CH_3CN$ in 5% water (0.2% TFA buffer) to give gave 55 mg (18%) of the title product as a white solid. MS m/z 299 $(M+H)^+$.

Example 235

2-[2-(1-Naphthyl)ethoxy]-3-(1-piperazinyl)pyrazine, Trifluoroacetate

The title compound was prepared according to the procedure of Example 90. Step 2, starting from 2-chloro-3-(1-piperazinyl)pyrazine (0.50 g, 2.5 mmol; from Example 90, Step 1) and 1 naphthaleneethanol (0.69 g, 4.0 mmol). The crude product was purified by reverse phase preparative HPLC on a SymmetryPrep $C_{18}$column (150×19 mm, 7 µm), eluting with a gradient of 5% $CH_3CN$ in 95% water to 95% $CH_3CN$ in 5% water (0.2% TFA buffer) to give gave 290 mg (26%) of the title product as a white solid. MS m/z 335 $(M+H)^+$. Anal. $(C_{20}H_{22}N_4O.C_2HF_3O_2)$ C, H, N.

Preparation of Pharmaceutical Compositions

EXAMPLE: Preparation of Tablets

| Ingredients | mg/tablet |
|---|---|
| 1. Active compound | 10.0 |
| 2. Cellulose, microcrystalline | 57.0 |
| 3. Calcium hydrogen phosphate | 15.0 |
| 4. Sodium starch glycolate | 5.0 |
| 5. Silicon dioxide, colloidal | 0.25 |
| 6. Magnesium stearate | 0.75 |

The active ingredient 1 is mixed with ingredients 2, 3, 4 and 5 for about 10 minutes. The magnesium stearate is then added, and the resultant mixture is mixed for about 5 minutes and compressed into tablet form with or without film-coating.

Pharmacological Tests

The ability of a compound of the invention to bind or act at specific 5-HT receptor subtypes can be determined using in vitro and in vivo assays known in the art. The biological activity of compounds prepared in the Examples was tested using different tests.

Affinity Assay

The 5-$HT_{2c}$ receptor affinity of compounds in the Examples was determined in competition experiments, where the ability of each compound in serial dilution to displace $^3$H-labelled 5-HT, bound to membranes prepared from a transfected HEK293 cell line stably expressing the human 5-$HT_{2c}$ receptor protein was monitored by Scintillation Proximity Assay technology. Non-specific binding was defined using 5 µM mianserin. Results obtained for exemplary compounds of the invention are illustrated in Table 1 below. Typically, the 5$HT_{2c}$ receptor affinity values ($K_i$, nM) were in the range of 1 nM to 1500 nM.

TABLE 1

| Compound | Ki (nM) |
|---|---|
| Example 23 | 377 |
| Example 57 | 24 |
| Example 82 | 116 |
| Example 125 | 171 |
| Example 122 | 45 |
| Example 150 | 50 |
| Example 151 | 185 |

TABLE 1-continued

| Compound | Ki (nM) |
|---|---|
| Example 167 | 34 |
| Example 173 | 16 |
| Example 183 | 10 |
| Example 194 | 5 |
| Example 231 | 12 |

Efficacy Assay

The agonist efficacy at the 5-$HT_{2c}$ receptor of the compounds in the Examples was determined by the ability of each compound to mobilise intracellular calcium in transfected HEK293 cells, stably expressing the human 5-$HT_{2c}$ receptor protein, using the calcium-chelating fluorescent dye FLUO-3 (Sigma. St. Louis, Mo. U.S.A.).

Typically, the maximum responses of 5-$HT_{2c}$ agonists were in the range of 20–100% relative to the maximum response of 5-HT (serotonin) at a concentration of 1 μM.

Toxicity Tests

Acute toxicity studies in mice following oral administration of a number of compounds in the Examples showed that mortality typically occurred at doses between about 200 mg/kg body weight to about 450 mg/kg body weight.

What is claimed is:

1. A compound of the general formula (I):

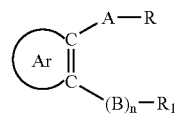

(I)

wherein

Ar is aryl or heteroaryl which may be independently substituted in one or more positions by $C_{1-6}$-alkyl, $C_{1-6}$-alkoxy, $C_{1-6}$-alkylthio, $C_{1-6}$-acyl, $C_{1-6}$-alkylsulphonyl, cyano, nitro, hydroxy, $C_{2-6}$-alkenyl, $C_{2-6}$-alkynyl, fluoromethyl, difluoromethyl, trifluoromethyl, difluoromethoxy, trifluoromethoxy, difluoromethylthio, trifluoromethylthio, halogen, —$N(R_2)(R_3)$, aryl, alkoxy, arylthio, aryl-$C_{1-4}$-alkyl, aryl-$C_{2-4}$-alkenyl, aryl-$C_{2-4}$-alkynyl, heterocyclyl, heterocyclyloxy, heterocyclylthio or heterocyclyl-$C_{1-4}$-alkyl, wherein any aryl and heterocyclyl residues as substituents or part of substituents on aryl or heteroaryl in turn may be substituted in one or more positions independently of each other by halogen, $C_{1-6}$-alkyl, $C_{1-6}$-alkoxy, $C_{1-6}$-alkylthio, $C_{1-6}$-acyl, $C_{1-6}$-alkylsulphonyl, nitro, trifluoromethyl, trifluoromethylthio, cyano, hydroxy, amino, $C_{1-6}$-alkylamino, di($C_{1-6}$-alkyl)amino or $C_{1-6}$-acylamino;

A is (i) —O—, —S—, —$SO_2$— or —NH—; (ii) a $C_{1-4}$-alkyl-substituted nitrogen atom, or (iii) a $C_{1-8}$-alkylene chain or a heteroalkylene chain having 2 to 8 chain atoms, which optionally contains one or more unsaturations, wherein $C_{1-8}$-alkylene and heteroalkylene may be independently substituted in one or more positions by $C_{1-4}$-alkyl or oxo, and wherein two juxtaposed or spaced chain atoms in $C_{1-8}$-alkylene or heteroalkylene optionally are joined through an alkylene bridge having 1 to 5 chain carbon atoms or a heteroalkylene bridge having 2 to 5 chain atoms, or two spaced chain atoms in $C_{1-8}$-alkylene or heteroalkylene optionally are joined through a bridging bond, to form a saturated or partially or fully unsaturated carbocyclic or heterocyclic ring having 3 to 8 ring members;

B is —$C(R_4)(R_5)$—, —$OC(R_4)(R_5)$—, —$N(R_6)C(R_4)(R_5)$—, —$N(R_6)$—, —O—, —S— or —$SO_2$—;

R is $C_{3-8}$-cycloalkyl, aryl or heteroaryl, each of which may be substituted in one or more positions independently of each other by $C_{1-6}$-alkyl, $C_{1-6}$-alkoxy, fluoro-$C_{1-6}$-alkoxy, 2,2,2-trifluoroethoxy, $C_{3-5}$-alkynyloxy, $C_{3-5}$-alkenyloxy, dimethylamino-$C_{1-6}$-alkoxy, methylamino-$C_{1-6}$-alkoxy, $C_{1-6}$-alkylthio, fluoromethyl, difluoromethyl, trifluoromethyl, fluoromethylthio, difluoromethoxy, difluoromethylthio, trifluoromethoxy, trifluoromethylthio, halogen, hydroxy, nitro, cyano, trifluoromethylsulphonyloxy, $C_{1-6}$-alkylsulphonamido, $C_{2-6}$-alkenyl, $C_{2-6}$-alkynyl, $C_{1-6}$-acyl, $C_{1-6}$-alkylcarbonyl-$C_{1-6}$-alkyl, $C_{1-6}$-alkylsulphonyl, $C_{1-6}$-alkylsulphonyloxy, $C_{1-6}$-alkoxy-$C_{1-6}$-alkyl, $C_{1-6}$-alkoxycarbonyl, $C_{1-6}$-alkoxycarbonyl-$C_{1-6}$-alkyl, $C_{1-6}$-acyloxy-$C_{1-6}$-alkyl, hydroxy-$C_{1-6}$-alkyl, hydroxy-$C_{1-6}$-alkoxy, $C_{1-6}$-alkoxy-$C_{1-6}$-alkoxy, $C_{1-6}$-alkoxy-$C_{1-6}$-alkylthio, hydroxy-$C_{1-6}$-alkylthio, heteroaryl-$C_{1-6}$-alkylthio, aryl-$C_{1-6}$-alkylthio, $C_{1-6}$-alkoxy-$C_{1-6}$-alkylamino, N—($C_{1-6}$-alkoxy-$C_{1-6}$-alkyl)-N-methylamino, $C_{3-6}$-cycloalkyl-$C_{1-6}$-alkoxy, aryl-$C_{1-6}$-alkoxy, heterocyclyl-$C_{1-6}$-alkoxy, $C_{3-8}$-cycloalkyl, $C_{3-8}$-cycloalkyloxy, aryl, aryloxy, arylthio, arylsulphonyl, aryl-$C_{1-6}$-acyl, aryl-$C_{1-6}$-alkyl, aryl-$C_{2-6}$-alkenyl, aryl-$C_{2-6}$-alkynyl, heterocyclyl-$C_{1-6}$-alkyl, heterocyclyl-$C_{2-6}$-alkenyl, heterocyclyl-$C_{2-6}$-alkynyl, heterocyclyl, heterocyclyloxy, heterocyclylthio, heterocyclylsulphonyl, heterocyclylamino, heterocyclyl-$C_{-1-6}$-acyl, —$N(R_2)(R_3)$, —$CON(R_7)(R_8)$ or, when R is optionally substituted $C_{3-8}$-cycloalkyl, oxo, wherein any cycloalkyl, aryl and heterocyclyl residues as substituents on $C_{3-8}$-cycloalkyl, aryl or heteroaryl or as part of substituents on $C_{3-8}$-cycloalkyl, aryl or heteroaryl in turn may be substituted in one or more positions independently of each other by $C_{1-4}$-alkyl, $C_{1-4}$-alkoxy, methanesulphonamido, $C_{1-4}$-alkylthio, $C_{1-4}$-alkylsulphonyl, $C_{1-4}$-acyl, heterocyclyl, heterocyclyloxy, heterocyclylthio, aryloxy, arylthio, fluoromethyl, trifluoromethyl, trifluoromethoxy, trifluoromethylthio, halogen, hydroxy, nitro, cyano, $N(R_2)(R_3)$ or, for $C_{3-8}$-cycloalkyl and partially or fully saturated heterocyclyl, oxo or hydroxy;

$R_1$ is (i) a saturated or unsaturated azacyclic or aminoazacyclic ring, or a saturated diazacyclic or aminodiazacyclic ring, which has 4 to 7 ring members, or a saturated aminoazabicyclic, azabicyclic or diazabicyclic ring which has 7 to 10 ring members, which mono- or bicyclic rings may be mono- or disubstituted in one or more positions independently of each other by, preferably bound to a carbon atom, $C_{1-4}$-alkyl, $C_{1-6}$-alkoxy, fluoromethyl, trifluoromethyl, difluoromethyl, oxo, hydroxymethyl or methoxymethyl or —$N(R_6)_2$, or, preferably bound to a ring nitrogen atom, hydroxy, 2-hydroxyethyl or 2-cyanoethyl, or, bound to a ring nitrogen atom, $C_{1-6}$-acyl, $C_{1-4}$-alkoxycarbonyl or tetrahydropyran-2-yl, and wherein a saturated azacyclic ring may contain a further heteroatom selected from oxygen and sulphur; or (ii) a group —$[C(R_4)(R_5)]_xN(R_{2a})(R_{3a})$;

$R_2$ and $R_3$ independently of each other are hydrogen, $C_{1-6}$-alkyl, $C_{1-6}$-acyl, —$CON(R_7)(R_8)$, aryl, heterocyclyl, aryl-$C_{1-6}$-alkyl, heterocyclyl-$C_{1-6}$-alkyl, aryl-$C_{1-6}$-acyl or heterocyclyl-$C_{1-6}$-acyl, wherein any aryl and heterocyclyl residues in turn may be substituted in one or more positions independently of each other by halogen, $C_{1-4}$-alkyl, $C_{1-4}$-alkoxy, $C_{1-4}$-alkylthio, $C_{1-4}$-alkylsulphonyl, methanesulphonamido, nitro, cyano, hydroxy, trifluoromethyl, trifluoromethoxy, trifluoromethylthio or —N($R_2$)($R_3$); or $R_2$ and $R_3$ together with the nitrogen atom to which they are bound form a saturated heterocyclic ring having 4–7 ring members and optionally containing a further heteroatom, which ring may be substituted by $C_{1-6}$-alkyl, $C_{1-6}$-alkoxy, oxo or hydroxy;

$R_{2a}$ and $R_{3a}$ independently of each other are hydrogen, methyl or ethyl, or $R_{2a}$ and $R_{3a}$ together with the nitrogen atom to which they are bound form a pyrrolidine, piperazine or morpholine ring;

$R_4$ and $R_5$ independently of each other, and independently on each substituted carbon atom, are hydrogen or $C_{1-6}$-alkyl;

$R_6$ is hydrogen or $C_{1-6}$-alkyl;

$R_7$ and $R_8$ independently of each other are hydrogen, $C_{1-6}$-alkyl, aryl, heteroaryl, aryl-$C_{1-4}$-alkyl or heteroaryl-$C_{1-4}$-alkyl, wherein aryl and heteroaryl residues in turn may be substituted in one or more positions independently of each other by halogen, $C_{1-6}$-alkyl, $C_{1-6}$-alkoxy, $C_{1-6}$-alkylthio, $C_{1-6}$-alkylsulphonyl, methanesulphonamido, nitro, cyano, hydroxy, trifluoromethyl, trifluoromethoxy, trifluoromethylthio or —N($R_2$)($R_3$); or $R_7$ and $R_8$ together with the nitrogen atom to which they are bound form a saturated heterocyclic ring having 4–7 ring members and optionally containing a further heteroatom;

n is 0 or 1; and x is 2, 3 or 4;

with the proviso that (i) when —A—R is phenoxy or phenylthio, then Ar is other than quinoxalinyl or pyridyl, and (ii) when A is ethenylene, then Ar is other than quinoxalinyl;

and pharmaceutically acceptable salts, hydrates, geometrical isomers, tautomers, optical isomers, N-oxides and prodrug forms thereof.

2. The compound according to claim 1, with the further proviso that when Ar is optionally substituted phenyl or pyridyl, then A is a group -Het—CH($R_6$)—CH($R_6$)—Het-, where each Het independently is selected from O, S and N($R_6$), and $R_6$ is as defined in claim 1.

3. The compound according to claim 1, wherein A is a $C_{2-8}$-alkylene chain or a heteroalkylene chain having at least two chain atoms.

4. The compound according to claim 1, wherein A is a group of the general formula (II):

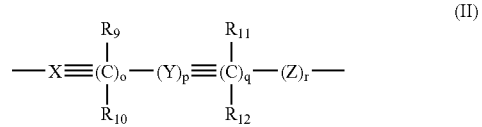

wherein $R_9$, $R_{10}$, $R_{11}$ and $R_{12}$ independently of each other, and independently for each substituted carbon atom, are hydrogen, $C_{1-4}$-alkyl (preferably methyl), trifluoromethyl or oxo;

X is —C($R_{13}$)($R_{14}$, —O—, —S—, —SO$_2$— or —N($R_{15}$)—;

Y is independently —C($R_{16}$)($R_{17}$)—, —O—, —S—, —SO$_2$— or —N($R_{15}$)—;

Z is independently —C($R_{18}$)($R_{19}$)—, —O—, —S—, —SO$_2$— or —N($R_{15}$)—;

$R_{13}$, $R_{14}$, $R_{16}$, $R_{17}$, $R_{18}$ and $R_{19}$, independently of each other, and independently for each substituted carbon atom, are hydrogen, $C_{1-4}$-alkyl or trifluoromethyl or oxo; or two of $R_{13}$, $R_{14}$, $R_{16}$, $R_{17}$, $R_{18}$ and $R_{19}$ together represent an interconnecting bond or an alkylene bridge of 1 to 5 chain carbon atoms or a heteroalkylene bridge of 2 to 5 chain atoms to form, together with the atom(s) to which they are bound, a cyclic structure having 3–8 ring members;

$R_{15}$ is hydrogen, $C_{1-4}$-alkyl or $C_{1-6}$-acyl;

o, p, q and r independently of each other are 0 to 3; and the four broken lines independently of each other represent an optional carbon—carbon bond;

with the provisos (i) that A does not contain two juxtaposed heteroatoms O or S in an open chain, and (ii) that o, p, q and r together are not more than 8.

5. The compound according to claim 4, wherein A is a group -Het—CH($R_6$)—CH($R_6$)—Het-, where each Het independently is selected from O, S and N($R_6$), and $R_6$ is as defined in claim 1.

6. The compound according to claim 5, wherein $R_6$ is hydrogen or methyl, preferably hydrogen.

7. The compound according to claim 5, wherein A is selected from the groups —O—CH$_2$—CH$_2$—O—, —S—CH$_2$—CH$_2$—O—, —O—CH$_2$—CH$_2$—S—, and —O—CH$_2$—CH$_2$—CH$_2$—, preferably —O—CH$_2$—CH$_2$—O.

8. The compound according to claim 7, wherein A is —O—CH$_2$— and R is optionally substituted heteroaryl, e.g. 2,3-dihydro-1,4-benzodioxine, 3,4-dihydro-2H-1,4-benzoxazine, or 2,3-dihydro-1,4-benzoxathiine, quinoline, benzofuran, 3,4-dihydro-2H-pyrido(3,2-b)-1,4-oxazine.

9. The compound according to claim 1 wherein R is optionally substituted aryl or heteroaryl.

10. The compound according to claim 9, wherein R is an optionally substituted phenyl, pyridine, isoquinoline, quinoline, quinoxaline, 2,3-dihydro-1,4-benzodioxine, benzoxazole, 2,1,3-benzothiadiazole, coumarin, 3,4-dihydro-2H-1,4-benzoxazine or quinazoline, preferably a substituted (especially meta-substituted) phenyl ring, or an unsubstituted or substituted pyridine ring.

11. The compound according to claim 1, wherein Ar is optionally substituted pyrazine or phenyl.

12. The compound according to claim 1, wherein Ar is unsubstituted or mono- or di-substituted.

13. The compound according to claim 1, wherein Ar is unsubstituted or mono- or independently di-substituted by $C_{1-4}$-alkyl, $C_{1-4}$-alkoxy, $C_{1-4}$-alkylthio, $C_{1-4}$-alkylsulphonyl, cyano, hydroxy, $C_{2-4}$-alkenyl, $C_{2-4}$-alkynyl, trifluoromethyl, trifluoromethylthio, halogen, amino, methylamino, dimethylamino, acetamido, aryl, aryloxy, arylthio, heterocyclyl, heterocyclyloxy, heterocyclylthio, wherein any aryl and heterocyclyl residues in turn may be substituted in one or more positions independently of each other by halogen, methyl, methoxy, methylthio, methylsulphonyl, nitro, trifluoromethyl, cyano, hydroxy, amino, methylamino and dimethylamino or acetamido.

14. The compound according to claim 1, wherein B is —N($R_6$)—, —O—, —S— or —SO$_2$—, where $R_6$ is as defined in claim 1.

15. The compound according to claim 1 which has the general formula (Ia):

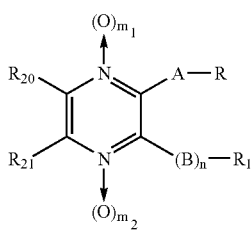

(Ia)

wherein:
R$_{20}$ and R$_{21}$ independently of each other are hydrogen, C$_{1-4}$-alkyl, C$_{1-4}$-alkoxy, C$_{1-4}$-alkylthio, C$_{1-4}$-acyl, C$_{1-4}$-alkylsulphonyl, cyano, nitro, hydroxy, C$_{2-4}$-alkenyl, C$_{2-4}$-alkynyl, trifluoromethyl, trifluoromethoxy, trifluoromethylthio, halogen, amino, dimethylamino, methylamino, acetamido, aryl, aryloxy, arylthio, heterocyclyl, heterocyclyloxy or heterocyclylthio, wherein any aryl and heterocyclyl residues in turn may be substituted in one or more positions independently of each other by halogen, methyl, methoxy, methylthio, methylsulphonyl, nitro, cyano, hydroxy, trifluoromethyl, amino, methylamino, dimethyl amino or acetamido; or R$_{20}$ and R$_{21}$ together with the carbon atoms to which they are bound form a 5— or 6-membered aromatic or heteroaromatic ring, which optionally is independently substituted in one or more positions by halogen, methyl, methoxy, methylthio, methylsulphonyl, nitro, cyano, hydroxy, trifluoromethyl, trifluoromethylthio, amino, methylamino, dimethylamino or acetamido;

m$_1$ and m$_2$ are independently of each other 0 or 1; and
A, B, R, R$_1$ and n are as defined in claim 1.

16. The compound according to claim 15, wherein A is as defined in claim 4, preferably as defined in claim 5, and more preferably as defined in claim 6, especially as defined in claim 7.

17. The compound according to claim 15, wherein n is 0, or n is 1 and B is —N(R$_6$)—, —O—, —S— or —SO$_2$—, where R$_6$ is as defined in claim 1.

18. The compound according to claim 15, wherein R$_{20}$ and R$_{21}$ independently of each other are hydrogen, C$_{1-4}$-alkyl (preferably methyl), C$_{1-4}$-alkoxy (preferably methoxy), C$_{1-4}$-alkylthio (preferably methylthio), halogen, amino, methylamino, dimethylamino, acetamido, phenyl, phenoxy or phenylthio, wherein phenyl, phenoxy and phenylthio optionally may be substituted in one or more positions (preferably mono- or disubstituted) independently of each other by halogen, methyl, methoxy, methylthio, cyano, hydroxy or trifluoromethyl, or R$_{20}$ and R$_{21}$ together with the carbon atoms to which they are bound form a 5- or 6-membered aromatic or heteroaromatic ring, which optionally is independently substituted in one or more positions by halogen, methyl, methoxy, methylthio, methylsulphonyl, nitro, cyano, hydroxy, trifluoromethyl, trifluoromethylthio, amino, methylamino, dimethylamino or acetamido.

19. The compound according to claim 18, wherein R$_{20}$ and R$_{21}$ independently of each other are hydrogen, halogen or C$_{1-4}$-alkyl.

20. The compound according to claim 15, wherein R$_{20}$ and R$_{21}$ form a ring together with the ring carbons to which they are bound.

21. The compound according to claim 20, wherein R$_{20}$ and R$_{21}$ together with the carbon atoms to which they are bound form thiophene to form a thieno pyrazine ring, optionally mono- or di-substituted by halogen.

22. The compound according to claim 15, wherein m is 0.
23. The compound according to claim 1, wherein R$_1$ is piperazine, optionally substituted (preferably at a carbon atom, especially in 2-position) by C$_{1-4}$-alkyl, fluoromethyl, trifluoromethyl, hydroxymethyl or C$_{1-4}$-alkoxymethyl, preferably C$_{1-4}$-alkyl.
24. The compound according to claim 1, wherein n is 0.
25. The compound according to claim 4, wherein o is 2.
26. The compound according to claim 4, wherein p is 1.
27. The compound according to claim 4, wherein q is 0.
28. The compound according to claim 4, wherein r is 0.
29. The compound according to claim 4, wherein at least one of X, Y and Z is oxygen.
30. The compound according to claim 4, wherein R$_9$ to R$_{12}$ are hydrogen.
31. The compound according to claim 1 which has the general formula (Ib):

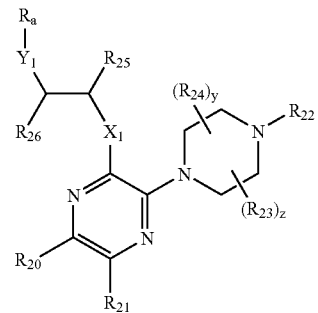

(Ib)

wherein:
X$_1$ and Y$_1$ independently are —O—, —S— or —N(R$_{27}$)—;
R$_a$ is aryl or heteroaryl optionally substituted as defined for R in claim 1;
R$_{20}$ and R$_{21}$ are as defined in claim 11;
R$_{22}$ is hydrogen, hydroxy, C$_{1-4}$-alkyl, C$_{3-4}$-alkenyl, C$_{1-4}$-acyl, C$_{1-4}$-alkoxycarbonyl, 2-hydroxyethyl, 2-cyanoethyl or tetrahydropyran-2-yl;
R$_{23}$ and R$_{24}$ independently of each other are hydrogen, C$_{1-4}$-alkyl, hydroxymethyl, C$_{1-4}$-alkoxymethyl or fluoromethyl;
R$_{25}$ is hydrogen or C$_{1-4}$-alkyl;
R$_{26}$ is hydrogen, C$_{1-4}$-alkyl or is linked to a carbon atom in R$_a$ adjacent to the atom binding to Y$_1$ to form a 5- or 6-membered ring which may contain an additional heteroatom;
R$_{27}$ is hydrogen or C$_{1-4}$-alkyl, preferably methyl or ethyl; and
y and z independently of each other are 1 or 2.
32. The compound according to claim 31, where in R$_{20}$ and R$_{21}$ are as defined in claim 18.
33. The compound according to claim 31, wherein X$_1$ and Y$_1$ both are —O—.
34. The compound according to claim 31 wherein X$_1$ is —S— and Y$_1$ is —O—.
35. The compound according to claim 31, wherein X$_1$ is —O— and Y$_1$ is —S—.
36. The compound according to claim 31, wherein X$_1$ and Y$_1$ both are —S—.
37. The compound according to claim 31, wherein R$_{22}$ is hydrogen.
38. The compound according to claim 31, wherein R$_{23}$ is methyl, z is 1 and R$_{24}$ is hydrogen, preferably in (R)-configuration.

39. The compound according to claim 31, wherein $R_{25}$ is hydrogen and $R_{26}$ is methyl.

40. The compound according to claim 31, wherein $R_{25}$ is hydrogen.

41. A process for the preparation of a compound of the formula (I) in claim 1, which process comprises:
  a) for the preparation of a compound of formula (I) above in which A is bound to Ar via an O, S or N atom in A, and (i) n=0 and $R_1$ is a saturated aminoazacyclic, aminodiazacyclic, diazacyclic or diazabicyclic residue, or (ii) n=1, B is —N($R_6$)— or —N($R_6$)C($R_4$)($R_5$)—, wherein $R_4$, $R_5$ and $R_6$ are as defined in claim 1, and $R_1$ is a saturated or unsaturated azacyclic, or a saturated azabicyclic, residue, reacting a compound of the structural formula (III):

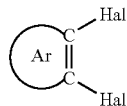

(III)

wherein Ar is as defined in claim 1 and Hal is halogen, with a compound R—A'—X'—H or its corresponding anion where X' is —O—, —S— or —N($R_{15}$)—, A' is $C_{1-8}$-alkylene wherein the carbon chain may be interrupted by one or more heteroatoms and which may have a terminal heteroatom binding to R, said heteroatoms being selected from N, O and S, and R is as defined in claim 1 and $R_{15}$ is as defined in claim 4, to produce a compound of the formula (IV):

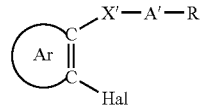

(IV)

wherein Ar, X', A', R and Hal are as defined above, and subsequently reacting the compound of formula (IV) with an appropriate amine to produce the compound of formula (I); or b) for the preparation of a compound of formula (I) in which n=1, B is oxygen or sulphur and $R_1$ is a saturated azacyclic or azabicyclic residue, or a group —[C($R_4$)($R_5$)]$_x$N($R_{2a}$)($R_{3a}$), wherein $R_2$, $R_3$, $R_4$, $R_5$ and x are as defined in claim 1, reacting a compound of formula (IV) above with a corresponding hydroxy- or mercapto-substituted azacyclic or azabicyclic compound, or with a compound HO—$R_1$ or HS—$R_1$, where $R_1$ is —[C($R_4$)($R_5$)]$_x$N($R_{2a}$)($R_{3a}$), wherein $R_2$, $R_3$, $R_4$, $R_5$ and x are as defined above, to produce the compound of formula (I); or c) for the preparation of a compound of formula (I), wherein A is bound to R via an oxygen or sulphur atom in A, reacting a compound of formula (V):

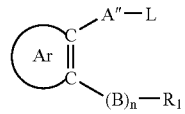

(V)

wherein Ar, $R_1$, B and n are as defined above, A" is $C_{1-8}$-alkylene wherein the carbon chain may be interrupted by one or more heteroatoms and which may have a terminal heteroatom bound to Ar, said heteroatoms being selected from N, O and S, and L is a hydroxy, thiol or a leaving group with a compound R—OH or R—SH, where R is as defined in claim 1, to produce the compound of formula (I); or d) for the preparation of a compound of formula (I), in which A is bound to Ar via an O, S or N atom in A, and wherein n=0, or n=1 and B is oxygen, nitrogen, sulphur or —N($R_6$)C($R_4$)($R_5$)—, wherein $R_4$, $R_5$ and $R_7$ are as defined in claim 1, reacting a compound of formula (III) above with an appropriate amine, or an appropriate hydroxy- or mercapto-substituted compound to produce a compound of formula (VI):

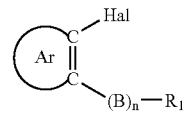

(VI)

wherein Ar, B, $R_1$, Hal and n are as defined in claim 1, and subsequently reacting the compound of formula (VI) with a compound R—A'—X'—H or its corresponding anion, where X' is —O—, —S— or —N($R_{15}$)—, A' is $C_{1-8}$-alkylene wherein the carbon chain may be interrupted by one or more heteroatoms and which may have a terminal heteroatom binding to R, said heteroatoms being selected from N, O and S, and R is as defined in claim 1 and $R_{15}$ is as defined in claim 4, to produce the compound of the formula (I);

optionally converting a resulting compound of formula (I) to another compound of formula (I);

and, if desired, separating a racemate obtained into optical isomers and/or forming an acid addition salt with an organic or inorganic acid.

42. A pharmaceutical composition comprising a compound according to claim 1 as an active ingredient, together with a pharmacologically and pharmaceutically acceptable carrier.

43. A method for the prophylaxis or treatment of a serotonin-related, especially 5-HT$_2$ receptor-related, disease in a human being or in an animal, particularly a disease related to the 5-HT$_{2c}$ receptor, especially selected from eating disorders, especially obesity, memory disorders, schizophrenia, mood disorders, anxiety disorders, pain, sexual dysfunctions, and urinary disorders, which method comprises administering an effective amount of a compound according to claim 1 to a subject suffering from said disease.

44. A method for modulating 5HT2 receptor function, especially 5HT$_{2c}$ receptor function, comprising contacting the receptor with an effective inhibitory amount of a compound according to claim 1.

45. The method of claim 43, wherein the mood disorders comprises major depression and bipolar depression including both mild and bipolar disorder, and seasonal affective disorder (SAD).

46. The method of claim 43, wherein the anxiety disorder comprises situational anxiety, generalized anxiety disorder, primary anxiety disorders and secondary anxiety disorders.

* * * * *

UNITED STATES PATENT AND TRADEMARK OFFICE
CERTIFICATE OF CORRECTION

PATENT NO.       : 7,071,180 B2                                            Page 1 of 1
APPLICATION NO.  : 10/873852
DATED            : July 4, 2006
INVENTOR(S)      : Bjorn M. Nilsson et al.

It is certified that error appears in the above-identified patent and that said Letters Patent is hereby corrected as shown below:

Column 8, line 40 and column 87, line 55, the top and bottom solid lines between X and (C)o and between (Y)p and (C)q in Formula (II), should appear as broken lines, as shown below:

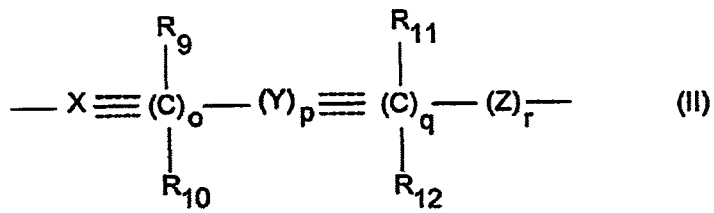

Column 89, line 26, "S—" should be changed to -- 5- --

Column 92, line 11, "$R_7$" should be changed to --$R_6$--

Signed and Sealed this

Twenty-eighth Day of November, 2006

JON W. DUDAS
*Director of the United States Patent and Trademark Office*